United States Patent
Rajagopal et al.

(10) Patent No.: US 10,639,629 B2
(45) Date of Patent: May 5, 2020

(54) SYSTEMS AND METHODS FOR SAMPLE CONCENTRATION AND DETECTION USING A SEPARATION LIQUID

(71) Applicant: 3M INNOVATIVE PROPERTIES COMPANY, St. Paul, MN (US)

(72) Inventors: Raj Rajagopal, Woodbury, MN (US); Kurt J. Halverson, Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/105,063

(22) PCT Filed: Dec. 16, 2014

(86) PCT No.: PCT/US2014/070523
§ 371 (c)(1),
(2) Date: Jun. 16, 2016

(87) PCT Pub. No.: WO2015/095145
PCT Pub. Date: Jun. 25, 2015

(65) Prior Publication Data
US 2016/0310941 A1     Oct. 27, 2016

Related U.S. Application Data

(60) Provisional application No. 61/919,001, filed on Dec. 20, 2013.

(51) Int. Cl.
*C12Q 1/24* (2006.01)
*B01L 3/00* (2006.01)

(52) U.S. Cl.
CPC ......... *B01L 3/50215* (2013.01); *B01L 3/5021* (2013.01); *C12Q 1/24* (2013.01);
(Continued)

(58) Field of Classification Search
CPC ........ B01L 3/50215; B01L 3/502; B01L 3/50; C12Q 1/24; C12Q 1/02; C12Q 1/00
(Continued)

(56) References Cited

U.S. PATENT DOCUMENTS

| 4,212,948 A | 7/1980 | Dprm |
| 4,539,256 A | 9/1985 | Shipman |

(Continued)

FOREIGN PATENT DOCUMENTS

| DE | 3722562 | 1/1989 |
| EP | 2147723 | 1/2010 |

(Continued)

OTHER PUBLICATIONS

Ingham, "The micro-Petri dish, a million-well growth chip for the culture and high-throughput screening of microorganisms", PNAS, 2007, vol. 104, No. 26, pp. 18217-18222.

(Continued)

*Primary Examiner* — Christine T Mui
(74) *Attorney, Agent, or Firm* — Qiang Han

(57) ABSTRACT

Systems and methods for concentrating a sample and detecting an analyte of interest using a separation liquid. The system can include a sample detection container that can include a microcavity. The microcavity can include a concentrate of a sample resulting from centrifugation of the sample. The container can further include a separation liquid located between the microcavity and a supernatant of the sample located outside of the microcavity. The separation liquid can have a density greater than that of the supernatant of the sample, and an interfacial tension with the supernatant of at least 0.05 N/m. The separation liquid can be non-toxic and inert. The method can include adding the separation liquid to the sample detection container, after centrifuging (Continued)

the sample detection container, to displace the supernatant located outside of the microcavity from the microcavity.

20 Claims, 25 Drawing Sheets

(52) U.S. Cl.
CPC .................. *B01L 2200/0605* (2013.01); *B01L 2200/0631* (2013.01); *B01L 2200/0642* (2013.01); *B01L 2200/0673* (2013.01); *B01L 2300/0636* (2013.01); *B01L 2300/0681* (2013.01); *B01L 2300/0832* (2013.01); *B01L 2300/0893* (2013.01); *B01L 2300/161* (2013.01); *B01L 2400/0409* (2013.01)

(58) Field of Classification Search
USPC .................. 422/552, 551, 500, 522; 436/177
See application file for complete search history.

(56) References Cited

U.S. PATENT DOCUMENTS

| | | | |
|---|---|---|---|
| 4,726,989 | A | 2/1988 | Mrozinski |
| 4,867,881 | A | 9/1989 | Kinzer |
| 4,959,301 | A | 9/1990 | Weaver |
| 5,120,594 | A | 6/1992 | Mrozinski |
| 5,260,360 | A | 11/1993 | Mrozinski |
| 5,716,798 | A | 2/1998 | Monthony |
| 5,770,440 | A | 6/1998 | Berndt |
| 5,833,860 | A | 11/1998 | Kopaciewicz |
| 5,888,594 | A | 3/1999 | David |
| 6,221,655 | B1 | 4/2001 | Fung |
| 6,386,699 | B1 | 5/2002 | Ylitalo |
| 6,391,578 | B2 | 5/2002 | Williams |
| 6,420,622 | B1 | 7/2002 | Johnston |
| 6,867,342 | B2 | 3/2005 | Johnston |
| 7,223,364 | B1 | 5/2007 | Johnston |
| 7,524,623 | B2 | 4/2009 | Gazenko |
| 7,582,472 | B2 | 9/2009 | Smith |
| 7,781,159 | B2 | 8/2010 | Gazenko |
| 8,067,154 | B2 | 11/2011 | Gazenko |
| 8,093,015 | B2 | 1/2012 | Obermann |
| 8,361,783 | B2 | 1/2013 | Gazenko |
| 8,535,945 | B2 | 9/2013 | Halverson |
| 8,647,508 | B2 | 2/2014 | Halverson |
| 2002/0128578 | A1 | 9/2002 | Johnston |
| 2003/0235677 | A1 | 12/2003 | Hanschen |
| 2007/0134784 | A1 | 6/2007 | Halverson |
| 2010/0129814 | A1 | 5/2010 | Walsh et al. |
| 2011/0039220 | A1 | 2/2011 | Zhou |
| 2011/0164862 | A1 | 7/2011 | Hirano |
| 2012/0048002 | A1 | 3/2012 | Mallet |
| 2012/0245038 | A1 | 9/2012 | Linton |

FOREIGN PATENT DOCUMENTS

| | | |
|---|---|---|
| WO | WO 1989-05456 | 6/1989 |
| WO | WO 2004-000569 | 12/2003 |
| WO | WO 2007-070310 | 6/2007 |
| WO | WO 2010-071764 | 6/2010 |
| WO | WO 2010-078234 | 7/2010 |
| WO | WO 2010-080232 | 7/2010 |
| WO | WO 2011-063332 | 5/2011 |
| WO | WO 2011-152967 | 12/2011 |
| WO | WO 2011-153085 | 12/2011 |
| WO | WO 2011-156251 | 12/2011 |
| WO | WO 2011-156258 | 12/2011 |
| WO | WO 2013-003308 | 1/2013 |
| WO | WO 2013-003309 | 1/2013 |
| WO | WO 2015-095142 | 6/2015 |

OTHER PUBLICATIONS

3M Company, "Fluorinert Liquids for Electronics Manufacturing", Product Information, 2003, pp. 1-4.
Chilvers, "Synthesis and evaluation of novel fluorogenic substrates for the detection of bacterial b-galactosidase", Journal of Applied Microbiology, 2001, vol. 91, 1118-1130.
Gunda, "Microspot With Integrated Wells (MSIW) for the Detection of *E. coli*", Proceedings of the ASME 2013 11th International Conference on Nanochannels, Microchannels, and Minichannels, 2013, pp. 1-6.
Sartorius Stedim Biotech, "VoluPAC tubes", 2006, pp. 1-2.
Walsh, "Rapid Intrinsic Fluorescence Method for Direct Identification of Pathogens in Blood Cultures", Journals.ASM.org, 2013, vol. 4, Issue 6, pp. 1-9.
International Search report for PCT International Application No. PCT/US2014/070523, dated Mar. 18, 2015, 4 pages.

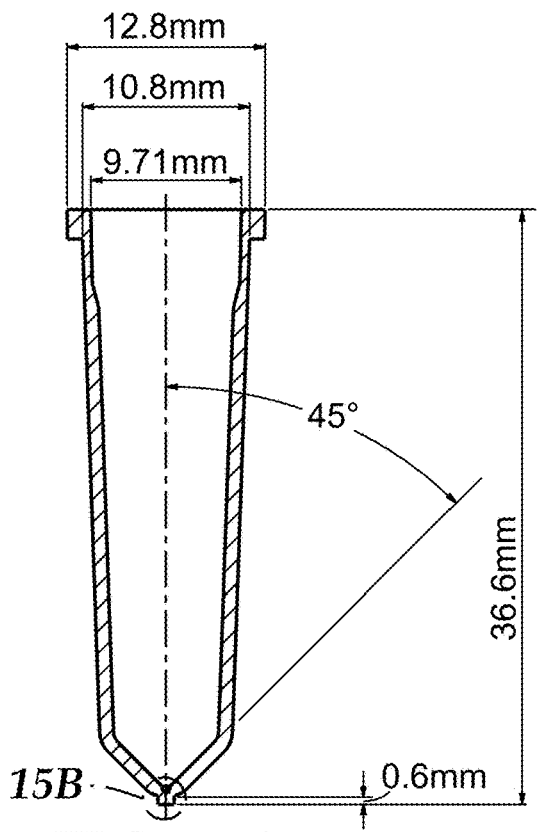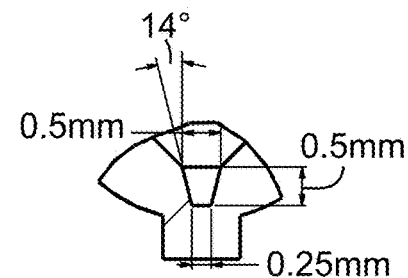
FIG. 15A
FIG. 15B
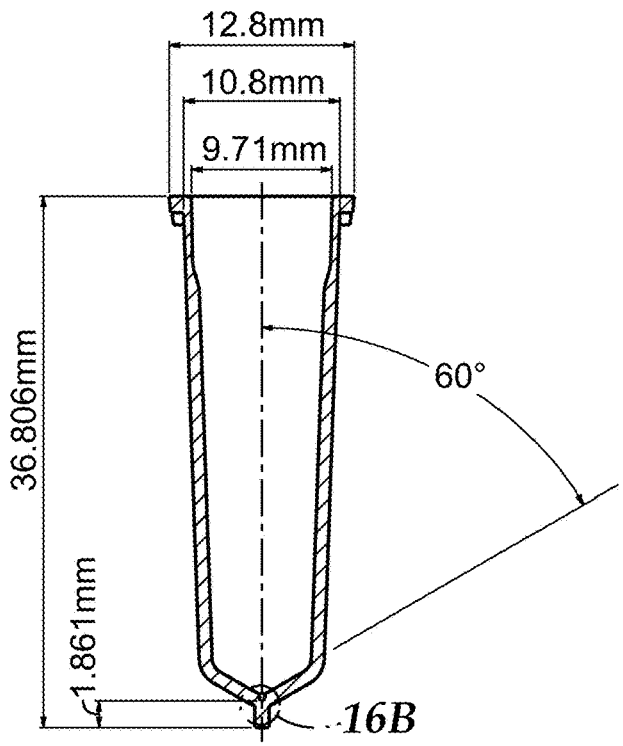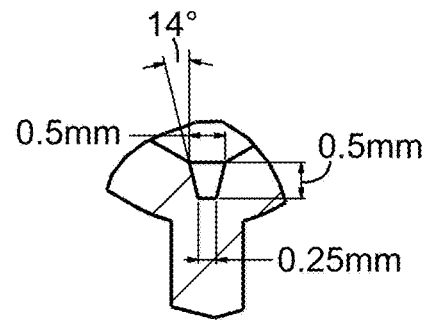
FIG. 16A
FIG. 16B

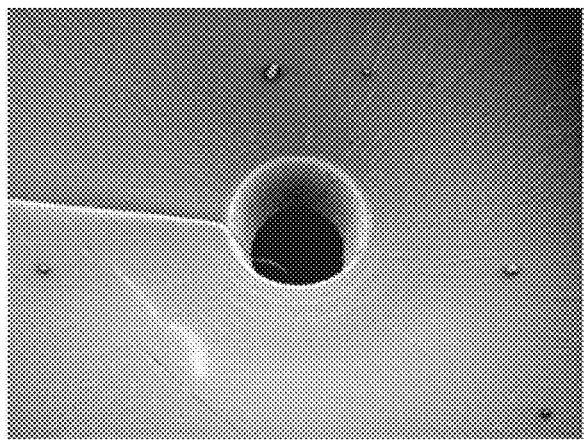
FIG. 22A  100μm
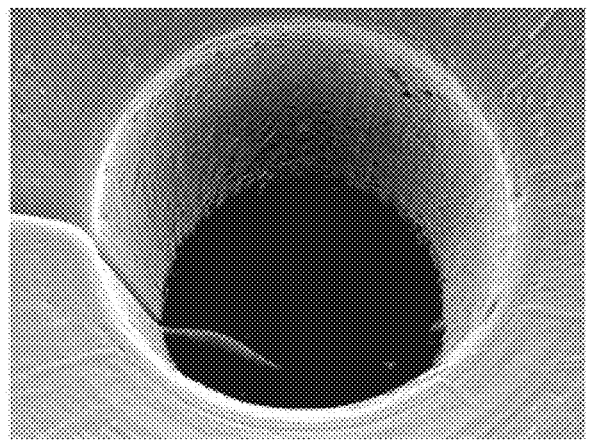
FIG. 22B  100μm
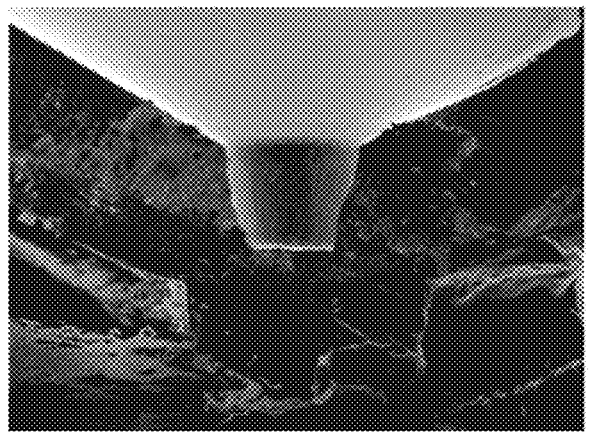
FIG. 22C  100μm
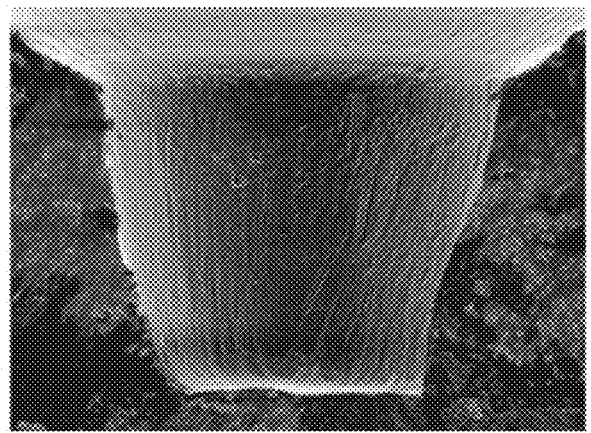
FIG. 22D  100μm 100μm 100μm 100μm 100μm 1μm 1μm

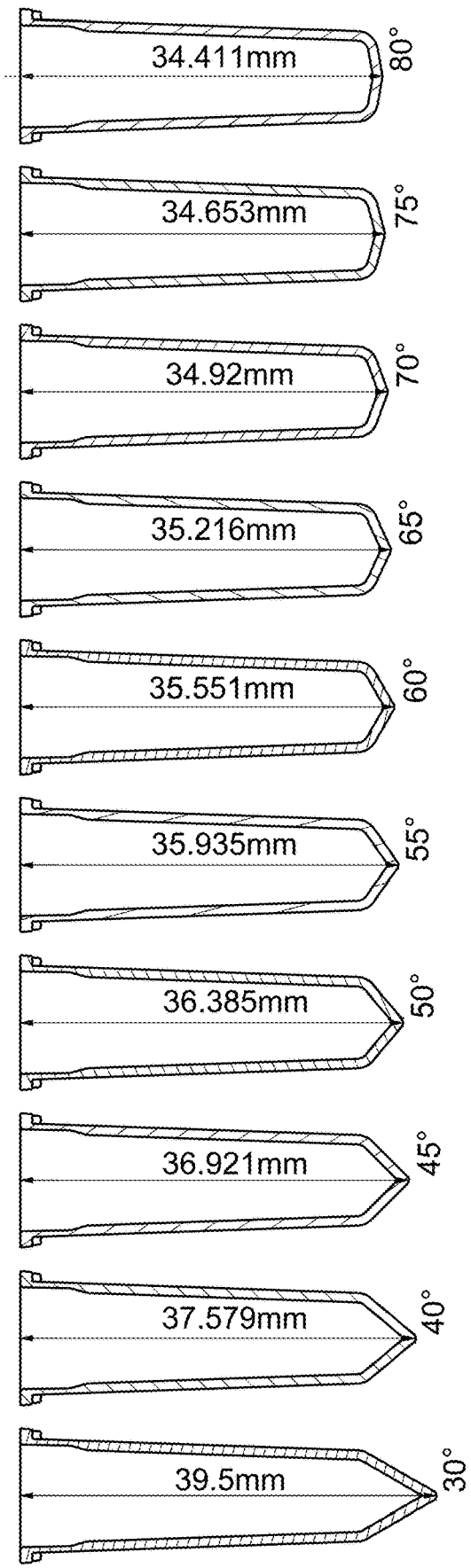

SYSTEMS AND METHODS FOR SAMPLE CONCENTRATION AND DETECTION USING A SEPARATION LIQUID

CROSS REFERENCE TO RELATED APPLICATIONS

This is a national stage filing under 35 U.S.C. § 371 of PCT Application No. PCT/US2014/070523, filed Dec. 16, 2014, which claims the benefit of U.S. Provisional Application No. 61/919,001, filed Dec. 20, 2013, the disclosure of which is incorporated herein by reference in its entirety.

FIELD

The present disclosure generally relates to systems and methods for detecting an analyte of interest, such as bacteria, in a sample, and particularly, to rapid detection of an analyte of interest in a relatively large sample volume.

BACKGROUND

Testing aqueous samples for the presence of microorganisms (e.g., bacteria, viruses, fungi, spores, etc.) and/or other analytes of interest (e.g., toxins, allergens, hormones, etc.) can be important in a variety of applications, including food and water safety, infectious disease diagnostics, and environmental surveillance. For example, comestible samples, such as foods, beverages, and/or public water consumed by the general population may contain or acquire microorganisms or other analytes, which can flourish or grow as a function of the environment in which they are located. This growth may lead to the proliferation of pathogenic organisms, which may produce toxins or multiply to infective doses. By way of further example, a variety of analytical methods can be performed on samples of non-comestible samples (e.g., groundwater, urine, etc.) to determine if a sample contains a particular analyte. For example, groundwater can be tested for a microorganism or a chemical toxin; and urine can be tested for a variety of diagnostic indicators to enable a diagnosis (e.g., diabetes, pregnancy, etc.).

SUMMARY

Some aspects of the present disclosure provide a sample detection container adapted to contain and concentrate a sample for detection of an analyte of interest, if present. The container can include an open end configured to receive a sample, and a closed end that includes a microcavity. The microcavity can include a top opening and a base, and can be configured to provide capillary forces to retain a sample of interest. The microcavity can include a concentrate of a sample resulting from centrifugation of the sample, the concentrate can include a sediment and at least a portion of a supernatant. The container can further include a separation liquid located between the microcavity and the supernatant that is located outside of the microcavity. The separation liquid can have a density greater than that of the supernatant of the sample, and an interfacial tension with the supernatant of at least 0.05 N/m. The separation liquid can be non-toxic and inert.

Some aspects of the present disclosure can provide a method for detecting an analyte of interest in a sample, if present. The method can include providing a sample detection container. The container can include an open end configured to receive a sample, and a closed end that includes a microcavity. The microcavity can include a top opening and a base and configured to provide capillary forces to retain a sample of interest. The method can further include positioning a sample in the sample detection container; and centrifuging the sample detection container toward the microcavity to form a sediment and a supernatant of the sample. The method can further include adding a separation liquid to the sample detection container, after centrifuging the sample detection container, to displace the supernatant located outside of the microcavity from the microcavity, such that a concentrate of the sample is retained in the microcavity, the concentrate comprising the sediment. The separation liquid can move between the microcavity and the supernatant located outside of the microcavity. The separation liquid can have a density greater than that of the supernatant of the sample, and an interfacial tension with the supernatant of at least 0.05 N/m. The separation liquid can be non-toxic and inert.

Other features and aspects of the present disclosure will become apparent by consideration of the detailed description and accompanying drawings.

BRIEF DESCRIPTION OF THE DRAWINGS

FIG. 15A a side cross-sectional view of SMD1, a sample detection container used in the Examples, SMD1 including a single microcavity and a wall having an effective angle α of 45 degrees.

FIG. 15B is a close-up side cross-sectional view of the microcavity of SMD1 of FIG. 15A.

FIG. 16A is a side cross-sectional view of SMD2, a sample detection container used in the Examples, SMD2 including a single microcavity and a wall having an effective angle α of 60 degrees.

FIG. 16B is a close-up side cross-sectional view of the microcavity of SMD2 of FIG. 16A.

FIGS. 22A-22D are optical micrographs of the microcavity of SMD2 of FIGS. 16A and 16B.

FIGS. 28A-28J illustrate side cross-sectional views of containers having various effective angles that were tested according to Example 9.

DETAILED DESCRIPTION

Figure 1:
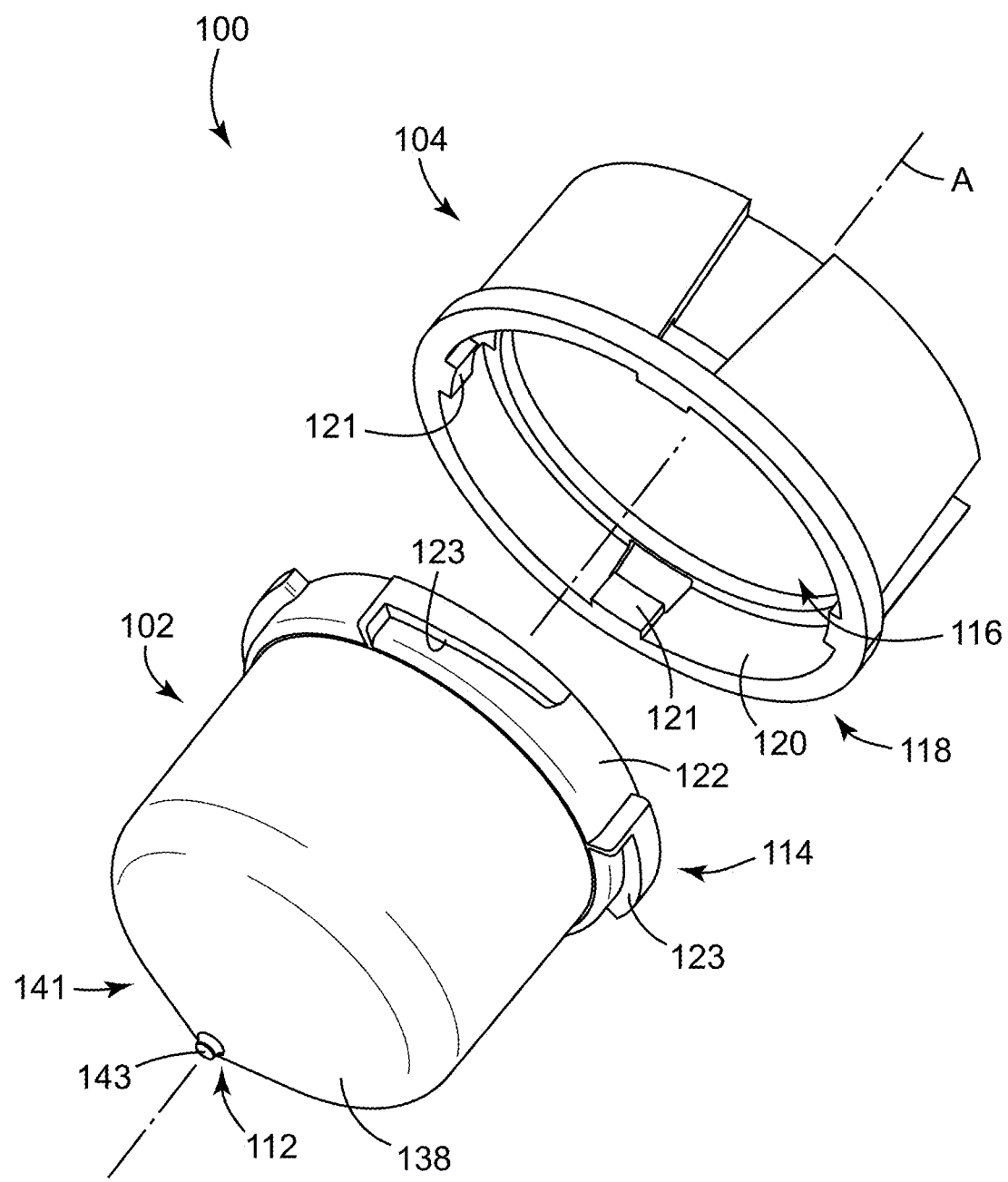
FIG. 1 is an exploded perspective view of a sample detection container according to one embodiment of the present disclosure.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled" and variations thereof are used broadly and encompass both direct and indirect couplings. It is to be understood that other embodiments may be utilized, and structural or logical changes may be made without departing from the scope of the present disclosure. Furthermore, terms such as "top," "bottom," and the like are only used to describe elements as they relate to one another, but need not recite specific orientations of the apparatus, to indicate or imply necessary or required orientations of the apparatus, or to specify how the invention described herein will be used, mounted, displayed, or positioned in use.

In a variety of samples that are desired to be tested for an analyte of interest, the analyte can be present in the sample at a low concentration. For example, regulations for water safety testing can require that testing devices be able to detect 1 colony-forming unit (cfu) of a bacterium of interest in 100 mL of water. Such a low concentration can be difficult or impossible to detect in a reasonable amount of time, much less in a "rapid" timeframe, which is described in greater detail below. In order to decrease detection time, in some cases, the sample may need to be concentrated into a smaller volume. That is, in some cases, in order to reach an appropriate concentration of an analyte of interest so as to achieve a detection threshold of an analytical technique in a shorter amount of time, the sample may need to be concentrated by several orders of magnitude.

In some existing systems and methods, centrifugation is used for samples having a high enough analyte concentration (e.g., bacterial concentration) to form a visible, packed "pellet" in the base of a centrifugation tube. The supernatant resulting from the centrifugation process can then be removed by decanting or aspiration. Visual inspection can be used in both decanting and aspiration to determine the appropriate volume of supernatant to be removed, and significant analyte loss can occur at the interface between the supernatant and the pellet. In addition, in samples having a particularly low concentration of the analyte of interest, the analyte may migrate to the base of the centrifugation flask during centrifugation but may not form a visible pellet or may not be tightly packed. In such situations, the analyte can be easily dislodged during decanting or aspiration, which can decrease the overall collection efficiency of the analyte of interest, and can reduce the accuracy of the sample testing procedure.

As a result, in some existing systems and methods, filtration alone can be employed to concentrate low-concentration samples. While filtration can increase the concentration of the analyte of interest in the sample, retrieving the concentrated sample from the filter can be difficult and/or time-consuming. For example, in some situations, large elution volumes (e.g., 5-100 mL) can be required to backflush or wash the concentrated sample off of the filter, particularly for large initial sample volumes that may have required a filter having a large diameter.

The present disclosure generally relates to systems and methods for detecting the presence or absence of an analyte of interest in a sample, particularly, in liquid samples, and more particularly, in dilute aqueous samples. Furthermore, the present disclosure generally relates to systems and methods for rapidly detecting the analyte. In some embodiments, the analyte is selected for detecting (e.g., the presence or absence of) *Escherichia coli* or other coliforms, for example, in a water sample. Detection of microorganisms (or other analytes) of interest in a water sample can be difficult, because of the low concentration of these microorganisms. As a result of the low concentration, detection in existing systems and methods can be very slow, because the microorganism(s) need to be grown (or the analyte concentration needs to be increased) to a detectable level, which can take time. The present inventors, however, have invented systems and methods for greatly decreasing the time needed to detect an analyte of interest in a water sample, and particularly, a dilute water sample.

Systems and methods of the present disclosure employ a sample detection container that is adapted to contain and concentrate (e.g., by centrifugation) a sample, while also retaining a concentrate of the sample for detection of an analyte of interest. Such a sample detection container can include a one or more microcavities at its closed end that is configured to receive and retain a concentrate of the sample (e.g., by capillary forces). Such a concentrate can include a sediment of the sample that can be formed during centrifugation. The microcavity can include a top opening, a base, and a longitudinal axis. In some embodiments, the sample detection container can include a wall (or sidewall or slanted wall) that extends to (e.g., tapers toward) the microcavity, and a portion of the wall that is located adjacent the top opening of the microcavity can have a slope that is oriented at an effective angle $\alpha$ with respect to the longitudinal axis of the microcavity. In some embodiments, the sample detection container can include, or be configured to receive, a separation liquid that is configured to separate (e.g., phase-separate) the concentrate contained in the microcavity from a bulk liquid (e.g., a supernatant resulting from centrifugation) located outside (e.g., above) the microcavity to isolate the concentrate from the remainder of the sample. Particularly, the separation liquid is configured to sit below the bulk supernatant and above the microcavity, such that the separation liquid is configured to be located between the microcavity (and its contents) and the supernatant located outside of the microcavity.

One microcavity will primarily be described for simplicity; however, it should be understood that any description pertaining to a single microcavity can also be extended to include a plurality of microcavities, or a "microcavity surface."

Some methods of the present disclosure can generally include providing the sample detection container; positioning a sample to be tested in the sample detection container; centrifuging the sample detection container in a first direction toward the microcavity to form a sediment and a supernatant of the sample; and adding a separation liquid to the sample detection container, after centrifuging, to displace the supernatant located outside of the microcavity from the microcavity, and to effectively isolate the concentrate of the sample contained in the microcavity from the supernatant.

As a result, the present inventors have discovered that detection time of an analyte of interest in a sample could be reduced by employing the separation liquid to isolate the concentrate of the sample in the microcavity. Such isolation of the concentrate generally minimizes the volume to be interrogated for the analyte of interest, which maximizes the resulting concentration of the anlayte(s) of interest (if present), and thereby minimizes the time needed to detect the analyte of interest.

Some methods of the present disclosure can further include inverting the sample detection container, after centrifuging the sample detection container, to decant at least a portion of the supernatant and the separation liquid away from the microcavity, such that a concentrate of the sample is retained in the microcavity, the concentrate comprising the sediment. Methods can further include interrogating the concentrate in the microcavity for the analyte of interest. Interrogation can be performed in the microcavity even when the separation liquid remains in the container above the microcavity.

As described in greater detail below, and as exemplified in the Examples, the present inventors have found particular benefits and advantages when the separation liquid has a density greater than that of the supernatant of the sample and a liquid-liquid interfacial tension with the supernatant of at least 50 dynes/cm (0.05 N/m). In addition, the separation liquid is generally non-toxic, so as not to have a toxic or otherwise deleterious effect on the analyte of interest (e.g. bacteria, spores, enzymes, DNA, RNA, metabolites, etc) in a sample to be tested, if present. Furthermore, the separation liquid is generally inert, such that the separation liquid does not chemically react with the sample detection system, including any portion of the sample or the sample detection container. Additionally, the separation liquid generally has a very low solubility in the supernatant of the sample and/or in water (e.g., less than 1%).

Sample detection containers of the present disclosure can include one or more microcavities. Sample detection containers with a single microcavity as well as sample detection containers with a microcavity surface (i.e., a plurality of microcavities generally making up an inner surface of the sample detection container) are both described, illustrated and exemplified herein.

In some embodiments, the sample detection container can include a wall that extends down to the one or more microcavities, and in some embodiments, at least a portion of the wall of the container can be tapered down toward the one or more microcavities, e.g., to facilitate movement of analytes of interest in the sample into the one or more microcavities, particularly, if a relatively small number of microcavities is employed. In such embodiments, the wall can be tapered or angled at an effective angle $\alpha$.

The effective angle $\alpha$ can vary between about 0 degrees and 90 degrees. In some embodiments, the portion of the wall that is of particular interest when describing the effective angle $\alpha$ is the portion of the wall that is located adjacent the top opening of the microcavity. In some embodiments, the portion of the wall "adjacent the top opening of the microcavity" that is oriented at the effective angle $\alpha$, can be a portion of the wall that is at least 5× a representative dimension of the microcavity, such that the portion of the wall oriented at effective angle $\alpha$ is comparatively large, relative to the order of magnitude of the microcavity. For example, a transverse dimension (e.g., that is orthogonal to the longitudinal axis) of the microcavity at its top opening can be used as a representative dimension, and the wall (or the portion thereof) that is oriented at the effective angle $\alpha$ is at least 5× that dimension. In some embodiments, the portion of the wall located adjacent the microcavity and oriented at the effective angle $\alpha$ is at least 10× the representative dimension of the microcavity, in some embodiments, at least 15×, in some embodiments, at least 20×, and in some embodiments, at least 50×.

In some cases (e.g., in situations that do not employ the separation liquids of the present disclosure), configuring the container to include a wall that has at least a portion adjacent the microcavity that is oriented at the effective angle $\alpha$, collection (and retention) of the analyte of interest in the microcavity can be maximized, while drainage of a majority of the supernatant resulting from the sedimentation (e.g., centrifugation) process away from the microcavity (e.g., upon inversion of the container) is also maximized (i.e., excess supernatant is not retained in the container above the microcavity (i.e., above the top opening of the microcavity or a plane defined by the top opening of the microcavity). Said another way, in some embodiments, configuring the container to include the wall oriented at the effective angle α can maximize the concentration of the analyte of interest, particularly, when one or a few microcavities, as described below, are employed. Additional details regarding effective angles α can be found in U.S. Application No. 61/918,977, filed Dec. 20, 2013, which is incorporated herein by reference in its entirety.

While other previous systems and methods may have concentrated samples and enabled relatively early detection of an analyte of interest, the systems and methods of the present disclosure have achieved even earlier detection by employing separation liquids to effectively isolate the concentrate of the sample in the one or more microcavities.

In addition, in some prior existing systems, achieving a concentrate (see, e.g., the concentrate 154 in FIGS. 4 and 5) that is substantially contained in a microstructure or microstructured surface was dependent upon the speed at which a container was inverted during an inversion step. However, systems and methods of the present disclosure that employ the separation liquid are effective at achieving a concentrate that is substantially contained in the microcavity, irrespective of whether inversion is even employed, and particularly, irrespective of the inversion speed.

"Substantially contained" can generally refer to the concentrate being contained within the microcavity with no visible (i.e., with the unaided or naked eye) sample liquid above the microcavity that may contain a larger volume of the sample or of the concentrate.

Such larger volumes can be undesirable because any analyte(s) of interest present in this larger volume may not be able to be properly detected (e.g., during imaging or optically interrogating) at least partly because the analyte(s), if present, will have a lower concentration in these larger volumes, and/or because the larger volume may not be suitably positioned for detection.

As for retrieving a concentrated sample (filtrand) from a filter, in the systems and methods of the present disclosure, the sample detection container can be used to further concentrate the eluted filtrand sample. That is, in some embodiments, systems and methods of the present disclosure can employ a combination of filtration and centrifugation into one or more microcavities in order to isolate and detect an analyte of interest from a sample, if present. As a result, even if large volumes are required for elution of the filtrand form the filter, the eluted filtrand sample (i.e., the filtrand retained from filtering plus any diluents such as elution solutions) can be further concentrated by centrifuging into a microcavity to achieve a high-concentration, small-volume (e.g., on the order of nanoliters) aliquot of the sample for relatively faster detection of an analyte of interest.

For example, a large dilute aqueous sample can be filtered to retain the analyte(s) of interest, if present, by size, charge and/or affinity. The analyte(s) can be retained on a first side of a filter, which can then be oriented to face a microcavity during a subsequent centrifugation process. A diluent (e.g., nutrient media, or the like) can be added to the filter, and the analyte(s) can be forced into the microcavity (or microcavities) by centrifugation. In such embodiments, the filtrand on the filter plus any additional diluent that is added can form the "sample," and the sample can be sedimented (e.g., by centrifugation) into the microcavity, such that a concentrate of the sample (i.e., a portion of the sample having a higher concentration than the starting sample) can be retained in the microcavity, where the concentrate comprises a sediment of the sample (i.e., higher density matter), which would include the analyte(s), if present. The microcavity can then be interrogated to detect the analyte(s), for example, by detecting the presence/absence of the analyte(s). Systems of the present disclosure can include container assemblies that are configured to facilitate the processes of filtering and centrifuging, as well as the transition between the filtration step and the centrifugation step. In addition, the systems and methods of the present disclosure allow for concentration of a large volume sample down to a very small volume, for example, from about 1 L down to about 1 microliter, or even 1 nL (e.g., in a microcavity).

Particularly, in some embodiments, the systems and methods of the present disclosure can include performing a first concentration step comprising filtering an original sample using a filter that is configured to retain one or more analyte(s) of interest to form a filtrand on one side of the filter; optionally adding one or more diluents to the filtrand and using the filtrand and any added diluents as the new or second sample; and performing a concentration step comprising concentrating the second sample (e.g., based on density) into a microcavity (or plurality of microcavities), where the microcavity can serve as an individual "test tube" of a small volume (e.g., on the scale of microliters or nanoliters), resulting in a high concentration of the analyte(s) of interest, if present, in the sample. This increase in concentration of the analyte(s) of interest can facilitate and expedite detection of the anlayte(s), for example, for detecting the presence/absence of the analyte(s).

In some existing systems and methods, portions of the sample can become irreversibly trapped in the filter during filtration. Trapping can be overcome using isoporous filters, however, filtration through isoporous filters can be slow, and the pores of the isoporous filter can be easily and rapidly plugged during filtration. However, the present inventors have discovered that certain filters allow for better recovery of the analyte of interest (e.g., of microorganisms, such as bacteria). For example, as described in greater detail below, "multi-zone" filter membranes (i.e., filters comprising multiple zones of porosity) can be particularly useful for recovering bacteria from the filter. This is because the porosity of the filter changes with its z dimension (i.e., depth). The present inventors discovered that by using such multi-zone filters and using the side of the filter having the smallest pore size as the "first side" of the filter (i.e., the side of the filter through which the sample passes first and on which the filtrand is collected), particular advantages in recovering the analyte of interest can be achieved.

However, as described above, even if such multi-zone filters are not used, the systems and methods of the present disclosure are still more effective than prior filtration-only systems and methods, because the systems and methods of the present disclosure that employ filtration further concentrate the eluted filtrand sample into a microcavity (or microcavities) by centrifugation, for example, to improve the time-to-detect an analyte of interest.

In some embodiments, the analyte of interest can be a microorganism of interest itself, and in some embodiments, the analyte can be an indicator of a viable microorganism of interest. In some embodiments, the present disclosure can include systems and methods for determining the presence/absence of microorganism(s) of interest in a sample by interrogating the sample for analyte(s) of interest that are representative of the microorganism(s).

In some embodiments, rapid detection can refer to detection in no greater than 8 hours, in some embodiments, no greater than 6 hours, in some embodiments, no greater than 5 hours, in some embodiments, no greater than 4 hours, and in some embodiments, no greater than 3 hours. The detection time, however, can be dependent upon the type of analyte being detected because some microorganisms grow more quickly than others and will therefore reach a detectable threshold more rapidly. One of skill in the art will understand how to identify the appropriate assays (e.g., including the appropriate enzymes and enzymes substrates) to detect an analyte (e.g., microorganism) of interest. However, no matter which assay is used, or which analyte is selected, for a given analyte of interest, the systems and methods of the present disclosure will generally achieve a time-to-result more quickly than that achieved with standard culture techniques (e.g., growth-based detection in a microtiter plate (e.g., 96-well). That is, the systems and methods of the present disclosure can detect the anlayte at least 25% faster than standard culture techniques (e.g., where each well contains 100 microliters of a sample), in some embodiments, at least 50% faster, in some embodiments, at least 75% faster, and in some embodiments, at least 90% faster.

Such samples to be analyzed for an analyte of interest can be obtained in a variety of ways. For example, in some embodiments, the sample to be analyzed itself is a liquid sample, such as a dilute liquid sample and/or a dilute aqueous sample. In some embodiments, the sample can include the liquid resulting from washing or rinsing a source of interest (e.g., a surface, fomite, etc.) with a diluent. In some embodiments, the sample can include the filtrate resulting from filtering or settling a liquid composition resulting from combining a source of interest with an appropriate diluent. That is, large insoluble matter and/or matter having a lower or higher density than the analyte(s) of interest, such as various foods, fomites, or the like, can be removed from a liquid composition in a first filtration or settling step to form the sample that will be analyzed using a method of the present disclosure.

The term "source" can be used to refer to a food or nonfood desired to be tested for analytes. The source can be a solid, a liquid, a semi-solid, a gelatinous material, and combinations thereof. In some embodiments, the source can be provided by a substrate (e.g., a swab or a wipe) that was used, for example, to collect the source from a surface of interest. In some embodiments, the liquid composition can include the substrate, which can be further broken apart (e.g., during an agitation or dissolution process) to enhance retrieval of the source and any analyte of interest. The surface of interest can include at least a portion of a variety of surfaces, including, but not limited to, walls (including doors), floors, ceilings, drains, refrigeration systems, ducts (e.g., airducts), vents, toilet seats, handles, doorknobs, handrails, bedrails (e.g., in a hospital), countertops, tabletops, eating surfaces (e.g., trays, dishes, etc.), working surfaces, equipment surfaces, clothing, etc., and combinations thereof. All or a portion of the source can be used to obtain a sample that is to be analyzed using the methods of the present disclosure. For example, a "source" can be a water supply or water moving through a pipeline, and a relatively large volume sample can be taken from that source to form a sample that will be tested with the systems and methods of the present disclosure. Therefore, the "sample" can also be from any of the above-described sources.

The term "food" is generally used to refer to a solid, liquid (e.g., including, but not limited to, solutions, dispersions, emulsions, suspensions, etc., and combinations thereof) and/or semi-solid comestible composition. Examples of foods include, but are not limited to, meats, poultry, eggs, fish, seafood, vegetables, fruits, prepared foods (e.g., soups, sauces, pastes), grain products (e.g., flour, cereals, breads), canned foods, milk, other dairy products (e.g., cheese, yogurt, sour cream), fats, oils, desserts, condiments, spices, pastas, beverages, water, animal feed, drinking water, other suitable comestible materials, and combinations thereof.

The term "nonfood" is generally used to refer to sources of interest that do not fall within the definition of "food" and are generally not considered to be comestible. Examples of nonfood sources can include, but are not limited to, clinical samples, cell lysates, whole blood or a portion thereof (e.g., serum), other bodily fluids or secretions (e.g., saliva, sweat, sebum, urine), feces, cells, tissues, organs, biopsies, plant materials, wood, soil, sediment, medicines, cosmetics, dietary supplements (e.g., ginseng capsules), pharmaceuticals, fomites, other suitable non-comestible materials, and combinations thereof.

The term "fomite" is generally used to refer to an inanimate object or substrate capable of carrying infectious organisms and/or transferring them. Fomites can include, but are not limited to, cloths, mop heads, towels, sponges, wipes, eating utensils, coins, paper money, cell phones, clothing (including shoes), doorknobs, feminine products, diapers, etc., portions thereof, and combinations thereof.

The term "analyte" is generally used to refer to a substance to be detected (e.g., by a laboratory or field test). A sample can be tested for the presence, quantity and/or viability of particular analytes. Such analytes can be present within a source (e.g., on the interior), or on the exterior (e.g., on the outer surface) of a source. Examples of analytes can include, but are not limited to, microorganisms, biomolecules, chemicals (e.g. pesticides, antibiotics), metal ions (e.g. mercury ions, heavy metal ions), metal-ion-containing complexes (e.g., complexes comprising metal ions and organic ligands), enzymes, coenzymes, enzyme substrates, indicator dyes, stains, adenosine triphophate (ATP), adenosine diphophate (ADP), adenylate kinase, luciferase, luciferin, and combinations thereof.

A variety of testing methods can be used to identify or quantitate an analyte of interest, including, but not limited to, microbiological assays, biochemical assays (e g immunoassay), or a combination thereof. In some embodiments, analytes of interest can be detected genetically; immunologically; colorimetrically; fluorimetrically; luminetrically; by detecting an enzyme released from a live cell in the sample; by detecting light that is indicative of the analyte of interest; by detecting light by absorbance, reflectance, fluorescence, or combinations thereof; or combinations thereof. That is, in some embodiments, interrogating the sample (or a concentrate of the sample) includes optically interrogating the sample, which can include any of the above-described types of optical interrogation, or any described below.

Specific examples of testing methods that can be used include, but are not limited to, antigen-antibody interactions, molecular sensors (affinity binding), thermal analysis, microscopy (e.g., light microscopy, fluorescent microscopy, immunofluorescent microscopy, scanning electron microscopy (SEM), transmission electron microscopy (TEM)), spectroscopy (e.g., mass spectroscopy, nuclear magnetic resonance (NMR) spectroscopy, Raman spectroscopy, infrared (IR) spectroscopy, x-ray spectroscopy, attenuated total reflectance spectroscopy, Fourier transform spectroscopy, gamma-ray spectroscopy, etc.), spectrophotometry (e.g., absorbance, reflectance, fluorescence, luminescence, colorimtetric detection etc.), electrochemical analysis, genetic techniques (e.g., polymerase chain reaction (PCR), transcription mediated amplification (TMA), hybridization protection assay (HPA), DNA or RNA molecular recognition assays, etc.), adenosine triphosphate (ATP) detection assays, immunological assays (e.g., enzyme-linked immunosorbent assay (ELISA)), cytotoxicity assays, viral plaque assays, techniques for evaluating cytopathic effect, other suitable analyte testing methods, or a combination thereof.

The term "microorganism" is generally used to refer to any prokaryotic or eukaryotic microscopic organism, including without limitation, one or more of bacteria (e.g., motile or vegetative, Gram positive or Gram negative), viruses (e.g., Norovirus, Norwalk virus, Rotavirus, Adenovirus, DNA viruses, RNA viruses, enveloped, non-enveloped, human immunodeficiency virus (HIV), human Papillomavirus (HPV), etc.), bacterial spores or endospores, algae, fungi (e.g., yeast, filamentous fungi, fungal spores), prions, mycoplasmas, and protozoa. In some cases, the microorganisms of particular interest are those that are pathogenic, and the term "pathogen" is used to refer to any pathogenic microorganism. Examples of pathogens can include, but are not limited to, members of the family Enterobacteriaceae, or members of the family Micrococaceae, or the genera *Staphylococcus* spp., *Streptococcus*, spp., *Pseudomonas* spp., *Enterococcus* spp., *Salmonella* spp., *Legionella* spp., *Shigella* spp., *Yersinia* spp., *Enterobacter* spp., *Escherichia* spp., *Bacillus* spp., *Listeria* spp., *Campylobacter* spp., *Acinetobacter* spp., *Vibrio* spp., *Clostridium* spp., and *Corynebacterium* spp. Particular examples of pathogens can include, but are not limited to, *Escherichia coli* including enterohemorrhagic *E. coli* e.g., serotype O157:H7, O129:H11; *Pseudomonas aeruginosa; Bacillus cereus; Bacillus anthracia; Salmonella enteritidis; Salmonella enterica* serotype Typhimurium; *Listeria monocytogenes; Clostridium botulinum; Clostridium perfringens; Staphylococcus aureus*; methicillin-resistant *Staphylococcus aureus; Campylobacter jejuni; Yersinia enterocolitica; Vibrio vulnificus; Clostridium difficile*; vancomycin-resistant *Enterococcus; Enterobacter [Cronobacter] sakazakii*; and coliforms. Environmental factors that may affect the growth of a microorganism can include the presence or absence of nutrients, pH, moisture content, oxidation-reduction potential, antimicrobial compounds, temperature, atmospheric gas composition and biological structures or barriers.

The term "biomolecule" is generally used to refer to a molecule, or a derivative thereof, that occurs in or is formed by an organism. For example, a biomolecule can include, but is not limited to, at least one of an amino acid, a nucleic acid, a polypeptide, a protein, a polynucleotide, a lipid, a phospholipid, a saccharide, a polysaccharide, and combinations thereof. Specific examples of biomolecules can include, but are not limited to, a metabolite (e.g., staphylococcal enterotoxin), an allergen (e.g., peanut allergen(s), egg allergen(s), pollens, dust mites, molds, danders, or proteins inherent therein, etc.), a hormone, a toxin (e.g., *Bacillus* diarrheal toxin, aflatoxin, *Clostridium difficile* toxin etc.), RNA (e.g., mRNA, total RNA, tRNA, etc.), DNA (e.g., plasmid DNA, plant DNA, etc.), a tagged protein, an antibody, an antigen, ATP, and combinations thereof.

The terms "soluble matter" and "insoluble matter" are generally used to refer to matter that is relatively soluble or insoluble in a given medium, under certain conditions. Specifically, under a given set of conditions, "soluble matter" is matter that goes into solution and can be dissolved in the solvent (e.g., diluent) of a system. "Insoluble matter" is matter that, under a given set of conditions, does not go into solution and is not dissolved in the solvent of a system. A source, or a sample taken from that source, can include soluble matter and insoluble matter (e.g., cell debris). Insoluble matter is sometimes referred to as particulate(s), precipitate(s), or debris and can include portions of the source material itself (i.e., from internal portions or external portions (e.g., the outer surface) of the source) or other source residue or debris resulting from an agitation process. In addition, a liquid composition comprising the source and a diluent can include more dense matter (i.e., matter having a higher density than the diluent and other matter in the mixture) and less dense matter (i.e., matter having a lower density than the diluent and other matter in the mixture). As a result, a diluent of the sample can be selected, such that the analyte(s) of interest is(are) more dense than the diluent and can be concentrated via settling (e.g., centrifugation).

The term "diluent" is generally used to refer to a liquid added to a source material to disperse, dissolve, suspend, emulsify, wash and/or rinse the source. A diluent can be used in forming a liquid composition, from which a sample to be analyzed using the methods of the present disclosure can be obtained. In some embodiments, the diluent is a sterile liquid. In some embodiments, the diluent can include a variety of additives, including, but not limited to, surfactants, or other suitable additives that aid in dispersing, dissolving, suspending or emulsifying the source for subsequent analyte testing; rheological agents; antimicrobial neutralizers (e.g., that neutralize preservatives or other antimicrobial agents); enrichment or growth medium comprising nutrients (e.g., that promote selective growth of desired microorganism(s)) and/or growth inhibitors (e.g., that inhibit the growth of undesired microorganism(s)); pH buffering agents; enzymes; indicator molecules (e.g. pH or oxidation/reduction indicators); spore germinants; an agent to neutralize sanitizers (e.g., sodium thiosulfate neutralization of chlorine); an agent intended to promote bacterial resuscitation (e.g., sodium pyruvate); stabilizing agents (e.g., that stabilize the analyte(s) of interest, including solutes, such as sodium chloride, sucrose, etc.); or a combination thereof. In some embodiments, the diluent can include sterile water (e.g., sterile double-distilled water ($ddH_2O$)); one or more organic solvents to selectively dissolve, disperse, suspend, or emulsify the source; aqueous organic solvents, or a combination thereof. In some embodiments, the diluent is a sterile buffered solution (e.g., Butterfield's Buffer, available from Edge Biological, Memphis Tenn.). In some embodiments, the diluent is a selective or semi-selective nutrient formulation, such that the diluent may be used in the selective or semi-selective growth of the desired analyte(s) (e.g., bacteria). In such embodiments, the diluent can be incubated with a source for a period of time (e.g., at a specific temperature) to promote such growth and/or development of the desired analyte(s).

Examples of growth medium can include, but are not limited to, Tryptic Soy Broth (TSB), Buffered Peptone Water (BPW), Universal Pre-enrichment Broth (UPB), *Listeria* Enrichment Broth (LEB), Lactose Broth, Bolton broth, or other general, non-selective, or mildly selective media known to those of ordinary skill in the art. The growth medium can include nutrients that support the growth of more than one desired microorganism (i.e., analyte of interest).

Examples of growth inhibitors can include, but are not limited to, bile salts, sodium deoxycholate, sodium selenite, sodium thiosulfate, sodium nitrate, lithium chloride, potassium tellurite, sodium tetrathionate, sodium sulphacetamide, mandelic acid, selenite cysteine tetrathionate, sulphamethazine, brilliant green, malachite green oxalate, crystal violet, Tergitol 4, sulphadiazine, amikacin, aztreonam, naladixic acid, acriflavine, polymyxin B, novobiocin, alafosfalin, organic and mineral acids, bacteriophages, dichloran rose bengal, chloramphenicol, chlortetracycline, certain concentrations of sodium chloride, sucrose and other solutes, and combinations thereof.

The term "agitate" and derivatives thereof is generally used to describe the process of giving motion to a liquid composition, for example, to mix or blend the contents of such liquid composition. A variety of agitation methods can be used, including, but not limited to, manual shaking, mechanical shaking, ultrasonic vibration, vortex stirring, manual stirring, mechanical stirring (e.g., by a mechanical propeller, a magnetic stirbar, or another agitating aid, such as ball bearings), manual beating, mechanical beating, blending, kneading, and combinations thereof.

The term "filtering" is generally used to refer to the process of separating matter by size, charge and/or function. For example, filtering can include separating soluble matter and a solvent (e.g., diluent) from insoluble matter, or filtering can include separating soluble matter, a solvent and relatively small insoluble matter from relatively large insoluble matter. As a result, a liquid composition can be "pre-filtered" to obtain a sample that is to be analyzed using the methods of the present disclosure. A variety of filtration methods can be used, including, but not limited to, passing the liquid composition (e.g., comprising a source of interest, from which a sample to concentrated can be obtained) through a filter, other suitable filtration methods, and combinations thereof.

"Settling" is generally used to refer to the process of separating matter by density, for example, by allowing the more dense matter in the liquid composition (i.e., the matter having a higher density than the diluent and other matter in the mixture) to settle or sink and/or by allowing the less dense matter in the liquid composition (i.e., the matter having a lower density than the diluent and other matter in the mixture) to rise or float. Settling may occur by gravity or by centrifugation. The more dense matter can then be separated from the less dense matter (and diluent) by aspirating the less dense (i.e., unsettled or floating) and diluent from the more dense matter, decanting the less dense matter and diluent, or a combination thereof. Pre-settling steps can be used in addition to or in lieu of pre-filtering steps to obtain a sample that is to be concentrated using the sample detection systems and methods of the present disclosure.

A "filter" is generally used to describe a device used to separate the soluble matter (or soluble matter and relatively small insoluble matter) and solvent from the insoluble matter (or relatively large insoluble matter) in a liquid composition and/or to filter a sample during sample concentration. Examples of filters can include, but are not limited to, a woven or non-woven mesh (e.g., a wire mesh, a cloth mesh, a plastic mesh, etc.), a woven or non-woven polymeric web (e.g., comprising polymeric fibers laid down in a uniform or nonuniform process, which can be calendered), a surface filter, a depth filter, a membrane (e.g., a ceramic membrane (e.g., ceramic aluminum oxide membrane filters available under the trade designation ANOPORE from Whatman Inc., Florham Park, N.J.), a polycarbonate membrane (e.g., track-etched polycarbonate membrane filters available under the trade designation NUCLEOPORE from Whatman, Inc.)), a polyester membrane (e.g., comprising track-etched polyester, etc.), a sieve, glass wool, a frit, filter paper, foam, etc., and combinations thereof.

In some embodiments, the filter can be configured to separate a microorganism of interest from a sample, for example, by size, charge, and/or affinity. For example, in some embodiments, the filter can be configured to retain a microorganism of interest, such that a filtrand retained on the filter comprises the microorganism of interest.

In some embodiments, the filter can be configured to retain at least 30% of the analyte(s) of interest in a sample (e.g., microorganisms of interest), in some embodiments, at least 50%, in some embodiments, at least 80%, in some embodiments, at least 85%, in some embodiments, at least 90%, and in some embodiments, at least 95%.

Additional examples of suitable filters are described in co-pending PCT Publication No. WO2011/156251 (Rajagopal, et al.), which claims priority to U.S. Patent Application No. 61/352,229; PCT Publication No. WO2011/156258 (Mach et al.), which claims priority to U.S. Patent Application No. 61/352,205; PCT Publication No. WO2011/152967 (Zhou), which claims priority to U.S. Patent Application Nos. 61/350,147 and 61/351,441; and PCT Publication No. WO2011/153085 (Zhou), which claims priority to U.S. Patent Application Nos. 61/350,154 and 61/351,447, all of which are incorporated herein by reference in their entirety.

In some embodiments, the term "filtrate" is generally used to describe the liquid remaining after the insoluble matter (or at least the relatively large insoluble matter) has been separated or removed from a liquid composition. In some embodiments, the term "supernatant" is generally used to describe the liquid remaining after the more dense matter has been separated or removed from a liquid composition. Such a filtrate and/or supernatant can form a sample to be used in the present disclosure. In some embodiments, the filtrate and/or supernatant can be incubated for a period of time to grow a microorganism of interest, and the resulting incubated filtrate and/or supernatant can form a sample to be used in the present disclosure. In some embodiments, growth media can be added to aid in growing the microorganism of interest.

In some embodiments, the term "filtrand" is generally used to describe the solid remaining after a liquid source (e.g., water to be tested) has been filtered to separate insoluble matter from soluble matter. Such a filtrand can be further diluted, and optionally agitated, grown (e.g., by adding growth media), and/or incubated, to form a sample to be used in the present disclosure. The filtrand may be present on one surface or side of the filter, and/or may have penetrated at least partially into the depth of the filter. As a result, in some embodiments, a diluent comprising an elution solution, a wash solution, or the like can be used to facilitate removing the filtrand from the filter. In some embodiments, surface filters can be preferred (e.g., over depth filters) for facilitating and enhancing removal of the filtrand from the filter.

In some embodiments, the g-force exerted on the filtrand in the subsequent centrifugation step can aid in removing the filtrand from the filter. In some cases, the retained analyte(s) of interest (e.g., microorganisms) can be eluted from the filter by repositioning the filter so that the force of gravity causes the retained biological organisms to dislodge and thereby elute from the filter. In other cases, retained analyte(s) may be eluted from the filter by manually shaking the filter to dislodge the retained analyte(s) from the filter. In other cases, retained analyte(s) may be eluted by vortexing the filter to dislodge the retained analyte(s) from the filter. In other cases, analyte(s) may be eluted from the filter by foam elution.

In some embodiments in which the analyte(s) of interest (e.g., microorganisms) are detected and/or quantified following recovery from the filter, methods of the present disclosure can include eluting at least 50% of the retained analyte(s) of interest from the filter, although the method may be performed after eluting less than 50% of the retained analyte(s) from the filter. In some embodiments, at least 60% of the retained analyte(s) can be eluted from the filter, in some embodiments, at least 70%, in some embodiments, at least 75%, in some embodiments, at least 80%, in some embodiments, at least 90%, and in some embodiments, at least 95%.

In some embodiments, no matter what form the starting sample is in, or how it was obtained, the sample can be agitated, grown (e.g., by adding growth media), and/or incubated, to form a sample to be analyzed by systems and methods of the present disclosure. In some embodiments, various reagents can be added at various stages of the process, including, but not limited to being added to the original sample, being added to the filtrand (e.g., with a diluent) or supernatant used to form the sample to be tested, being coated and/or dried in one or more microcavities, that will serve as the detection vessels for a concentrate of the sample, or combinations thereof.

In some embodiments, the term "sediment" is generally used to describe the "pellet" or solid that is separated from the supernatant after the more dense matter has been separated or removed from a liquid composition, for example via centrifugation.

The term "microcavity," and derivatives thereof, is generally used to refer to a receptacle, recess, depression, or well that is configured to retain a liquid, a solid, a semi-solid, a gelatinous material, another suitable material, or a combination thereof, particularly, under normal gravitational forces, in any orientation (e.g., by capillary forces).

In some embodiments, a "microcavity" can be no greater than 1000 micrometers in at least two of the possible dimensions, in some embodiments, no greater than 500 micrometers, and in some embodiments, no greater than 200 micrometers. However, in some embodiments of the present disclosure, a "microcavity" can be any receptacle, recess, depression, or well that is sufficient to retain a portion of a sample (e.g., a liquid concentrate of a sample after centrifugation toward the microcavity) under normal gravitational forces, at any orientation. Therefore, the microcavities of the present disclosure can have a sufficient depth (e.g., z dimension), or ratio (i.e., "aspect ratio") of a z dimension to an x-y dimension (or vice versa), that provides sufficient capillary force to retain a sample (e.g., a concentrated liquid comprising a sediment of a sample) of a given surface tension. The surface energy of the microcavity can be controlled (e.g., modified with a surface treatment) to enhance retention, however, generally, microcavities of the present disclosure can have an aspect ratio that provides the necessary capillary forces to retain a sample of interest.

In some embodiments, the aspect ratio can be at least about 0.1, in some embodiments, at least about 0.25, in some embodiments, at least about 0.5, in some embodiments, at least about 1, in some embodiments, at least about 2, in some embodiments, at least about 5, and in some embodiments, at least about 10. Because, in some embodiments, the x-y dimension of a microcavtiy (e.g., a recess) can change along its depth or z dimension (e.g., if the feature includes a draft angle), the aspect ratio can be the ratio of a z dimension to a "representative" x-y dimension. The representative x-y dimension is generally orthogonal to a longitudinal axis of the microcavity and is distinguished from a depth or z dimension of the microcavity. The representative x-y dimension can be a top dimension (i.e., the x-y dimension at the top opening of the microcavity), a bottom dimension (e.g., the x-y dimension at the base of the microcavity), a middle dimension (e.g., the x-y dimension at the half-depth/height position), an average x-y dimension (e.g., averaged along the depth/height), another suitable representative dimension, or the like.

In some embodiments, the representative x-y dimension is at least about 1 micrometer, in some embodiments, at least about 10 micrometers, and in some embodiments, at least about 50 micrometers. In some embodiments, the representative x-y dimension is less than about 1000 micrometers, in some embodiments, less than about 500 micrometers, and in some embodiments, less than about 100 micrometers.

In some embodiments, the depth or z dimension of the microcavity (i.e., the distance between a closed end, or base, of the microcavity and an open end, or top opening, of the microcavity) is at least about 5 micrometers, in some embodiments, at least about 20 micrometers, and in some embodiments, at least about 30 micrometers. In some embodiments, the average depth of the microcavity can be no greater than about 1000 micrometers, in some embodiments, no greater than about 250 micrometers, in some embodiments, no greater than about 100 micrometers, and in some embodiments, no greater than about 50 micrometers.

In some embodiments, the individual microcavity volume can be at least about 1 picoliter (pL), in some embodiments, at least about 10 pL, in some embodiments, at least about 100 pL, and in some embodiments, at least about 1000 pL (1 nL). In some embodiments, the microcavity volume can be no greater than about 1,000,000 pL (1 µL), in some embodiments, no greater than about 100,000 pL, in some embodiments, no greater than about 10,000 pL. In some embodiments, the microcavity volume ranges from 10 nL (10,000 pL) to 100 nL (100,000 pL).

The phase "substantially transparent" is generally used to refer to a body or substrate that transmits at least 50% of electromagnetic radiation having wavelengths at a selected wavelength or within a selected range of wavelengths in the ultraviolet to infrared spectrum (e.g., from about 200 nm to about 1400 nm; "UV-IR"), in some embodiments, at least about 75% of a selected wavelength (or range) in the UV-IR spectrum, and in some embodiments, at least about 90% of a selected wavelength (or range) in the UV-IR spectrum.

The phrase "substantially non-transparent" is generally used to refer to a body or substrate that transmits less than 50% of electromagnetic radiation having wavelengths at a selected wavelength or within a selected range of wavelengths in the ultraviolet to infrared spectrum (e.g., from about 200 nm to about 1400 nm; "UV-IR"), in some embodiments, less than 25% of a selected wavelength (or range) in the UV-IR spectrum, and in some embodiments, less than 10% of a selected wavelength (or range) in the UV-IR spectrum.

Various details of "substantially transparent" and "substantially non-transparent" materials are described in PCT Patent Publication No. WO 2011/063332, which is incorporated herein by reference in its entirety.

The terms "hydrophobic" and "hydrophilic" are generally used as commonly understood in the art. Thus, a "hydrophobic" material has relatively little or no affinity for water or aqueous media, while a "hydrophilic" material has relatively strong affinity for water or aqueous media. The required levels of hydrophobicity or hydrophilicity may vary depending on the nature of the sample, but may be readily adjusted based on simple empirical observations of a liquid sample when applied to various hydrophobic or hydrophilic surfaces.

In some embodiments, contact angle measurements (e.g., static and/or dynamic) can be used to characterize the hydrophobicity/hydrophilicity of a surface. Such surface characteristic may be attributable to the material makeup of the surface itself, which can be independent of the bulk material. That is, in some embodiments, even if the bulk material forming a structure is largely hydrophobic, the surface that will contact a sample can be modified to be hydrophilic so that aqueous samples, for example, will have a greater affinity for the modified surface. Exemplary static and dynamic contact angle measurement methods are described in Examples 10 and 11.

In some embodiments, the static water surface contact angle (e.g., static and/or dynamic) of at least an inner surface of the sample detection container, e.g., in which the microcavity of the present disclosure can be formed (e.g., which can be measured on the structured surface, or on a smooth unstructured surface of the same material), can be at least about 50 degrees, in some embodiments, at least about 65 degrees, in some embodiments, at least about 75 degrees, in some embodiments, at least about 85 degrees, in some embodiments, at least about 95 degrees, in some embodiments, at least about 100 degrees, and in some embodiments, at least about 130 degrees.

In some embodiments, the dynamic advancing surface contact angle of at least an inner surface of the sample detection container, e.g., in which the microcavity of the present disclosure can be formed (e.g., which can be measured on the structured surface, or on a smooth unstructured surface of the same material), can be at least about 50 degrees, in some embodiments, at least about 65 degrees, in some embodiments, at least about 75 degrees, in some embodiments, at least about 85 degrees, in some embodiments, at least about 95 degrees, in some embodiments, at least about 100 degrees, and in some embodiments, at least about 130 degrees.

In some embodiments, the dynamic receding surface contact angle of at least an inner surface of the sample detection container, e.g., in which the microcavity of the present disclosure can be formed (e.g., which can be measured on the structured surface, or on a smooth unstructured surface of the same material), can be at least about 25 degrees, in some embodiments, at least about 35 degrees, in some embodiments, at least about 45 degrees, in some embodiments, at least about 65 degrees, in some embodiments, at least about 75 degrees, in some embodiments, at least about 90 degrees, and in some embodiments, at least about 100 degrees.

In some embodiments, an inner surface of the sample detection container (e.g., an inner surface of a wall that is oriented at the effective angle, e.g., at various locations—see Example 12) can have a surface roughness that either does not impede collection of an analyte of interest in the microcavity or improves collection of an analyte of interest. In some embodiments, the surface roughness of the inner surface can be characterized by a roughness average (Ra) value of less than 1.5 microns, in some embodiments, less than 1 micron, in some embodiments, less than 750 nm (0.75 microns), in some embodiments, less than 500 nm (0.5 microns), and in some embodiments, less than 300 nm (0.3 microns).

In some embodiments, the surface roughness of the inner surface of the sample detection container can be characterized by a root mean square roughness (Rq) value of less than 1.5 microns, in some embodiments, less than 1 micron, and in some embodiments, less than 800 nm.

In some embodiments, systems and methods of the present disclosure can be used to determine the presence or absence of a microorganism of interest in a sample by interrogating the sample for the microorganism itself, or for an analyte of interest that is representative of the presence of the microorganism. For example, in some embodiments, the microorganisms themselves can be concentrated (e.g., sedimented into one or more microcavities by centrifugation) in the sample and then detected in the one or more microcavities, and in some embodiments, analytes that are representative of the presence of microorganisms can be concentrated (e.g., sedimented into one or more microcavities by centrifugation) in the sample and detected in the one or more microcavities. For example, in some embodiments, substrates can be added to the sample (e.g., β-galactosidase substrates, such as X-gal) that precipitate after cleavage by the appropriate enzyme. Such precipitated substrates can be concentrated (e.g., sedimented into one or more microcavities by centrifugation, along with the microorganisms/cells) and detected and/or quantified more quickly than they otherwise could be at a low concentration in a large volume sample.

Various examples of analytes are given above and in the Examples section, including indicator dyes. In some embodiments, such an indicator dye can include a precipitating dye and/or an internalized dye. In the case of precipitated dyes, often the dyes are small molecules that diffuse out of the cells and which may need sufficient incubation time to reach a detectable concentration, even when concentrated in one or more microcavities. However, in the case of internalized dyes, the cells (i.e., microorganisms) themselves can be 'marked' or stained by the dye, and detection (e.g., presence/absence and/or quantification) can occur as soon as the cells have been concentrated into the microcavity, for example, by viewing through the base of the microcavity.

Another specific example of detection that could be performed using the systems and methods of the present disclosure involves detecting (e.g., for presence/absence) microorganisms using chemiluminescence by concentrating the sample into the one or more microcavities and adding the reagents for performing ATP-based detection. The reagents can be added either before or after centrifugation, or by having the reagents coated and/or dried in microcavity. In such embodiments, the reagents can include a lysis reagent, luciferin (substrate) and luciferase (enzyme). The lysis reagent can be used to break open the cells to release ATP, which the luciferase needs to cause luciferin to chemiluminesce. As a result, a microcavity containing a microorganism of interest would be "marked" (e.g., would light up), whereas a microcavity not containing the microorganism would not be "marked" (e.g., would be dark), such that the presence/absence of the microorganisms can be detected indirectly.

Figure 2:
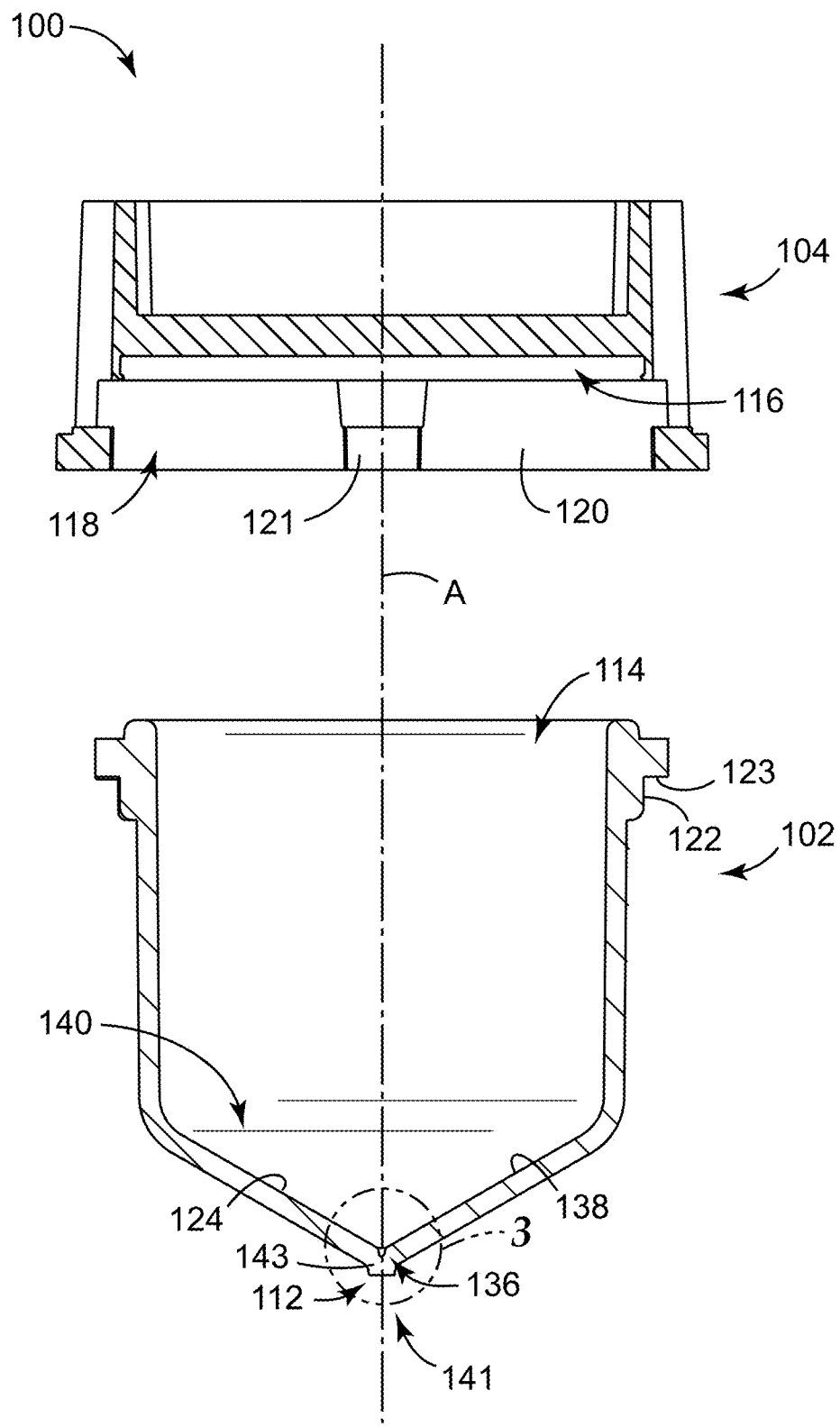
FIG. 2 is an exploded side cross-sectional view of the sample detection container of FIG. 1.
Figure 3:
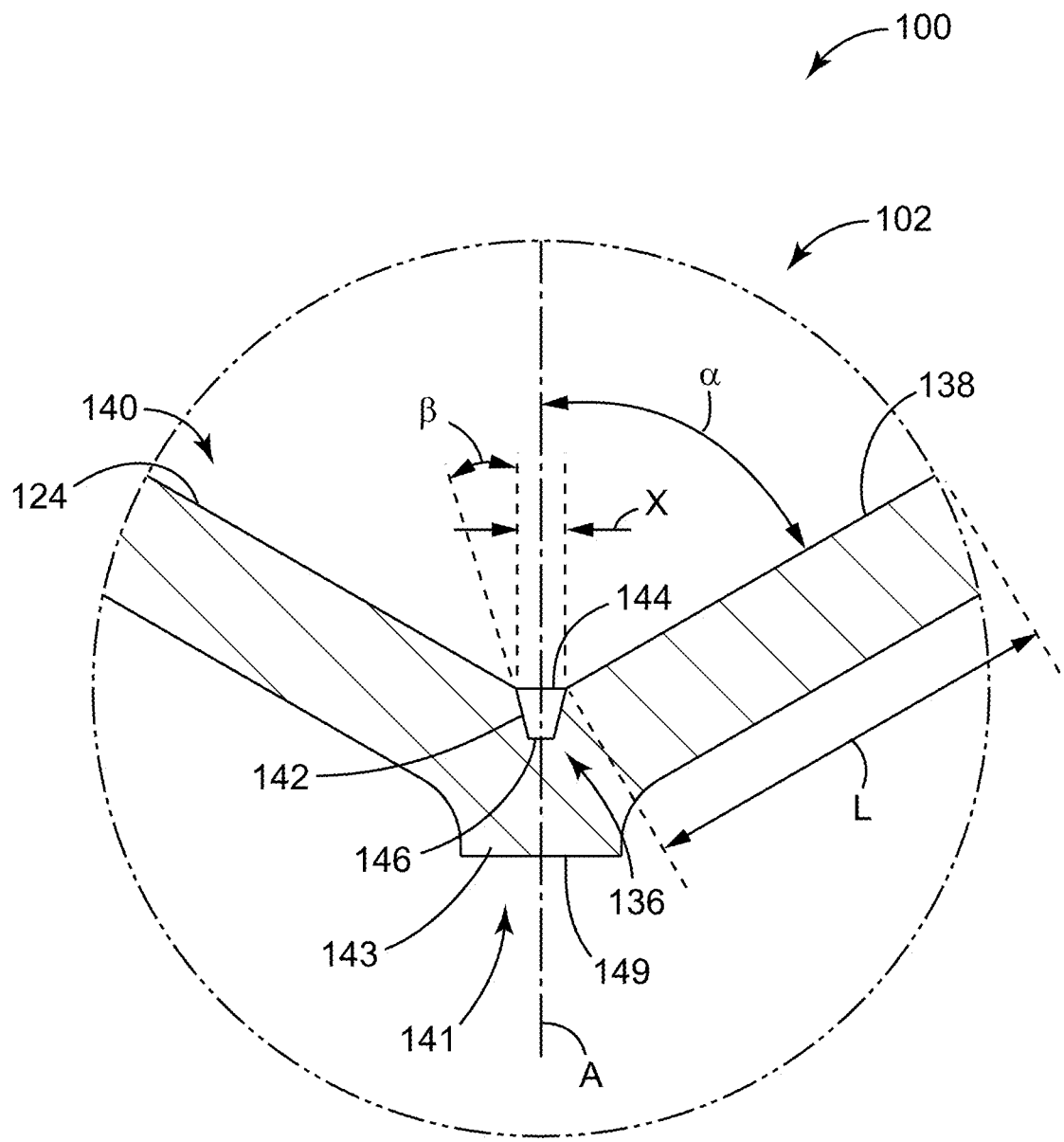
FIG. 3 is a close-up side cross-sectional view of the sample detection container of FIGS. 1 and 2.

FIG. 1 illustrates a sample detection system 100 according to one embodiment of the present disclosure. In some embodiments, the sample detection system 100 can be used to concentrate a sample to form a concentrate (e.g., in a microcavity 136, as shown in FIGS. 2 and 3 and described in greater detail below), and can be further used to interrogate the concentrate for an analyte of interest, that is, for detecting the presence or absence of an analyte of interest.

As shown in FIG. 1, in some embodiments, the sample detection system 100 can include a sample detection container 102. The sample detection container 102 can be configured to be closed by a cap 104, such that the sample detection container 102 and the cap 104 can be removably or permanently coupled together.

The sample detection container 102 can be adapted to contain a sample that is to be analyzed, for example, for one or more analytes of interest. The sample is generally a liquid sample, in some embodiments, is a dilute liquid sample (i.e., any analyte of interest present in the sample is present at a low concentration), and in some embodiments, is a dilute aqueous sample. The sample detection container 102 can be sized and shaped, as desired, to accommodate the sample to be analyzed, and the shape and configuration of the sample detection container 102 and the cap 104 is shown by way of example only.

As shown in FIG. 1, the sample detection container 102 can be an elongated tube having a closed end or base 112 (e.g., a tapered closed end 112) and an open end 114, and the cap 104 can include a closed end or base 116 and an open end 118. The open end 118 of the cap 104 can be dimensioned to receive at least a portion of the sample detection container 102, and particularly, the open end 114 of the sample detection container 102, such that coupling the cap 104 and the sample detection container 102 together closes and/or covers the open end 114 of the sample detection container 102.

In general, a sample detection method can be performed using the sample detection system 100 of FIG. 1 as follows: a sample can be placed in the sample detection container 102, and the cap 104 can be coupled to the sample detection container 102 to close the sample detection container 102. The closed or capped sample detection container 102 can then be centrifuged toward the closed end 112 of the sample detection container 102 to form a concentrate of the sample in the sample detection container 102, e.g., that is retained in the microcavity 136, and a supernatant, e.g., a bulk supernatant which will be located above the microcavity 136. A separation liquid of the present disclosure can then be added to the sample detection container 102 that is configured to move between the microcavity 136 and the bulk supernatant to isolate the concentrate in the microcavity 136 from the remainder of the sample. The concentrate can then be interrogated for an analyte of interest while being retained in the sample detection container 102. As a result, in some embodiments, the "concentrate" (i.e., a higher-concentration portion of the sample) can also be referred to as a "retentate." In some embodiments, the concentrate can be interrogated by inverting sample detection container 102 to drain the supernatant of the sample resulting from centrifugation and the separation liquid, away from the microcavity 136, and interrogating the concentrate in the microcavity 136, e.g., via the closed end 112 of the sample detection container 102.

An exemplary sample detection method employing the sample detection container 102 will be described in greater detail below with reference to FIG. 4.

By way of further example, the cap 104 includes an inner surface 120 that includes one or more protrusions 121, and the sample detection container 102 includes an outer surface 122 that includes one or more tracks or threads 123 adjacent the open end 114. The protrusions 121 of the cap 104 are configured to cooperate and engage with the threads 123 of the sample detection container 102, such that the cap 104 and the sample detection container 102 can be coupled together.

The specific style of protrusions 121 and threads 123 shown in FIG. 1 includes a series of circumferentially-spaced protrusions 121 and threads 123 so that any protrusion 121 on the cap 104 can be coupled to any thread 123 on the sample detection container 102 and turned from an unlocked to a locked position by rotating the cap 104 and the sample detection container 102 relative to one another (e.g., 90 degrees, if 4 sets of protrusions 121/threads 123 are employed and evenly spaced about the inner surface 120 of the cap 104 and the outer surface 122 of the sample detection container 102). The illustrated coupling mechanism between the sample detection container 102 and the cap 104 is shown by way of example only as an efficient means for closing the sample detection container 102.

In some embodiments, the sample detection container 102 and the cap 104 can be coupled together in such a way that the interior of the sample detection system 100 is sealed from ambience (e.g., forming a liquid-tight seal, a hermetic seal, or a combination thereof). For example, in some embodiments, one or more seals (e.g., o-rings) can be employed between the sample detection container 102 and the cap 104, or one or both of the sample detection container 102 and the cap 104 can include one or more seals (e.g., o-rings).

The sample detection container 102 and the cap 104 can be formed of a variety of materials, including, but not limited to, polymeric materials, metals (e.g., aluminum, stainless steel, etc.), ceramics, glasses, and combinations thereof. Examples of polymeric materials can include, but are not limited to, polyolefins (e.g., polyethylene, polypropylene, combinations thereof, etc.), polycarbonate, acrylics, polystyrene, high density polyethylene (HDPE), polypropylene, other suitable polymeric materials capable of forming a self-supporting container, or a combination thereof. The term "self-supporting" is generally used to refer to an object that does not collapse or deform under its own weight. For example, a bag is not "self-supporting" in that it does not maintain its shape, but rather collapses or distorts, under its own weight. The sample detection container 102 and the cap 104 can be formed of the same or different materials.

The sample detection container 102 and the cap 104, or a portion thereof, can be substantially transparent, opaque (i.e., substantially non-transparent), or somewhere in between (e.g., translucent), and can be any suitable size, depending on the type, amount and/or size of sample to be analyzed, and the type, amount and/or size of concentrate to be collected and interrogated. The sample detection container 102 or at least the portion adjacent the microcavity 136 is preferably substantially transparent. In some embodiments, the sample detection container 102 can have a capacity of at least about 1 mL, at least about 5 mL, at least about 10 mL, at least about 25 mL, at least about 50 mL, at least about 100 mL, or at least about 250 mL. That is, in some embodiments, the capacity, or volume, of the sample detection container 102 can range from about 1 mL to about 250 mL, and in some embodiments, can range from about 1 mL to about 100 mL.

The shapes, dimensions and coupling means for the sample detection container 102 and the cap 104 are described above and illustrated in FIG. 1 by way of example only. It should be understood, however, that a variety of shapes and dimensions of the sample detection container 102 and the cap 104 can be used. In addition, a variety of coupling means can be employed to removably and/or permanently couple the sample detection container 102 and the cap 104, including, but not limited to, screw threads (as shown or otherwise), a clamp (e.g., a spring-loaded clamp, a snap-type clamp, etc.); a clip (e.g., a spring-loaded clip, etc.); ties (e.g., wire ties); one or more magnets; tape; an adhesive; a cohesive; snap-fit engagement (e.g., wherein the cap 104 functions as a flip-top cap); press-fit engagement (also sometimes referred to as "friction-fit engagement" or "interference-fit engagement"); thermal bonding (e.g., heat and/or pressure applied to one or both of the components to be coupled); welding (e.g., sonic (e.g., ultrasonic) welding); other suitable coupling means; and combinations thereof.

As shown in FIGS. 2 and 3, the closed end 112 of the sample detection container 102 can include (i.e., terminate in) one or more microcavities 136 adapted to retain a concentrate of the sample to be analyzed, the microcavity 136 opening toward the open end 114 of the sample detection container 102. The microcavity 136 can include at least one of a well, a depression, a recess, and the like, and combinations thereof, such that the microcavity 136 defines an internal volume (e.g., microvolume or less) configured to retain a concentrate of the sample. In some embodiments, as shown in the embodiment illustrated in FIGS. 1-3, 4 and 5, the sample detection container 102 can include a single microcavity 136. In some embodiments, the sample detection container 102 can include a plurality of microcavities 136. In some embodiments, the number of microcavities 136 can be minimized to minimize the total volume in which a concentrate of the sample can be retained, thereby maximizing the concentration of an analyte of interest in the retained sample concentrate, if present.

In some embodiments, the sample detection container 102 can include one or more protrusions 143 that surrounds the microcavity 136. Such a protrusion or support structure 143 can support the microcavity (or microcavities) 136 during formation and use, particularly when a single microcavity or a few microcavities are employed.

In some embodiments, a large number of microcavities 136 can be employed, for example, to increase the probability that only one analyte of interest (e.g., 1 colony-forming unit (cfu) of a bacterium of interest) will end up in one given microcavity 136. Such a configuration can be particularly useful for quantifying the number of analytes of interest that are present in a given sample. The many microcavities can then be scanned, for example, to determine whether the analyte of interest is present, while also characterizing the amount of the analyte that is present. However, the present inventors discovered that if a maximum of one (or a relatively small amount) of an analyte of interest is present in one given microcavity 136, the concentration in that one microcavity 136 may be relatively low, resulting in a longer detection time for that sample. For example, if a sample included 10 cfu of a bacterium of interest, and each of the 10 cfu ended up in a separate microcavity 136, it would take longer to detect their presence than if all 10 cfu ended up in the same microcavity 136.

As a result, the present inventors discovered that if the number of microcavities can be minimized, then all of the analyte(s) of interest that may be present in a sample will be more likely to be concentrated together in a smaller number of microcavities 136, in a smaller total or overall volume, resulting in a higher concentration, and the detection time can be reduced even further. Prior teachings, however, taught away from such a construction because minimizing the number of microcavities diminishes or eliminates (i.e., sacrifices) the ability to quantify the analyte of interest. However, the detection time to determine presence or absence of an analyte of interest can be greatly reduced. For this reason, particular advantages can be achieved with a single microcavity 136, e.g., if quantification of the analyte of interest is not particularly desired. In cases where quantification is necessary, sample detection containers of the present disclosure can include a plurality of microcavities to facilitate quantification.

As a result, in some embodiments, the sample detection container 102 can include no greater than 10 microcavities, in some embodiments, no greater than 8 microcavities, in some embodiments, no greater than 5 microcavities, in some embodiments, no greater than 4 microcavities, in some embodiments, no greater than 3 microcavities, in some embodiments, no greater than 2 microcavities, and in some embodiments, no greater than 1 microcavity. For simplicity, the microcavity 136 of FIGS. 1-3, 4 and 5 will be described as a singular microcavity, however, it should be understood that the same description can apply to more microcavities 136 if more than one microcavity is employed.

Figure 3A:
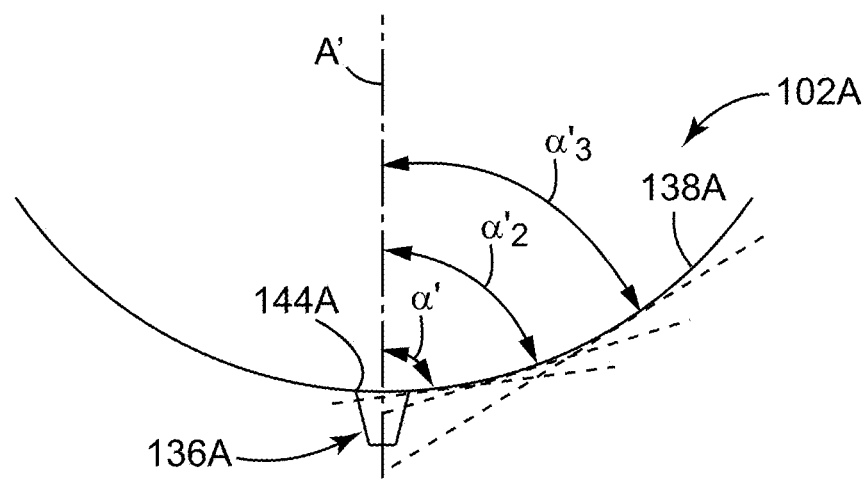
FIGS. 3A-3C are each a close-up side cross-sectional view of the sample detection container according to another embodiment of the present disclosure.
Figure 3B:
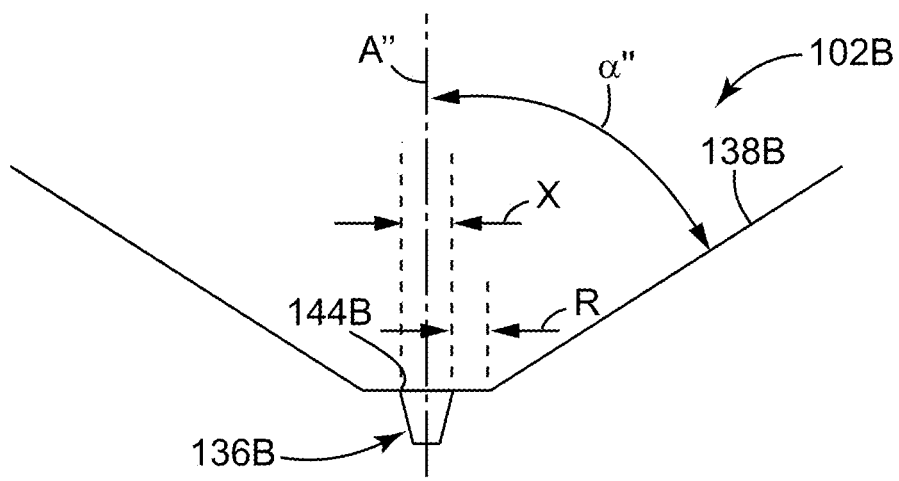
Figure 3C:
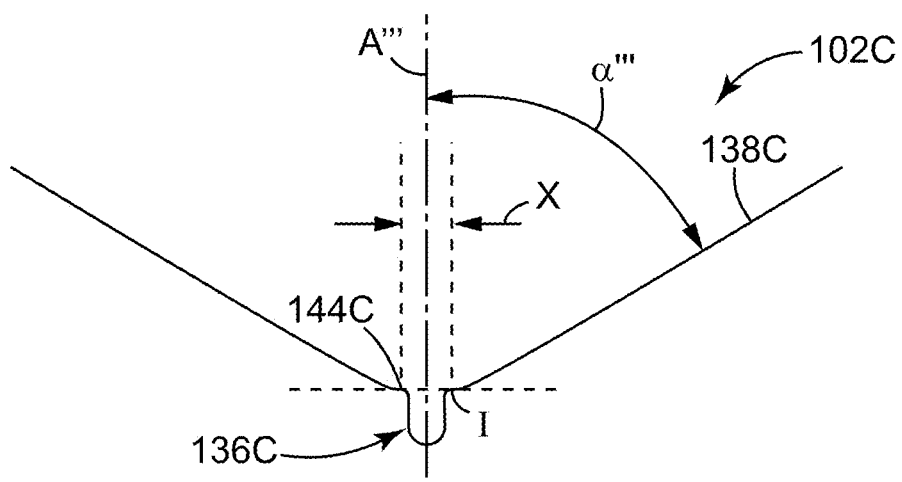

As shown in FIG. 3, in some embodiments, the microcavity 136 can include an open end (opening or top opening) 144, one or more sidewalls 142, a base 146, and a longitudinal axis A. As shown in FIGS. 1 and 2, the longitudinal axis A of the microcavity 136 can also be the longitudinal axis A of the sample detection container 102 and the sample detection system 100. In some embodiments, as shown, the microcavity 136, the sample detection container 102, and the cap 104 can be centered about the longitudinal axis A. The longitudinal axis A is generally normal to (i.e., oriented orthogonally with respect to) a transverse cross-section of the microcavity 136, and can pass through the top opening 144 and the base 146 of the microcavity 136. Such a transverse cross-section of the microcavity 136 can be taken anywhere along the height of the microcavity 136 between its top opening 144 and its base 146. The longitudinal axis A can also be referred to as a vertical axis, or a nominal centrifugation/sedimentation axis, i.e., an axis along which a sample positioned in the sample detection container 102 would be subjected to centrifugal forces upon centrifugation, disregarding known effects of small-radius (e.g., lab-bench) centrifuges. Other possible shapes and configurations of microcavities 136 are shown in FIGS. 3A-3C and described in greater detail below.

The microcavity 136 is shown in FIG. 3 as having a generally trapezoidal cross-sectional shape (i.e., a frusto-conical three-dimensional shape). It should be understood that the microcavity 136 can include a variety of shapes, as long as the microcavity 136 is shape to be able to retain a concentrate of the sample. Said another way, each recess 136 can be shaped and dimensioned to provide a reservoir, or well, for the concentrate of the sample. Generally, the microcavity 136 is configured (e.g., shaped and sized) to retain the concentrate 154 in the microcavity 136 when sample detection container 102 is in any orientation (e.g., by capillary forces).

Whether the microcavity 136 includes a well, depression, or a combination thereof, examples of suitable recess shapes can include, but are not limited to, a variety of polyhedral shapes, parallelepipeds, prismatoids, prismoids, etc., and combinations thereof. For example, the microcavity 136 can be polyhedral, conical, frusto-conical, pyramidal, frusto-pyramidal, spherical, partially spherical, hemispherical, ellipsoidal, dome-shaped, cylindrical, cube-corner shaped, other suitable shapes, and combinations thereof. Furthermore, the microcavity 136 can have a variety of cross-sectional shapes (including a vertical cross-section as shown in FIG. 3, a horizontal cross-section, or a combination thereof), including, but not limited to, at least one of parallelograms, parallelograms with rounded corners, rectangles, squares, circles, half-circles, ellipses, half-ellipses, triangles, trapezoids, stars, other polygons, other suitable cross-sectional shapes, and combinations thereof.

As shown in FIGS. 1-3, the sample detection container 102 can further include a wall 138 (i.e., an internal wall) that defines at least a portion of an inner surface of the sample detection container 102. The wall 138 extends to (e.g., tapers toward) the microcavity 136, and at least a portion of the wall 138 is located adjacent the top opening 144 of the microcavity 136. In general the phrase "located adjacent the top opening of the microcavity" refers to the wall 138 (or a portion thereof) extending right up to the top opening 144 of the microcavity 136 (as shown), or to a location that is less than 1 time (ideally, less than 0.5×, or less than 0.25×) a transverse dimension—i.e., a representative x,y dimension, as described above—of the microcavity 136. In some embodiments, the representative transverse dimension can be the transverse dimension of the microcavity 136 at its top opening 144.

At least a portion of the wall 138 is sloped toward the microcavity 136 and has a slope that is oriented at an effective angle α with respect to the longitudinal axis A of the microcavity 136. The effective angle α can be generally range from 0 degrees to 90 degrees. As described above, the upper limit of 90 degrees can facilitate collection of any analytes of interest in the microcavity 136. That is, the effective angle α can be configured to maximize the collection and sedimentation of the sample into the microcavity 136, such that under centrifugation, the analyte of interest (e.g., a microorganism) will be directed into the microcavity 136. Effective angles α of 45 degrees and 60 degrees were tested with systems and methods of the present disclosure, as exemplified in the Examples. However, the present inventors found that the performance of the systems and methods of the present disclosure employing the separation liquid was not dependent on effective angle.

The wall 138, and particularly, the effective angle α thereof, can facilitate collection of the analyte of interest in the microcavity 136 and the resulting concentration of the analyte of interest in the microcavity 136. In some embodiments, the wall 138 (e.g., the area of the wall 138) can be significantly large, relative to the microcavity 136 (e.g., relative to the area of the opening to the microcavity 136). As a result, at least the portion of the wall 138 that is oriented at the effective angle α (and located adjacent the microcavity 136) can have a length (see, e.g., length L in FIG. 3) that is at least 5 times a representative dimension (e.g., oriented orthogonally with respect to the longitudinal axis A) of the microcavity 136. For example, in some embodiments, the wall 138 (or the pertinent portion thereof oriented at the effective angle α) can have a length 5 times a transverse dimension, e.g., at its top opening 144. FIG. 3 illustrates a transverse dimension X at the top opening 144 of the microcavity 136. As further shown in FIG. 3, the length L of the portion of the wall 138 that is shown clearly has a length of at least 5×.

In some embodiments, the wall 138 can have a length of at least 10×, in some embodiments, at least 15×, in some embodiments, at least 20×, in some embodiments, at least 50×, in some embodiments, at least 100×, in some embodiments, at least 200×, in some embodiments, at least 500×, and in some embodiments, at least 1000×.

The top opening transverse (i.e., x,y) dimension is generally used in the present disclosure as the representative transverse dimension because this is the location of the interface between the wall 138 and the microcavity 136. However, other dimensions could be used as the representative dimension, as long as the representative dimension is indicative of the order of magnitude of the microcavity 136, relative to the wall length. For example, in some embodiments, the base 146 of the microcavity 136 can be used (e.g., if a flat base is employed), or an average transverse dimension taken over the height of the microcavity 136, etc.

In some embodiments, as shown in FIG. 3, the microcavity 136 can include a draft angle β, such that the one or more sidewalls 142 of the microcavity 136 are oriented at a non-zero and non-right angle with respect to the respective base(s) 146. In some embodiments, the draft angle β can be reported as the angle between a sidewall 142 of the microcavity 136 and a vertical (i.e., a line or plane that is perpendicular or normal to a flat base 146). In some embodiments, the draft angle β can be at least about 5 degrees, in some embodiments, at least about 10 degrees, in some embodiments, at least about 12.5 degrees, and in some embodiments, at least about 15 degrees. In some embodiments, the draft angle β is no greater than about 50 degrees, in some embodiments, no greater than about 30 degrees, in some embodiments, no greater than about 25 degrees, and in some embodiments, no greater than about 20 degrees. In some embodiments, the draft angle β ranges from about 10 degrees to about 15 degrees. In some embodiments, the draft angle β is 14 degrees.

In the embodiment illustrated in FIG. 3, the base 146 of the microcavity 136 is flat and planar (i.e., has an area), and is oriented substantially orthogonally with respect to the longitudinal axis A. However, because other shapes of the microcavity 136 are possible, the base 146 need not be planar, but rather can include a point or a line that is spaced the greatest distance from the top opening 144. In addition, even in embodiments employing a planar base 146, the base 146 need not be entirely flat, but rather can be at least partially curved, flat, or a combination thereof. Furthermore, even in embodiments employing a flat, planar base 146, the base 146 need not be orthogonal to the longitudinal axis A.

Furthermore, in the embodiment illustrated in FIG. 3, the microcavity 136 is shown as having various lines of symmetry, and the base 146 is centered with respect to the opening 144. However, it should be understood that the microcavity 136 need not include any lines of symmetry, and the base 146 (whether the base 146 includes a point, a line or an area) need not be centered with respect to the opening 144 of the microcavity 136.

If more than one microcavity 136 is employed, the microcavities 136 can have the same size and shape; however, it should be understood that all of the microcavities 136 do not need to be of the same size or shape. That is, the microcavities 136 can all be formed of about the same shape and size, the same or similar shape but different sizes, different shapes but similar sizes, different shapes and sizes, or a combination thereof.

FIGS. 3A-3C illustrate close-up views of sample detection containers 102A, 102B and 102C according to additional embodiments of the present disclosure. Each sample detection container 102A, 102B, 102C includes a microcavity 136A, 136B, 136C, a longitudinal axis A', A'', A''', and a wall 138A, 138B, 138C oriented at an effective angle α', α'', α''', respectively.

FIG. 3A illustrates sample detection container 102A in which the wall 138A is curved and therefore includes multiple slopes. For example, effective angles $\alpha'$, $\alpha_2'$ and $\alpha_3'$ are shown for illustration purposes. However, the portion of the wall 138A located adjacent the microcavity 136A is at least 5× the transverse dimension of a top opening 144A of the microcavity 136A, and the multiple slopes (i.e., the multiple effective angles α', α'', and α''') of the curved wall 138A are each greater than 45 degrees and less than 90 degrees. FIG. 3A therefore represents that a "wall" of a sample detection container according to the present disclosure can be curved or include multiple slopes.

FIG. 3B illustrates a sample detection container 102B (or wall 138) that includes a flat region (i.e., oriented at 90 degrees with respect to the longitudinal axis A'') located between the wall 138 (or the portion thereof oriented at the effective angle α″) and the microcavity 136. However, the flat region is not substantial in size, relative to the microcavity 136 or the wall 138 and has a length R that is less than 1 times the transverse dimension X of the microcavity 136B at its top opening 144B; in some embodiments, less than 0.5×, and in some embodiments, less than 0.25×. Other than the flat region, the sample detection container 102 is substantially the same as that of the sample detection container 102 of FIGS. 1-3.

FIG. 3C illustrates a microcavity 136C with a rounded bottom and a rounded top opening. An inflection point I defines where the microcavity 136C meets the wall 138C, or the portion thereof, e.g., that is oriented at the effective angle α‴. As shown, in some embodiments, the inflection point I can define the top opening 144C of the microcavity 136C, so that in such embodiments, the transverse dimension X of the microcavity 136C can be taken at the height of the inflection point I. Such a curved upper surface to the microcavity 136C can result from a molding artifact. However, generally if a wall of the sample detection container of the present disclosure is described as being oriented at an effective angle α, such a "wall" (e.g., wall 138C) of the present disclosure is substantial enough in size, relative to the microcavity 136, that the wall 136C is not merely a molding artifact.

With continued reference to the embodiment of FIGS. 1-3, in some embodiments, the microcavity 136 (e.g., relative to the rest of the sample detection container 102), can include a surface modification (e.g., such as a hydrophilic/oleophilic surface treatment or coating) to facilitate retaining a concentrate of interest.

In some embodiments, as shown, the sample detection container 102 can be described as including the microcavity 136 in a first side 140 of the sample detection container 102 that generally faces the interior (or "inside") of the sample detection container 102, and that generally includes an inner surface 124 of the sample detection container 102, or a portion thereof. Particularly, the first side 140 can include the inner surface 124 in which the microcavity 136 can be formed, such that the top opening 144 of the microcavity 136 opens toward the first side 140 of the sample detection container 102, and toward the interior of the sample detection container 102. The sample detection container 102 can further include a second side 141 having an outer surface 149 (see, e.g., FIG. 3) that is generally opposite the first side 140 and the inner surface 124, respectively. The second side 141 can face outside of the sample detection container 102, for example, away from the sample detection container 102. As a result, the concentrate retained in the sample detection container 102 (i.e., in the microcavity 136) can be interrogated from the second side 141, for example in embodiments in which at least a portion of the sample detection container 102 (e.g., the closed end or base 112 and/or the second side 141) is substantially transparent.

As mentioned above, in some embodiments, the volume of the sample detection container 102 (i.e., the capacity of the sample detection container 102) can range from about 1 mL to about 250 mL. As a result, in some embodiments, the volume of the sample can be at least about 1 mL, in some embodiments, at least about 10 mL, and in some embodiments, at least about 100 mL. In some embodiments, the volume of the sample is no greater than about 200 mL, in some embodiments, no greater than about 100 mL, in some embodiments, no greater than about 75 mL, and in some embodiments, no greater than about 50 mL. In some embodiments, the volume of the sample ranges from about 1 mL to about 100 mL.

In some embodiments, the sample detection container 102 has a capacity to retain a volume of concentrate of, and/or a plurality of microcavities 136 (or microcavity surface), if employed, includes a collective volume of at least about 1 microliter (μL), in some embodiments, at least about 5 μL, in some embodiments, at least about 10 μL, and in some embodiments, at least about 25 μL. In some embodiments, the sample detection container 102 has a capacity to retain a volume of concentrate of, and/or a plurality of microcavities 136 (or microcavity surface) includes a collective volume of, no greater than 200 μL, in some embodiments, no greater than about 100 μL, in some embodiments, no greater than about 75 μL, and in some embodiments, no greater than about 50 μL. In some embodiments, the sample detection container 102 has a capacity to retain a volume of concentrate of, and/or a plurality of microcavities 136 (or microcavity surface) includes a collective volume that ranges from about 1 μL to about 100 μL. In some embodiments, these volumes can be reported as volume per unit area (e.g., μL per $cm^2$), so that the collective volume of the microcavity surface can be independent of the overall dimensions of the sample detection container 102.

In some embodiments, the ratio of the volume of the sample detection container 102 (or a "receptacle" portion of the container 108) to the volume of the concentrate (or retentate) of the sample that is retained in the microcavity 136 is at least about 100:1 ($10^2$:1), in some embodiments, at least about 1000:1 ($10^3$:1), in some embodiments, at least about 10,000:1 ($10^4$:1), in some embodiments, at least about 100,000:1 ($10^5$:1); in some embodiments, at least about $10^8$:1; in some embodiments, at least about $10^9$:1; in some embodiments, at least about $10^{10}$:1, and in some embodiments, at least about $10^{11}$:1. In some embodiments, the ratio of the volume of the sample detection container 102 to the volume of the concentrate in the microcavity 136 ranges from about 100:1 to about $10^{11}$:1.

In some embodiments, the concentration increase (i.e., the concentration (e.g., of the more dense matter, such as the analyte(s) of interest) of the resulting concentrate retained in the microcavity 136, divided by the concentration of the initial sample, expressed as a ratio) can be at least about 100:1 ($10^2$:1), in some embodiments, at least about 1000:1 ($10^3$:1), in some embodiments, at least about 10,000:1 ($10^4$:1), and in some embodiments, at least about 100,000:1 ($10^5$:1). In some embodiments, the concentration efficiency ranges from about 10:1 to about $10^5$:1.

Figure 4:
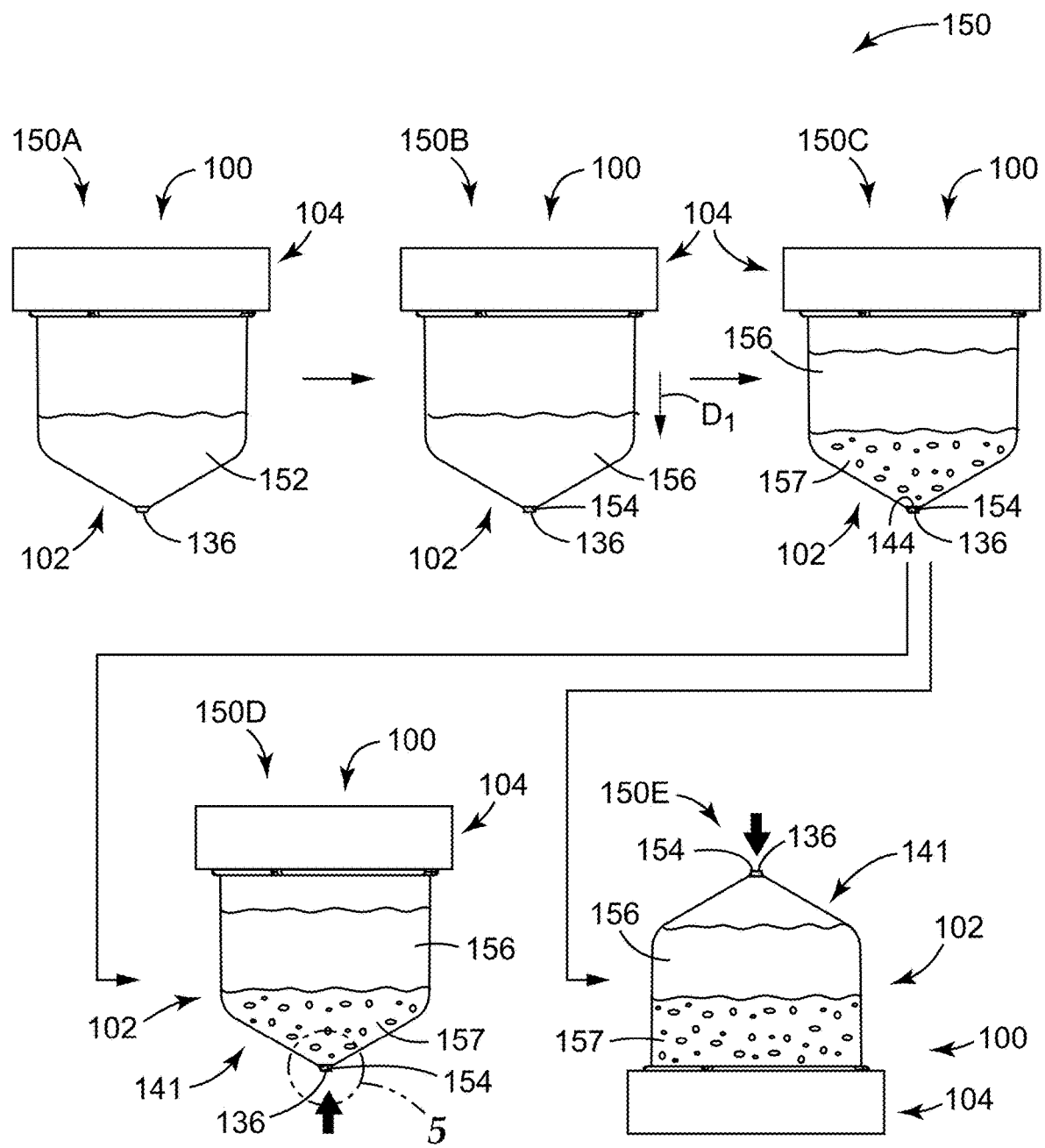
FIG. 4 illustrates a sample detection method according to one embodiment of the present disclosure, showing side elevational views of the sample detection container of FIGS. 1-3.

With reference to FIG. 4, a sample detection method 150 will now be described, with continued reference to the sample detection system 100 of FIGS. 1-3, with the microcavity 136 shown schematically for illustration purposes.

As shown in FIG. 4, in a first step 150A, a sample 152 can be positioned in the sample detection and the cap 104 can be coupled to the sample detection container 102 to close the sample detection container 102. As shown in a second step 150B, the sample detection system 100 (i.e., the sample detection container 102) can be centrifuged in a first direction (or orientation) $D_1$ toward the microcavity 136. Such a centrifugation process can form a concentrate 154 of the sample 152 and a supernatant 156, and can cause the concentrate 154 (see FIG. 5) comprising the more dense matter of the sample 152 to be moved into the microcavity 136. The "concentrate" 154 can generally include a sediment of the sample that is formed as a result of the centrifugation process, but can also include at least some of the supernatant, or diluent, of the sample, as will be described in greater detail below with reference to FIG. 5.

In the centrifugation step shown in step 150B of FIG. 4, the centrifugation g-force, duration and/or number of cycles necessary to form and retain the concentrate 154 in the microcavity 136 can vary depending on one or more of the composition of the sample 152, the analyte(s) of interest, and the like. In some embodiments, the amount of g-force required to concentrate the analyte(s) of interest can depend on the size and density of the analyte, the density and viscosity of the diluent, and the volume of sample 152 in the sample detection container 102 (i.e. the height of the sample 152 in the sample detection container 102 defines the distance the analyte needs to migrate under a specified g-force to reach the microcavity 136). The sedimentation velocity (V, in centimeters per second (cm/s)) can be approximated using Equation 1:

$$V=2ga^2(\rho 1-\rho 2)/9\eta \tag{1}$$

where g=acceleration in cm/s² (i.e., g-force in gs*980 cm/s²), ρ1=analyte density in g/cm³, ρ2=density of sample media (e.g., diluent) in g/cm³, η=coefficient of viscosity in poises (g/cm/s), and a=analyte radius in centimeters (assuming a spherical shape). In some centrifuges, the g-force can be determined by the rotational speed (e.g., in revolutions per minute (RPM)) and the distance of the sample from the center of the rotor (i.e. the sample experiences a higher g-force at the same rotational speed if it is placed further away from the rotor). As a result, in order to collect the analyte(s) of interest that may reside in the sample 152 furthest from the microcavity 136, the distance between the center of the rotor and the height of the sample 152 positioned closest to the rotor can be calculated to estimate what the g-force would need to be to move the analyte(s) of interest the furthest distance in the sample 152 to maximize collection of the analyte(s) of interest.

The sedimentation velocity can be calculated using the above equation, and then the centrifugation time (i.e., duration) can be calculated by dividing the distance (e.g., the maximum distance) the analyte(s) of interest, if present, would need to travel, by the sedimentation velocity. Alternatively, the desired time and distance can be used to estimate a sedimentation velocity, and the necessary g-force can then be calculated using Equation 1.

In some embodiments, the g-force in the centrifugation step can be at least about 500·g (e.g., 500*9.8 m/s² on earth, at sea level), in some embodiments, at least about 1000·g, and in some embodiments, at least about 5000·g. In some embodiments, the g-force in the centrifugation step can be no greater than about 100,000·g, in some embodiments, no greater than about 50,000·g, and in some embodiments, no greater than about 10,000·g.

In some embodiments, the duration of the centrifugation step can be at least about 1 minute, in some embodiments, at least about 5 minutes, and in some embodiments, at least about 10 minutes. In some embodiments, the duration of the centrifugation step can be no greater than about 120 minutes, in some embodiments, no greater than about 60 minutes, and in some embodiments, no greater than about 20 minutes.

As shown in step 150C of FIG. 4, one or more separation liquids 157 can then be added to the sample detection container 102. For example, the cap 104 can be temporarily removed from the sample detection container 102 to add the separation liquid 157, and then the sample detection system 100 can be reclosed by coupling the cap 104 to the sample detection container 102.

As shown in step 150C of FIG. 4, the separation liquid 157 effectively displaces the supernatant 156 located outside of the microcavity 136 (i.e., located above the top opening 144 of the microcavity 136) from the microcavity 136, such that a concentrate 154 of the sample 152 is retained and separated in the microcavity 136. That is, separation liquid 157 moves between the concentrate 154 of the sample 152 located in the microcavity 136 and a remainder of the sample in the sample detection container 102, such that the separation liquid 157 effectively isolates the concentrate 154 contained in the microcavity 136 from a bulk supernatant 156 of the sample 152.

As a result, at the step 150C of the method 150 of FIG. 4, the separation liquid 157 is located in the sample detection container 102 above the microcavity 136. The ability of the separation liquid 157 to effectively isolate the concentrate 154 from the bulk supernatant 156 without disrupting the concentrate 154 in the microcavity 136 was surprising. That is, the present inventors discovered separation liquids 157 that could be used to isolate the concentrate 154 in the microcavity 136 from the supernatant 156, while preserving the ability of the microcavity 136 to retain the concentrate 154—i.e., without increasing the volume of the concentrate 154, which would cause a decrease in the concentration of an analyte of interest and an increase in detection time. In addition, because the separation liquid 157 can effectively isolate the concentrate 154, the supernatant 156 and the separation liquid 157 need not be removed from the sample detection container 102 or physically drawn away from the microcavity 136 (e.g., by inverting the sample detection container 102. Such removal of the supernatant 156 and/or the separation liquid 157 is still possible but is not required for rapid detection of an analyte of interest in the microcavity 136.

The ability of the separation liquid 157 to effectively isolate the concentrate 154 from the bulk supernatant 156 can be at least partially attributed to the separation liquid 157 having a density sufficient to cause the separation liquid 157 to move down to the bottom of the sample detection container 102, i.e., toward the microcavity 136, to displace the supernatant 156, as well having a sufficient interfacial tension (i.e., liquid-liquid interfacial tension) with the sample 152, and particularly, with the supernatant 156 of the sample 152. The ability of the separation liquid 157 to isolate the concentrate 154 in the microcavity 136 without disrupting the concentrate 154 can also be at least partially attributed to the interfacial tension between the separation liquid 157 and the sample 152 (i.e., the supernatant 156).

A sufficient interfacial tension between the separation liquid 157 and the sample 152 (i.e., the supernatant 156) can ensure proper separation between the separation liquid 157 and the supernatant 156, both at the location of the microcavity 136 and in the bulk liquid above the microcavity 136. Said another way, a sufficient interfacial tension between the separation liquid 157 and the sample 152 (i.e., the supernatant 156) can ensure proper separation of the concentrate 154 in the microcavity 136 from the bulk liquid (i.e., supernatant 156) above the microcavity 136.

Particularly, the separation liquid 157 can have a density that is greater than that of the supernatant 156 of the sample 152 (i.e., the bulk supernatant located outside of the microcavity 136). In some embodiments, the separation liquid 157 can have a density that is greater than water (e.g., for aqueous samples), and particularly, the separation liquid 157 can have a density of at least 1.2 g/ml (or g/cm³). In some embodiments, the separation liquid 157 can have a density of at least 1.3 g/ml, in some embodiments, at least 1.4 g/ml, in some embodiments, at least 1.5 g/ml, in some embodiments, at least 1.6 g/ml, in some embodiments, at least 1.7 g/ml, in some embodiments, at least 1.8 g/ml, in some embodiments, at least 1.9 g/ml, and in some embodiments, at least 2.0 g/ml. In some embodiments, the separation liquid 157 can have a density that is no greater than 3.0 g/ml, in some embodiments, no greater than 2.8 g/ml, in some embodiments, no greater than 2.5 g/ml, in some embodiments, no greater than 2.3 g/ml, and in some embodiments, no greater than 2.0 g/ml. In some embodiments, the separation liquid 157 can have a density that ranges from 1.2 g/ml to 1.94 g/ml. In some embodiments, the separation liquid 157 can have a density that ranges from 1.4 g/ml to 1.94 g/ml.

Said another way, in some embodiments, the separation liquid 157 can have a density that is at least 0.2 g/ml greater than that of the sample 152 (i.e., the supernatant 156); in some embodiments, at least 0.3 g/ml greater; in some embodiments, at least 0.4 g/ml greater; in some embodiments, at least 0.5 g/ml greater; in some embodiments, at least 0.6 g/ml greater; in some embodiments, at least 0.7 g/ml greater; in some embodiments, at least 0.8 g/ml greater; in some embodiments, at least 0.9 g/ml greater; and in some embodiments, at least 1.0 g/ml greater. In some embodiments, the separation liquid 157 can have a density that is no greater than 2.0 g/ml greater than that of the sample 152 (i.e., the supernatant 156); in some embodiments, no greater than 1.8 g/ml greater; in some embodiments, no greater than 1.5 g/ml greater; in some embodiments, no greater than 1.3 g/ml greater; and in some embodiments, no greater than 1.0 g/ml greater. In some embodiments, the separation liquid 157 can have a density that ranges from 0.2 g/ml to 0.94 g/ml greater than that of the sample 152 (i.e., the supernatant 156). In some embodiments, the separation liquid 157 can have a density that ranges from 0.4 g/ml to 0.94 g/ml greater than that of the sample 152 (i.e., the supernatant 156).

In the case of an aqueous sample 152, the separation liquid 157 can have a density that is at least 0.2 g/ml greater than the density of water; in some embodiments, at least 0.3 g/ml greater; in some embodiments, at least 0.4 g/ml greater; in some embodiments, at least 0.5 g/ml greater; in some embodiments, at least 0.6 g/ml greater; in some embodiments, at least 0.7 g/ml greater; in some embodiments, at least 0.8 g/ml greater; in some embodiments, at least 0.9 g/ml greater; and in some embodiments, at least 1.0 g/ml greater. In some embodiments, the separation liquid 157 can have a density that is no greater than 2.0 g/ml greater than the density of water; in some embodiments, no greater than 1.8 g/ml greater; in some embodiments, no greater than 1.5 g/ml greater; in some embodiments, no greater than 1.3 g/ml greater; and in some embodiments, no greater than 1.0 g/ml greater. In some embodiments, the separation liquid 157 can have a density that ranges from 0.2 g/ml to 0.94 g/ml greater than the density of water. In some embodiments, the separation liquid 157 can have a density that ranges from 0.4 g/ml to 0.94 g/ml greater than the density of water.

In addition, the separation liquid 157 can have an interfacial tension (i.e., a liquid-liquid interfacial tension) with the sample 152, and particularly the supernatant 156, of at least 50 dynes/cm (0.05 N/m); in some embodiments, at least 52 dynes/cm (0.052 N/m); in some embodiments, at least 55 dynes/cm (0.055 N/m); in some embodiments, at least 56 dynes/cm (0.056 N/m); in some embodiments, at least 60 dynes/cm (0.06 N/m); and in some embodiments, at least 65 dynes/cm (0.065 N/m).

In some embodiments, the separation liquid 157 can have a surface tension of no greater than 20 dynes/cm (0.02 N/m); in some embodiments, no greater than 19 dynes/cm (0.019 N/m); in some embodiments, no greater than 18 dynes/cm (0.018 N/m); in some embodiments, no greater than 17 dynes/cm (0.017 N/m); in some embodiments, no greater than 16 dynes/cm (0.016 N/m); in some embodiments, no greater than 15 dynes/cm (0.015 N/m), and in some embodiments, no greater than 10 dynes/cm (0.01 N/m).

In some embodiments, the interfacial tension between the separation liquid 157 and the sample 152 (e.g., the supernatant 156) can be estimated by calculation—i.e., by subtracting the surface tension of the separation liquid 157 from the surface tension of the sample 152 (e.g., the supernatant 156).

In some embodiments, if the sample 152 is aqueous, the interfacial tension between the separation liquid 157 and the sample 152 (or the supernatant 156) can be approximated by finding, or calculating, the interfacial tension between the separation liquid 157 and water. For example, in some embodiments, the interfacial tension between the separation liquid 157 and water can be at least 50 dynes/cm (0.05 N/m); in some embodiments, at least 52 dynes/cm (0.052 N/m); in some embodiments, at least 55 dynes/cm (0.055 N/m); in some embodiments, at least 56 dynes/cm (0.056 N/m); in some embodiments, at least 60 dynes/cm (0.06 N/m); and in some embodiments, at least 65 dynes/cm (0.065 N/m).

Furthermore, it can be necessary that diffusion and/or dissolution of the sample 152 (e.g., the sediment or any analyte of interest and/or the supernatant 156) in the separation liquid 157 is minimized, and vice versa. For example, in some embodiments, the separation liquid 157 can have a solubility in the sample 152 (e.g., the supernatant 156) of less than 1% (or 10,000 ppm), in some embodiments, less than 0.1% (or 1,000 ppm), and in some embodiments, less than 0.01% (or 100 ppm).

In the case of an aqueous sample 152, the separation liquid 157 can be characterized by a solubility in water of less than 1% (or 10,000 ppm), in some embodiments, less than 0.1% (or 1,000 ppm), and in some embodiments, less than 0.01% (or 100 ppm).

In some embodiments, the solubility of the sample 152 (or of water) in the separation liquid 157 can be less than 1% (or 10,000 ppm), in some embodiments, less than 0.1% (or 1,000 ppm), and in some embodiments, less than 0.01% (or 100 ppm).

As mentioned above, the separation liquid 157 can also be non-toxic and inert with respect to the sample detection system, including the sample detection container 102, the sample 152, and any analytes of interest that may be present in the sample 152.

In some embodiments, the separation liquid 157 can also be colorless to provide for (and not interfere with) a variety of interrogation methods for interrogating the microcavity 136. For example, for some types of detection (e.g., fluorescence) the separation liquid 157 can be configured to allow the microcavity 136 to be excited from above (i.e., through the separation liquid 157), from below, and/or from a side, as well as to be detected from above, from below, and/or from a side.

The phase "colorless" is generally used to refer to a body or substrate that transmits at least 50% of electromagnetic radiation having wavelengths at a selected wavelength or within a selected range of wavelengths in the ultraviolet (e.g., from about 200 nm to about 400 nm; "UV") spectrum and/or in the visible (e.g., from about 400 nm to about 700 nm; "Vis") spectrum; in some embodiments, at least about 75% of a selected wavelength (or range) in the UV and/or Vis spectra; and in some embodiments, at least about 90% of a selected wavelength (or range) in the UV and/or Vis spectra.

In some embodiments, the separation liquid 157 can include liquids comprising a fluorocarbon, fluorocarbon derivatives, perfluorinated compounds, other suitable compounds, or a combination thereof; other liquids that meet the limitations of the present disclosure; or a combination thereof. Examples of fluorocarbon-based liquids can include electronic liquids available under the trade designation 3M™ FLUORINERT™ (3M Company, St. Paul, Minn.); engineered fluids available under the trade designation 3M™ NOVEC™ (3M company); fluorinated oils available under the trade designation KRYTOX® (Dupont, Wilmington, Del.); other suitable fluorocarbon-based liquids; or a combination thereof. In general, a "perfluorinated compound" is an organofluorine compound with all hydrogens replaced by fluorine on a carbon chain, where the molecule also contains at least one different atom or functional group. In general, a "fluorocarbon" is a compound formed by replacing one or more of the hydrogen atoms in a hydrocarbon with fluorine atoms. Fluorocarbons are sometimes referred to as perfluorocarbons.

As shown in step 150D of FIG. 4, the concentrate 154 in the microcavity 136 can then be interrogated (e.g., optically interrogated) from the outside or exterior of the sample detection container 102, i.e., from the second side 141 of the sample detection container 102, as represented by the large arrow. The large arrow is shown as being directed straight up toward the microcavity 136 (i.e., toward its base 146), but it should be understood that the microcavity 136 can be interrogated from any desired direction (e.g., including through the separation liquid 157). As described above, the sample detection container 102, or at least a portion thereof, can be colorless in order to enable interrogating (e.g., optically) the concentrate 154 from the second side 141. Also, such embodiments can employ a sample detection container 102 and a cap 104 that are permanently coupled together, because the detection, or interrogation, step can be performed from the outside of the sample detection system 100, such that the cap 104 need not be decoupled from the sample detection container 102 for the interrogation step. Also, in such embodiments, as shown in step 150D of FIG. 4, the supernatant 156 and separation liquid 157 remain above the microcavity 136, which can avoid substantial evaporation of the concentrate 154 before the detection/interrogated process is completed.

The interrogation of the concentrate 154 can include any of the above-described detection methods for detecting an analyte of interest in a sample, including optical interrogation methods, such as optical scanning, imaging, or any of the other methods described above. For example, fluorescent detection can include directing electromagnetic energy toward the concentrate 154 in the microcavity 136 at a first frequency, and detecting electromagnetic energy emitted from the concentrate 154 in the microcavity 136 at a second frequency. By way of further example, colorimetric detection can include emitting electromagnetic energy at the concentrate 154 in the microcavity 136 at a broad range of frequencies (i.e., broad-spectrum light), and detecting at least one of the transmittance and the absorbance of at least a portion of the concentrate 154 in the microcavity 136.

In some embodiments, the microcavity 136 can include a base 146 that is formed by at least a portion of the second side (or second major surface) 141 of the sample detection container 102, and which is substantially transparent, such that the contents of the microcavity 136 can be visible from the second side 141 of the sample detection container 102 (i.e., from the outside of the sample detection system 100). In such embodiments, any sidewalls of the microcavity 136 can be substantially non-transparent to inhibit cross-talk between wells, and to enhance detection, particularly, optical detection or interrogation.

In some embodiments, at least a portion of the sample detection container 102 can include an optical window that is substantially transparent. The optical window can be at least partially coextensive (i.e., overlapping) with the microcavity 136, such that the microcavity 136 (and its contents) is visible from the outside of the sample detection container 102, and particularly from the second side 141 of the sample detection container 102.

Alternatively, as shown in step 150E of FIG. 4, the sample detection container 102 (i.e., the sample detection system 100) can be inverted, e.g., prior to detection, such that the supernatant 156 resulting from the centrifugation step and the separation liquid 157 is decanted from the microcavity 136, while the concentrate 154 remains retained in the microcavity 136. As shown by the large arrow in step 150E, the concentrate 154 in the microcavity 136 can then be interrogated (e.g., optically interrogated) from the outside or exterior of the sample detection container 102, i.e., from the second side 141 of the sample detection container 102, as represented by the large arrow. The large arrow is shown as being directed straight down toward the microcavity 136 (i.e., toward its base 146), but it should be understood that the microcavity 136 can be interrogated from any desired direction. As described above, the sample detection container 102, or at least a portion thereof, can be substantially transparent in order to enable interrogating (e.g., optically) the concentrate 154 from the second side 141. Also, in such embodiments, as shown in step 150D of FIG. 4, the supernatant 156 (and the separation liquid 157) can serve as a humidity reservoir to avoid substantial evaporation of the concentrate 154 before the detection/interrogated process can be completed.

As further shown in step 150E, because the separation liquid 157 is denser than the supernatant 156, the separation liquid 157 moves toward the cap 104 when the sample detection system 100 is inverted.

The term "inverted" is used herein to refer to a change in orientation and can include orienting at a variety of angles, and is not limited to changing the orientation by 180 degrees. The microcavity 136 can be adapted to retain the concentrate 154 under normal gravitational forces (e.g., under standard gravity, i.e., the standard value of Earth's gravitational acceleration at sea level, 9.8 m/s$^2$).

In some embodiments, the inverting step can include inverting the container 108 by at least 20 degrees (e.g., from −10 degrees to +10 degrees, or from 0 degrees to +20 degrees, etc.), in some embodiments, by at least 45 degrees, in some embodiments, by at least 60 degrees, in some embodiments, by at least 90 degrees, and in some embodiments, by 180 degrees. For example, in embodiments in which the cap 104 is oriented at −90 degrees (e.g., from a horizontal), as shown in steps 150A and 150B of FIG. 4, the container 108 may need to be inverted at least 90 degrees (e.g., to 0 degrees) or more in order to adequately drain the supernatant 156 away from the concentrate 154 retained in the microcavity 136, if such drainage is desired.

As mentioned above, the speed of inverting the sample detection containers of the present disclosure need not be tightly controlled for the purpose of ensuring that the concentrate 154 is substantially contained in the microcavity 136 and/or protected from turbulence as the supernatant 156 is drained away.

Figure 5:
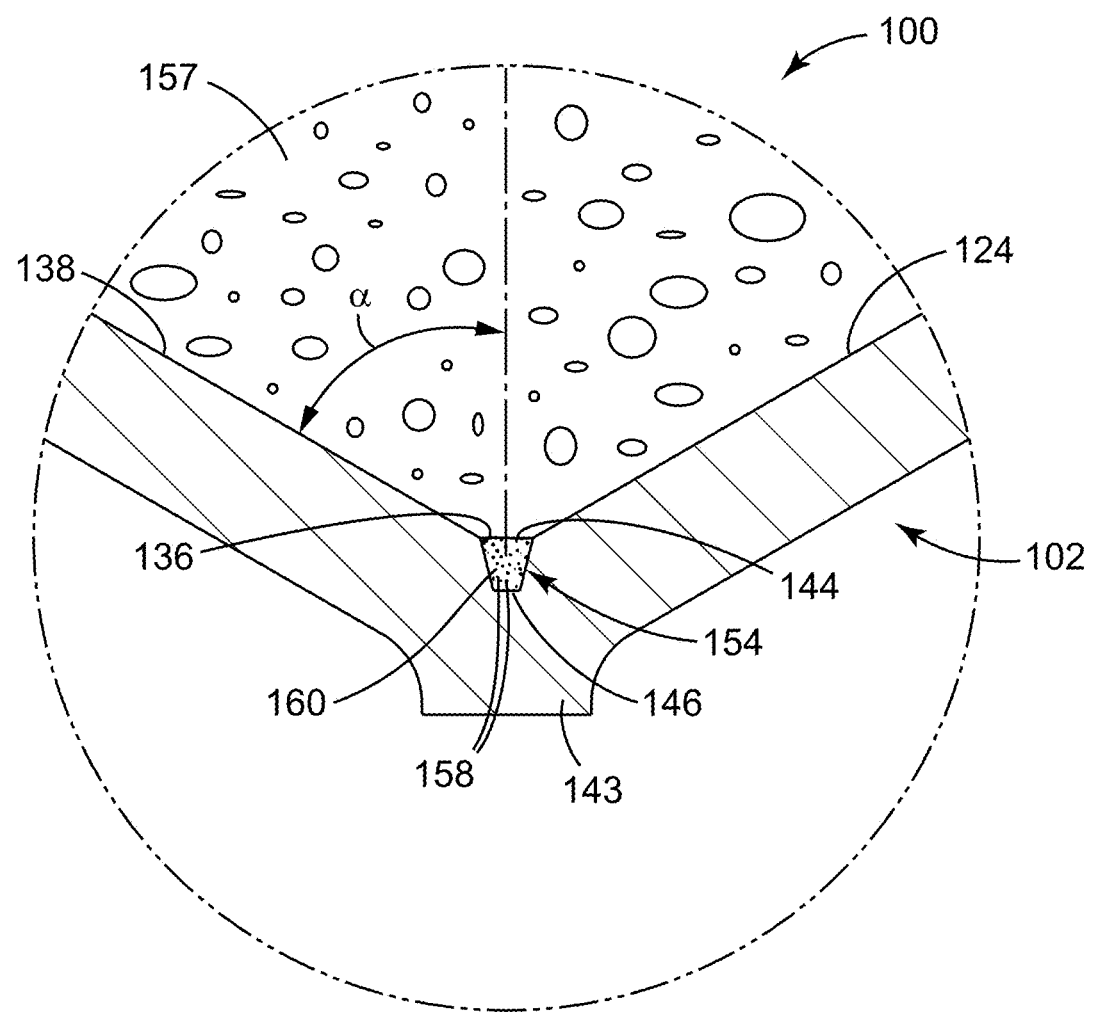
FIG. 5 is a close-up schematic partial cross-sectional view of a portion of the sample detection container of FIGS. 1-4, taken as shown in FIG. 4.

FIG. 5 illustrates a schematic close-up cross-sectional view of the sample detection container 102, with the concentrate 154 retained in the microcavity 136 of the sample detection container 102. As shown in FIG. 5, the microcavity 136 can be formed in the inner surface 124 (or first side 140) of the sample detection container 102.

In some embodiments, as shown in FIG. 5, the concentrate 154 can include insoluble matter 158 and a liquid 160, which can also include soluble matter, and particularly, soluble matter having a lower density than the insoluble matter 158. The concentrate 154, and particularly, the insoluble matter 158 (if present) can include the analyte(s) of interest (e.g., the microorganism(s) of interest or an analyte representative of the microorganism(s) of interest), if present in the sample 152. The liquid 160 can include at least a portion of the supernatant 156 of the sample 152.

As shown in FIG. 5, the separation liquid 157 can separate the concentrate 154 in the microcavity 136 from the bulk supernatant 156 (see FIG. 4) above the microcavity 136, such that the separation liquid 157 covers a top opening 144 of the microcavity 136, and isolates the concentrate 154 in the microcavity 136 from a remainder of the sample 152 (e.g., the bulk supernatant located above or outside of the microcavity 136).

The sample detection method 150 illustrated in FIG. 4 and described above can provide efficient collection and isolation of the concentrate 154 of the sample 152 (i.e., and any analyte(s) of interest that may be present in the sample 152) with minimal loss of the sample 152 and/or the concentrate 154. For example, efficient collection can be achieved by essentially "trapping" the concentrate 154 (comprising the analyte(s) of interest, if present) in the sample detection container 102 during the centrifugation step 150B illustrated in FIG. 4. The concentrate 154 can generally have a much higher concentration than the sample 152 of any analyte(s) of interest that may have been present in the sample 152.

Based on the centrifugation parameters employed in the centrifugation step, and/or on the number, shape and dimensions of the microcavity 136 employed in the sample detection container 102, the mass and/or volume of the concentrate 154 retained in the sample detection container 102 can be determined That is, the sample detection container 102 (and/or the centrifugation steps) can be configured according to the sample 152 to concentrate the desired analyte(s) of interest. In some embodiments, the sample detection container 102 can be used to obtain a predictable volume each time, because the volume of the microcavity 136 of the sample detection container 102 is constant. The microcavity 136 of the sample detection container 102 will be now described in greater detail.

As further shown in FIG. 5, the microcavity 136 can be formed in the inner surface 124 of the sample detection container 102. In some embodiments, the one or more microcavity 136 can be formed by a variety of methods, including a variety of microreplication methods, including, but not limited to, molding (e.g., injection molding), other suitable techniques, or combinations thereof. In some embodiments, tools (e.g., molds) for making the microcavity 136 can be formed by a variety of methods, including, but not limited to coating, casting, etching (e.g., chemical etching, mechanical etching, reactive ion etching, etc., and combinations thereof), ablation (e.g., laser ablation, etc.), photolithography, stereolithography, micromachining, knurling (e.g., cutting knurling or acid enhanced knurling), scoring, cutting, etc., or combinations thereof.

The microcavity 136 is adapted to retain the concentrate 154 resulting from the centrifugation step 150B of FIG. 4, and described above.

In the embodiment illustrated in FIG. 5, the microcavity 136 is shaped to include edges or corners (e.g., at its base 146). Such edges or corners can facilitate the retention of the concentrate 154 in the microcavity 136 and can inhibit the concentrate 154 from being removed from the microcavity 136 under normal gravitational forces. For example, in embodiments in which the concentrate 154 has a high surface energy, or in which the concentrate 154 includes molecules that are attracted to those of the material making up the inner surface 124 of the sample detection container 102, the concentrate 154 can be preferentially attracted to edges and/or corners of the microcavity 136 (i.e., where the concentrate 154 can remain in contact with two or more surfaces), rather than smooth single surfaces.

The effective angle $\alpha$ of the wall 138 is also shown in FIG. 5. As mentioned above, the effective angle $\alpha$ of the wall 138 of the sample detection container 102 of FIGS. 1-3, 4 and 5 is shown as being 60 degrees by way of example only. In addition, the single microcavity 136 is shown by way of example only.

As further shown in FIG. 5, the separation liquid 157 can isolate the concentrate 154 of the sample 152 in the microcavity 136, such that the retained volume is about equal to (or less than) the volume defined by the microcavity 136.

That is, in systems and methods of the present disclosure that employ the separation liquid 157, the ratio of the total retained volume of the concentrate 154 to the microcavity volume is about 1.

Figure 6:
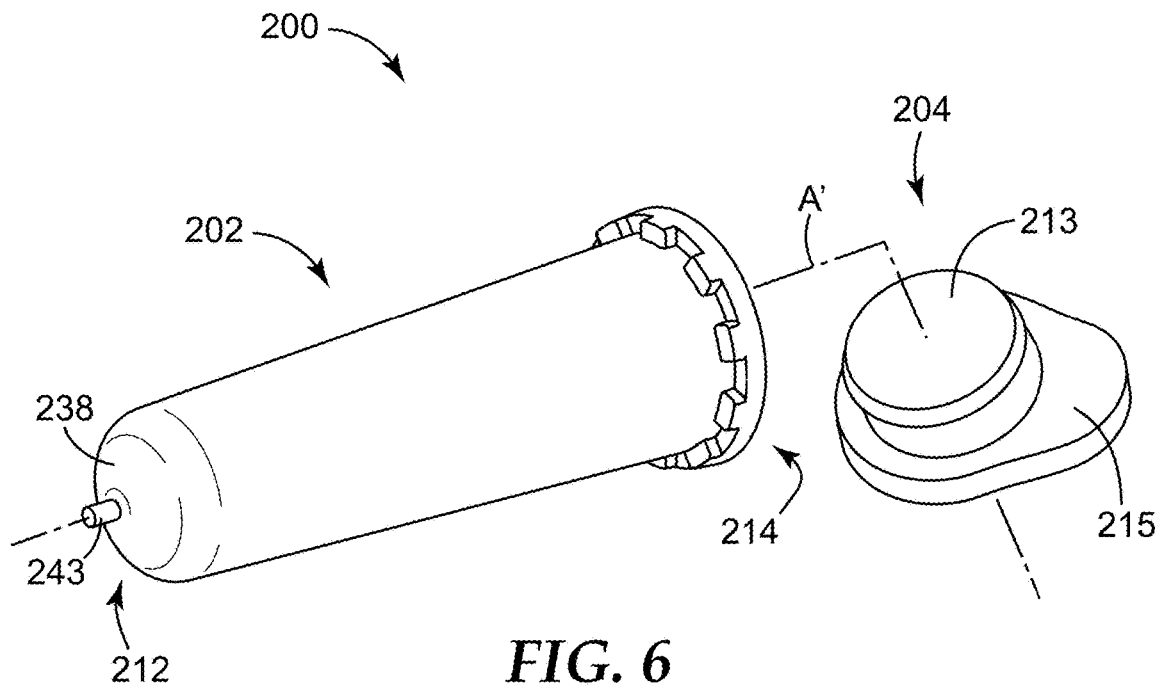
FIG. 6 is an exploded perspective view of a sample detection container according to another embodiment of the present disclosure.
Figure 7:
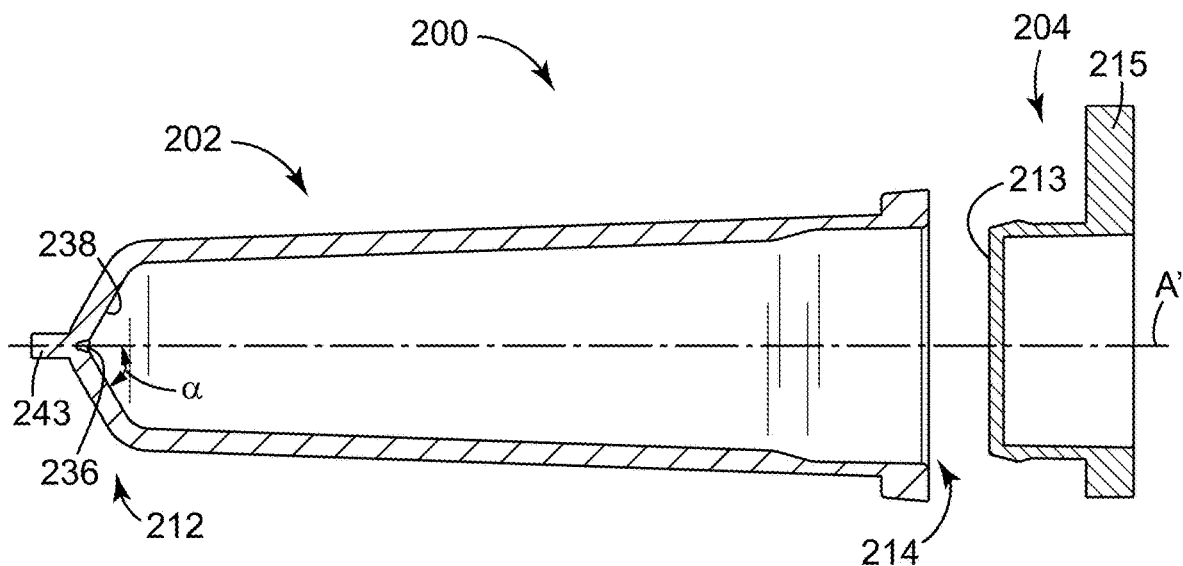
FIG. 7 is an exploded side cross-sectional view of the sample detection container of FIG. 6.

FIGS. 6 and 7 illustrate a sample detection system 200 according to another embodiment of the present disclosure, wherein like numerals represent like elements. The sample detection system 200 of FIGS. 6 and 7 shares many of the same elements, features, and functions as the sample detection system 100 described above with respect to FIGS. 1-5. Reference is made to the description above accompanying FIGS. 1-5 for a more complete description of the features and elements (and alternatives to such features and elements) of the embodiment illustrated in FIGS. 6-7. Any of the features described above with respect to FIGS. 1-5 can be applied to the embodiments of FIGS. 6-7, and vice versa.

The sample detection system 200 includes a sample detection container 202 and a cap 204. As shown in FIGS. 6 and 7, the sample detection container 202 can be an elongated tube having a closed end or base 212 (e.g., a tapered closed end 212) and an open end 214. By way of example only, the cap 204 is illustrated as including a portion (e.g., a projection) 213 dimensioned to be received in the open end 214 of the sample detection container 202. The cap 204 is further illustrated as including a tab or flange 215 to facilitate removing the cap 204 from the sample detection container 202 when desired. By way of example only, the sample detection container 202 and the cap 204 are configured to be coupled together by a snap-fit-type engagement. In some embodiments, one or both of the sample detection container 202 and the cap 204 can include a seal (e.g., o-ring) coupled thereto or integrally formed therewith to provide a sealed container when the sample detection container 202 and the cap 204 are coupled together.

The closed end 212 of the sample detection container 202 can include (i.e., terminate in) one or more microcavities 236 adapted to retain a concentrate of the sample to be analyzed, the microcavity 236 opening toward the open end 214 of the sample detection container 202. The closed end 212 can further include a wall 238 that extends to the microcavity 236 and is oriented at an effective angle $\alpha$ (i.e., with respect to a longitudinal axis A'). The closed end 212 can further include one or more protrusions 243 that surround the microcavity 236.

The main differences between the sample detection system 200 of FIGS. 6 and 7 and the sample detection system 100 of FIGS. 1-5 are the overall sizes/volumes and the aspect ratios (i.e., ratio of length to transverse dimension (e.g., diameter or width)) of the sample detection containers 102, 202. The sample detection container 102 has a lower aspect ratio than the sample detection container 202.

In addition, the sample detection container 102 has a transverse dimension (e.g., diameter) that is greater than the diameter of the sample detection container 202. As a result, if the microcavity 136 is the same, or on the same order of magnitude as, the microcavity 236, the ratio of the microcavity 136 to the transverse dimension (e.g., diameter) of the sample detection container 102 is lower than the ratio of the microcavity 236 to the transverse dimension (e.g., diameter) of the sample detection container 202.

By way of example only, the sample detection container 202 has an effective angle α of 60 degrees. Sample detection containers configured as shown in FIGS. 1-3, 4 and 5 and FIGS. 6-7, along with similar sample detection containers having effective angles α of 45 degrees, were tested (see the Examples) and shown to be effective in retaining a portion of a sample after centrifugation, when employed with separation liquids of the present disclosure.

Figure 8:
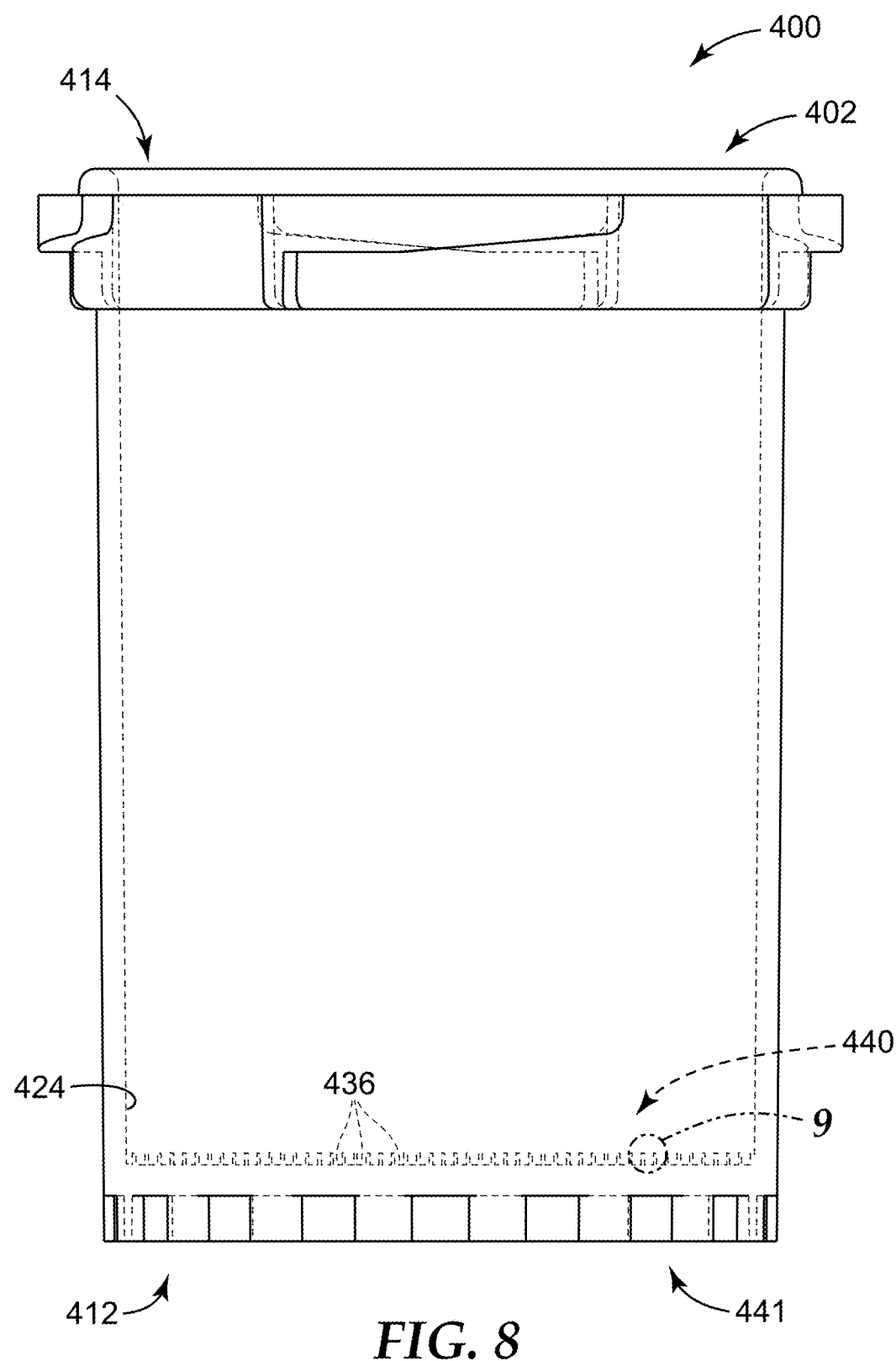
FIG. 8 is a side elevational view of a sample detection container according to another embodiment of the present disclosure.
Figure 9:
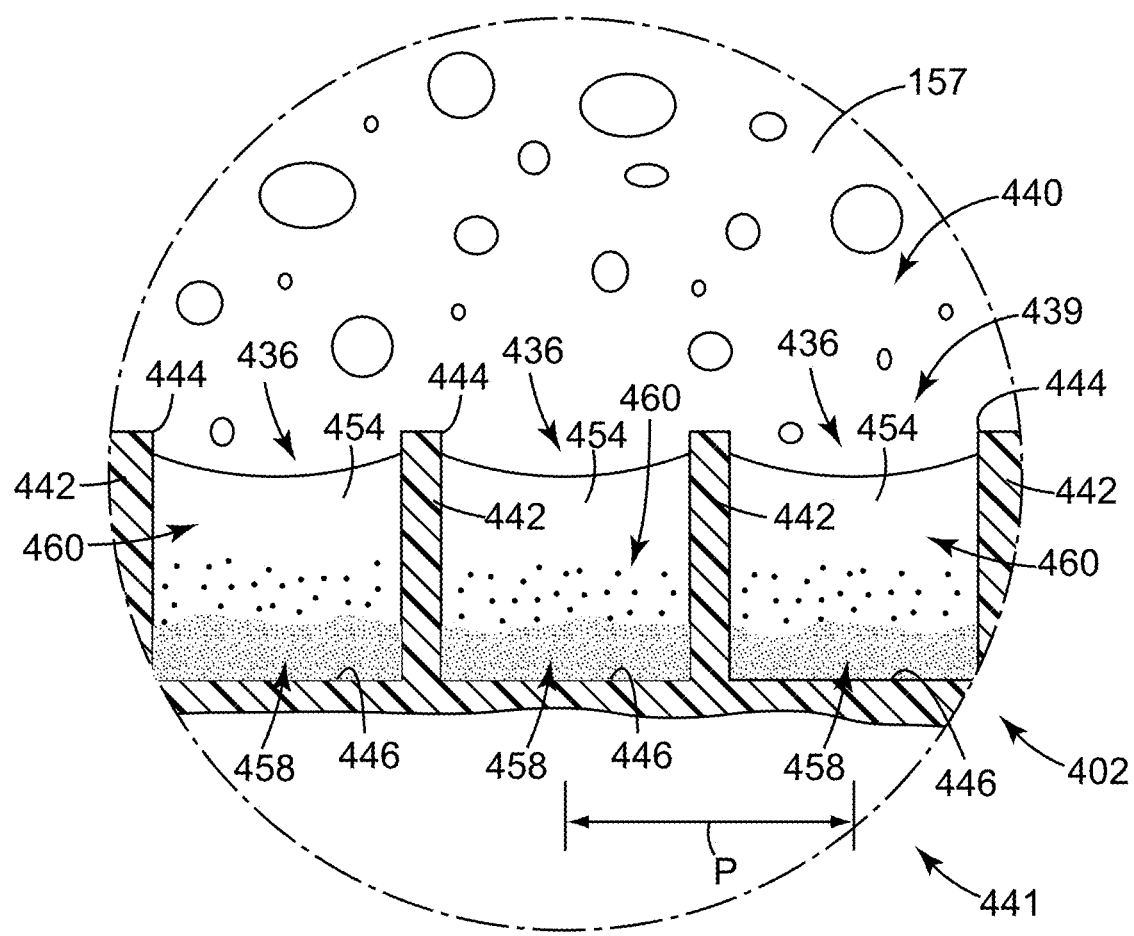
FIG. 9 is a close-up schematic partial cross-sectional view of a portion of the sample detection container of FIG. 8, taken as shown in FIG. 8.

FIGS. 8 and 9 illustrate a sample detection system 400 according to another embodiment of the present disclosure, wherein like numerals represent like elements. The sample detection system 400 of FIGS. 8 and 9 shares many of the same elements, features, and functions as the sample detection system 100 described above with respect to FIGS. 1-5 and the sample detection system 200 of FIGS. 6 and 7. Reference is made to the description above accompanying FIGS. 1-7 for a more complete description of the features and elements (and alternatives to such features and elements) of the embodiment illustrated in FIGS. 8-9. Any of the features described above with respect to FIGS. 1-7 can be applied to the embodiments of FIGS. 8-9, and vice versa.

The sample detection system 400 includes a sample detection container 402. A cap of the system 400 is not illustrated in FIG. 8, but it should be understood that any of a variety of mating caps can be employed to effectively close and seal the sample detection container 402, such as the cap 104 of the sample detection system 100. The sample detection container 402 can be coupled to any such cap by any of the above-described coupling means, optionally employing one or more seals (e.g., o-rings).

As shown in FIG. 8, the sample detection container 402 can be an elongated tube having a closed end or base 412 (e.g., a non-tapered closed end 412) and an open end 414. The closed end 412 of the sample detection container 402 can include (i.e., terminate in) one or more microcavities 436 adapted to retain a concentrate of the sample to be analyzed, the microcavities 436 opening toward the open end 414 of the sample detection container 402. By way of example only, the sample detection container 402 is illustrated as including a flat inner surface 424 in which a microcavity surface is formed, such that the sample detection container 402 includes a plurality of microcavities 436. Any of the features, alternatives and methods of making of the microcavity 136 described above can also be applied to each of the plurality of microcavities 436 of FIGS. 8 and 9.

Particularly, the microcavities 436 are formed in a first side 440 of the sample detection container 402 that generally faces the interior (or "inside") of the sample detection container 402, and that generally includes the inner surface 424 of the sample detection container 402, or a portion thereof. Particularly, the first side 440 can include the inner surface 424 in which the microcavities 436 can be formed, such that the top opening 444 of each microcavity 436 opens toward the first side 440 of the sample detection container 402, and toward the interior of the sample detection container 402 (see FIG. 9). The sample detection container 402 can further include a second side 441 that is generally opposite the first side 440. The second side 441 can face outside of the sample detection container 402, for example, away from the sample detection container 402. As a result, a concentrate retained in the sample detection container 402 (i.e., in the microcavities 436) can be interrogated from the second side 441.

Sample detection containers configured as shown in FIGS. 8-9 were tested (see the Examples) and shown to be effective in retaining a portion of a sample after centrifugation, when employed with separation liquids of the present disclosure.

By way of example only, FIG. 9 illustrates a close-up schematic view of the sample detection container 402, after the sample detection container 402 has been subjected to steps 150A-150D of FIG. 4, employing the separation liquid 157.

As shown in FIG. 9, the separation liquid 157 can separate a concentrate 454 in the microcavities 436 from a bulk supernatant (i.e., located above the microcavities 436 and out of view of FIG. 9), such that the separation liquid 157 covers a top opening 444 of each microcavity 436, and isolates the concentrate 454 in each microcavity 436 from a remainder of the sample 452 (e.g., the bulk supernatant located above or outside of the microcavity 436).

In some embodiments, as shown in FIG. 9, the concentrate 454 can include insoluble matter 458 and a liquid 460, which can also include soluble matter, and particularly, soluble matter having a lower density than the insoluble matter 458. The concentrate 454, and particularly, the insoluble matter 458 (if present) can include the analyte(s) of interest (e.g., the microorganism(s) of interest or an analyte representative of the microorganism(s) of interest), if present in the sample. The liquid 460 can include at least a portion of the supernatant of the sample.

As further shown in FIG. 9, the separation liquid 157 can isolate the concentrate 454 of the sample in the microcavities 436, such that the retained volume is about equal to (or less than) the collective volume defined by the plurality of microcavities 436. That is, in systems and methods of the present disclosure that employ the separation liquid 157, the ratio of the total retained volume of the concentrate 454 to the collective microcavity volume is about 1. In addition, with respect to each individual microcavity 436, the ratio of the total retained volume of the concentrate 454 retained in each microcavity 436 to the individual microcavity volume is also about 1.

As mentioned above with respect to FIG. 8, the microcavities 436 can be formed in the inner surface 424 of the sample detection container 402. However, in some embodiments, the microcavities 436 can alternatively, or additionally, be formed in a substrate (or insert or film) that can be coupled to (e.g., positioned against) at least a portion of the inner surface 424 of the sample detection container 402. In embodiments employing a substrate (or film), the thickness of the substrate can be at least about 25 micrometers, in some embodiments, at least about 100 micrometers, and in some embodiments, at least about 400 micrometers. In some embodiments, the thickness of the substrate can be no greater than about 2000 micrometers, in some embodiments, no greater than about 1000 micrometers, and in some embodiments, no greater than about 250 micrometers.

In some embodiments, the substrate can be a film that can be formed of a variety of suitable materials, including but not limited to a polyolefins such as polypropylene, polyethylene, or a blend thereof; olefin copolymers (e.g., copolymers with vinyl acetate); polyesters such as polyethylene terephthalate and polybutylene terephthalate; polyamide (Nylon-6 and Nylon-6,6); polyurethanes; polybutene; polylactic acids; polyvinyl alcohol; polyphenylene sulfide; polysulfone; polycarbonates; polystyrenes; liquid crystalline polymers; polyethylene-co-vinylacetate; polyacrylonitrile; cyclic polyolefins; or a combination thereof. In some embodiments, the film can comprise a compound selected from the group consisting of 1-(3-methyl-n-butylamino)-9,10-anthracenedione; 1-(3-methyl-2-butylamino)-9,10-anthracenedione; 1-(2-heptylamino)-9,10-anthracenedione; 1,1,3,3-tetramethylbutyl-9,10-anthracenedione; 1,10-decamethylene-bis-(-1-amino-9,10-anthracenedione); 1,1-dimethylethylamino-9,10-anthracenedione; and 1-(n-butoxypropylamino)-9,10-anthracenedione. In some embodiments, the film material can include a cured polymer. Such a cured polymer can be derived from a resin selected from the group consisting of acrylate resins, acrylic resins, acrylic-based resins derived from epoxies, polyesters, polyethers, and urethanes; ethylenically unsaturated compounds; aminoplast derivatives having at least one pendant acrylate group; polyurethanes (polyureas) derived from an isocyanate and a polyol (or polyamine); isocyanate derivatives having at least one pendant acrylate group; epoxy resins other than acrylated epoxies; and mixtures and combinations thereof.

As further shown in FIG. 9, the microcavities 436 can be at least partially defined by a plurality of walls 442, and each microcavity 436 can be further defined by a base 446. In some embodiments, the walls 442 can be intersecting walls 442 to define individual cavities, rather than channels having a length.

In some embodiments, the one or more microcavities 436 can define microcavity surface (or a microstructured surface) 439. By way of example only, the microcavity surface 439 is illustrated in FIG. 8 as extending across the entire bottom surface of the sample detection container 402; however, in some embodiments, the microcavity surface 439 may only be present in a portion of the base of the sample detection container 400.

In such embodiments, the microcavity surface 439 can be formed by a variety of methods, including a variety of microreplication methods, including, but not limited to, casting, coating, molding, and/or compressing techniques, other suitable techniques, or combinations thereof. For example, microstructuring of the microcavity surface 439 can be achieved by at least one of (1) casting a molten thermoplastic using a tool having a microstructured pattern, (2) coating of a fluid onto a tool having a microstructured pattern, solidifying the fluid, and removing the resulting film, and/or (3) passing a thermoplastic film through a nip roll to compress against a tool (e.g., male tooling) having a microstructured pattern (i.e., embossing). The tool can be formed using any of a number of techniques known to those skilled in the art, selected depending in part upon the tool material and features of the desired topography. Other suitable techniques include etching (e.g., chemical etching, mechanical etching, reactive ion etching, etc., and combinations thereof), ablation (e.g., laser ablation, etc.), photolithography, stereolithography, micromachining, knurling (e.g., cutting knurling or acid enhanced knurling), scoring, cutting, etc., or combinations thereof.

Alternative methods of forming the microcavity surface 439 include thermoplastic extrusion, curable fluid coating methods, and embossing thermoplastic layers, which can also be cured. Additional information regarding the substrate or film material and various processes for forming the microcavity surface 439 can be found, for example, in Halverson et al., PCT Publication No. WO 2007/070310 and US Publication No. US 2007/0134784; Hanschen et al., US Publication No. US 2003/0235677; Graham et al., PCT Publication No. WO2004/000569; Ylitalo et al., U.S. Pat. No. 6,386,699; and Johnston et al., US Publication No. US 2002/0128578 and U.S. Pat. Nos. 6,420,622, 6,867,342, and 7,223,364, each of which is incorporated herein by reference.

With microreplication, the microcavity surface 439 can be mass produced without substantial variation from product-to-product and without using relatively complicated processing techniques. In some embodiments, microreplication can produce a microcavity surface that retains an individual feature fidelity during and after manufacture, from product-to-product, that varies by no more than about 50 micrometers. In some embodiments, the microcavity surface 439 retains an individual feature fidelity during and after manufacture, from product-to-product, which varies by no more than 25 micrometers. In some embodiments, the microcavity surface 439 comprises a topography (i.e., the surface features of an object, place or region thereof) that has an individual feature fidelity that is maintained with a resolution of between about 50 micrometers and 0.05 micrometers, and in some embodiments, between about 25 micrometers and 1 micrometer.

The microcavities 436 are adapted to retain the concentrate 454 resulting from the centrifugation step 150B of FIG. 4. Each microcavity 436 is shown in FIG. 9 as having a generally rectangular cross-sectional shape and as being formed by at least two walls 442 and a base or closed end 446, and each microcavity 436 is separated from an adjacent microcavity 436 by a wall 442. Each microcavity 436 also includes an open end or top opening 444. It should be understood that the microcavities 436 can include a variety of shapes so as to be able to retain the concentrate 154. Said another way, each microcavity 436 can be shaped and dimensioned to provide a reservoir, or well, for the concentrate 454.

Furthermore, the microcavities 436 illustrated in FIG. 9 are shown by way of example only as being regularly arranged (e.g., in a cellular array). However, it should be understood that the microcavities 436 can include a variety of regular arrangements or arrays, random arrangements, or combinations thereof. In some embodiments, the microcavities 436 are arranged randomly on a local or smaller scale, but the random arrangements repeat, or are ordered, on a larger scale. Alternatively, in some embodiments, the microcavities 436 are ordered on a smaller scale, but the ordered regions are randomly arranged on a larger scale.

In addition, in the embodiment illustrated in FIG. 4, the walls 442 are all of the same size and shape. However, it should be understood that a variety of other wall shapes are possible. For example, the walls 442 need not include a substantially rectangular cross-sectional shape, but rather can include any of the above-described cross-sectional shapes.

The walls 442 and the microcavities 436 can be characterized by a variety of sizes, dimensions, distances between walls 442 or microcavities 436, relative sizes, etc. The walls 442 generally have dimensions such as thickness, height, length, width, etc. The microcavities 436 generally have volumes with dimensions such as a radius, diameter, height, width, length, etc. Generally, the walls 442 and/or the microcavities 436 are sized, shaped and spaced to retain the concentrate 454 in the microcavities 436 when sample detection container 402 is in any orientation (e.g., by capillary forces).

In some embodiments, the walls 442 can have an average thickness of at least about 1 micrometer, in some embodiments, at least about 5 micrometers, and in some embodiments, at least about 10 micrometers. In some embodiments, the walls 442 can have an average thickness of no greater than about 50 micrometers, in some embodiments, no greater than about 30 micrometers, and in some embodiments, no greater than about 20 micrometers.

In some embodiments, the walls 442 can be shaped and/or sized to minimize the area of the top surface of the walls 442 so that any matter collected on the top surface of the walls 142 can be diverted into an adjacent microcavity 436. For example, in some embodiments, the walls 442 can include a taper toward the top surface. In some embodiments, the top surface can include a convex shape. In some embodiments, a combination of a taper and a convex shape can be employed. In some embodiments, the top surface is not radiused, but rather is flat; however, the top surface defining the openings 444 of the microcavities 436 are smooth with little to no sharp edges.

In some embodiments, the configuration of the walls 442 and the microcavities 436 in any given region can be chosen such that the average wall or microcavity pitch P (i.e., the center to center distance between adjacent walls 442 or microcavities 436, respectively) is at least about 1 micrometer, in some embodiments, at least about 10 micrometers, and in some embodiments, at least about 50 micrometers. In some embodiments, the average wall or microcavity pitch P is no greater than about 1000 micrometers, in some embodiments, no greater than about 800 micrometers, in some embodiments, no greater than about 600 micrometers, in some embodiments, no greater than about 500 micrometers, in some embodiments, no greater than about 200 micrometers, in some embodiments, no greater than about 150 micrometers, and in some embodiments, no greater than about 100 micrometers. In some embodiments, the pitch P can range from 50 micrometers to 850 micrometers.

In general, the higher the packing density of the microcavities 436 (e.g., referred to as average microcavity density or average well density), generally, the more concentrate 454 a given area of the first side 440 of the sample detection container 402 can contain. Also, in some embodiments, if the microcavity surface 439 includes more land area between microcavities 436, it is possible that the denser portions of the sample (e.g., comprising the analyte of interest) can be centrifuged onto a land area. Therefore, in general, higher microcavity densities on the microcavity surface 439 would be preferred to afford a higher likelihood of capture.

In some embodiments, the average microcavity density is at least about 20 microcavities/cm$^2$, in some embodiments, at least about 30 microcavities/cm$^2$, in some embodiments, at least about 70 microcavities/cm$^2$, in some embodiments, at least about 100 microcavities/cm$^2$, in some embodiments, at least about 150 microcavities/cm$^2$, in some embodiments, at least about 200 microcavities/cm$^2$, in some embodiments, at least about 500 microcavities/cm$^2$, in some embodiments, at least about 800 microcavities/cm$^2$, in some embodiments, at least about 900 microcavities/cm$^2$, in some embodiments, at least about 1000 microcavities/cm$^2$, in some embodiments, at least about 2000 microcavities/cm$^2$, and in some embodiments, at least about 3000 microcavities/cm$^2$. In some embodiments, the microcavity density can be about 825 microcavities/cm$^2$.

In some embodiments, the average height of the walls 442 or the average depth of the microcavities 436 (i.e., the distance between the closed end, or base, 446 of each microcavity 436 and the open end, or top opening, 444 of the microcavity 436) is at least about 5 micrometers, in some embodiments, at least about 20 micrometers, and in some embodiments, at least about 30 micrometers. In some embodiments, the average height of the walls 442 or the average depth of the microcavities 436 can be no greater than about 1000 micrometers, in some embodiments, no greater than about 250 micrometers, in some embodiments, no greater than about 100 micrometers, and in some embodiments, no greater than about 50 micrometers. In the embodiment illustrated in FIG. 9, the wall height is substantially the same as the microcavity depth; however, it should be understood that this need not be the case. For example, in some embodiments, the microcavities 436 include a portion that is recessed even below the bottom of the walls 442, such that the microcavity depth is greater than the wall height. However, even in such embodiments, the above size ranges can apply.

As mentioned above, in some embodiments, the microcavities 436 can each include a draft angle β. However, for simplicity, the microcavities 436 of FIG. 9 are illustrated without showing such a draft angle β.

FIGS. 10-14 illustrate a sample detection system 300 according to one embodiment of the present disclosure, wherein like numerals generally represent like elements. The sample detection system 300 of FIGS. 10-14 shares many of the same elements, features, and functions as the sample detection systems 100, 200 and 400 described above with respect to FIGS. 1-5, 6-7 and 8-9, respectively. Reference is made to the description above accompanying FIGS. 1-9 for a more complete description of the features and elements (and alternatives to such features and elements) of the embodiment illustrated in FIGS. 10-14. Any of the features described above with respect to FIGS. 1-5, FIGS. 6-7, or FIGS. 8-9 can be applied to the embodiments of FIGS. 10-14, and vice versa.

The sample detection system 300 illustrates how the sample detection container 102 of FIGS. 1-3, 4 and 5 (or the sample detection container 202 of FIGS. 6-7) can be employed with filtration components, which can be used to pre-filter a sample prior to concentrating the sample using the sample detection container 102. The sample detection container 102 is shown by way of example only, but it should be understood than any sample detection container of the present disclosure can instead be employed in the sample detection system 300.

The sample detection system 300 can include a first container (or "first container assembly") 303 (see FIGS. 10, 11 and 14) and a second container (or "second container assembly") 305 (see FIGS. 3, 4 and 5). The second container 305 can include the sample detection container 102. In some embodiments, the sample detection system 300 can be used to concentrate a sample to form a concentrate (e.g., in the microcavity 136, as described below), and can be further used to interrogate the concentrate for an analyte of interest, that is, for detecting the presence or absence of an analyte of interest.

Figure 10:
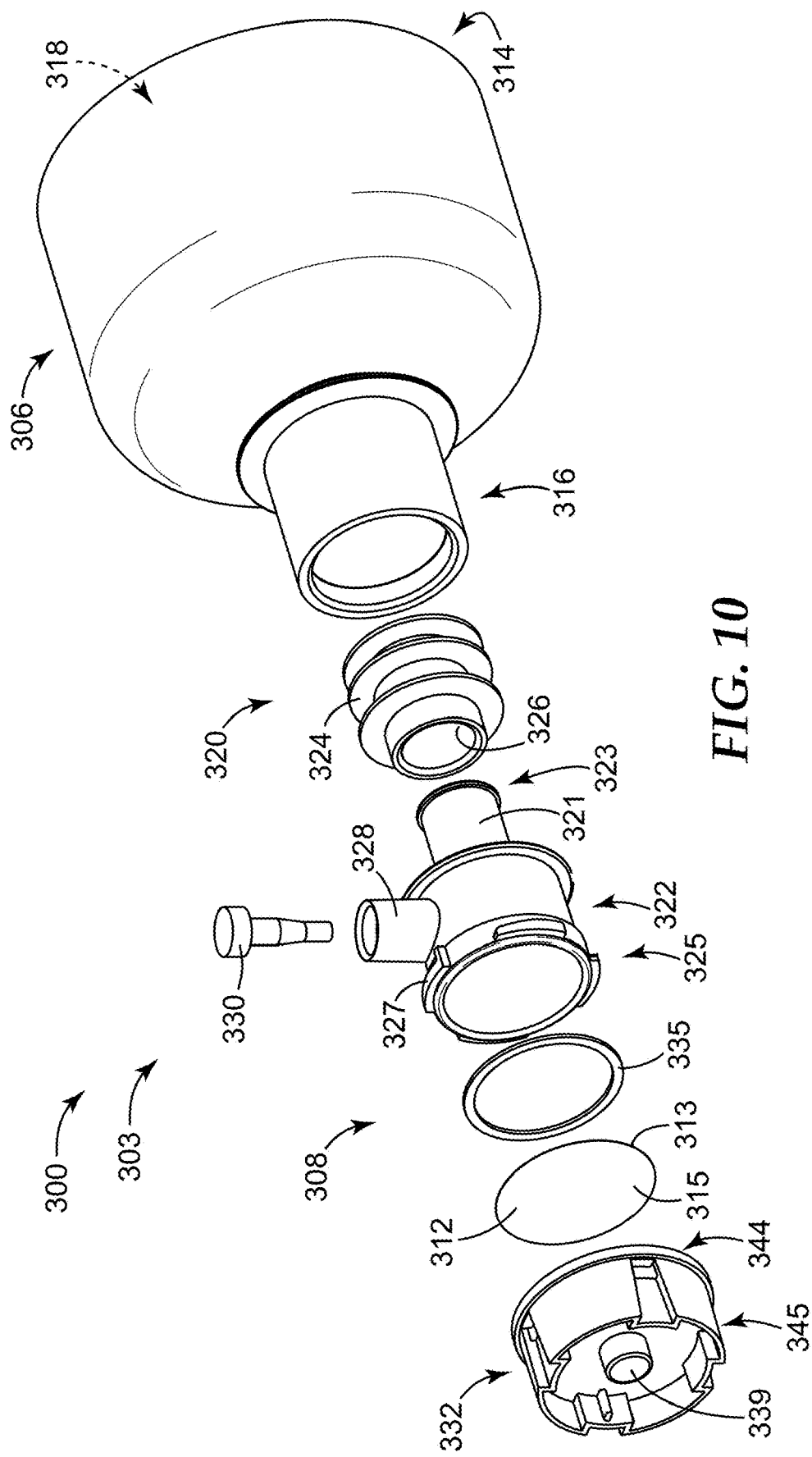
FIG. 10 is an exploded perspective view of a first container assembly of according to one embodiment of the present disclosure, the first container assembly comprising a receptacle portion and a filter portion.
Figure 11:
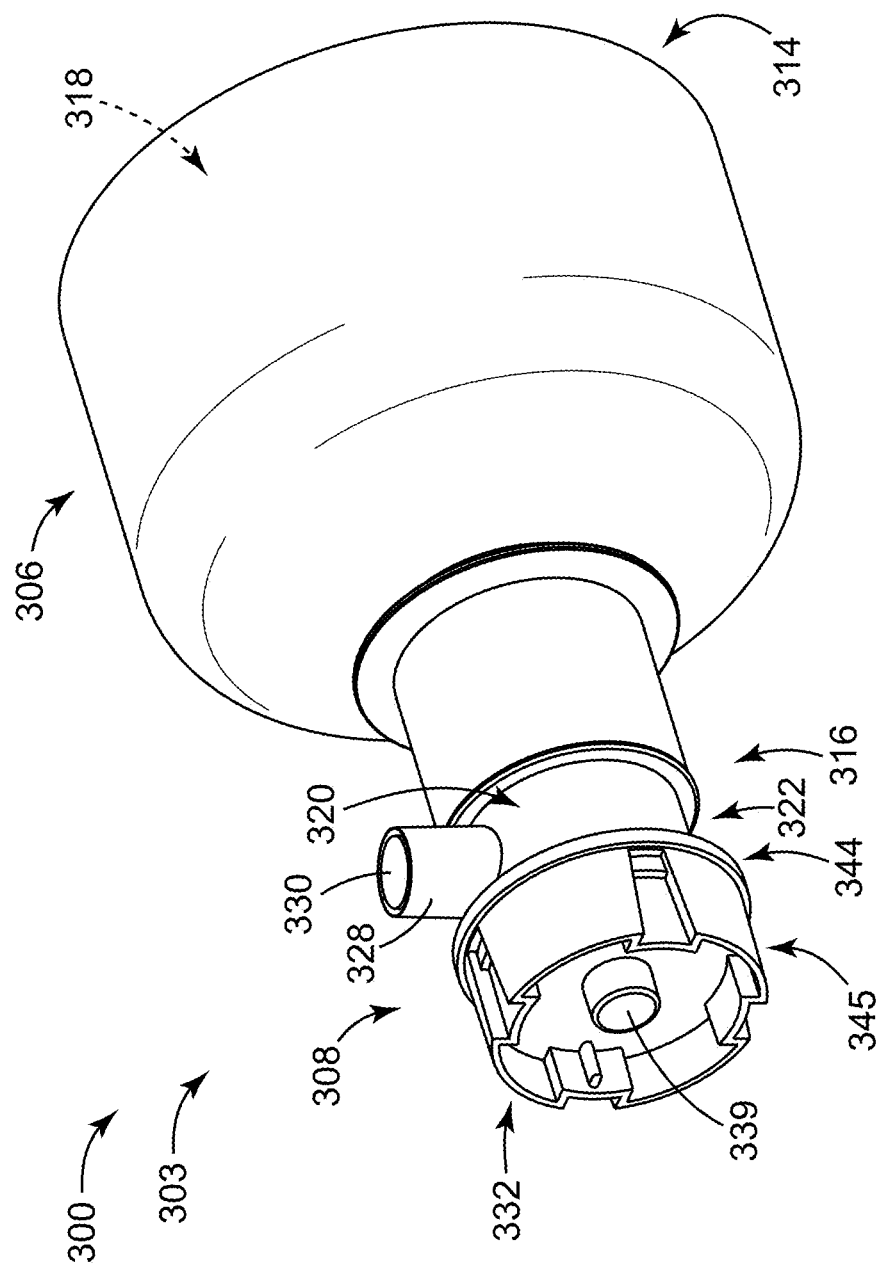
FIG. 11 is an assembled perspective view of the first container assembly of FIG. 10.
Figure 14:
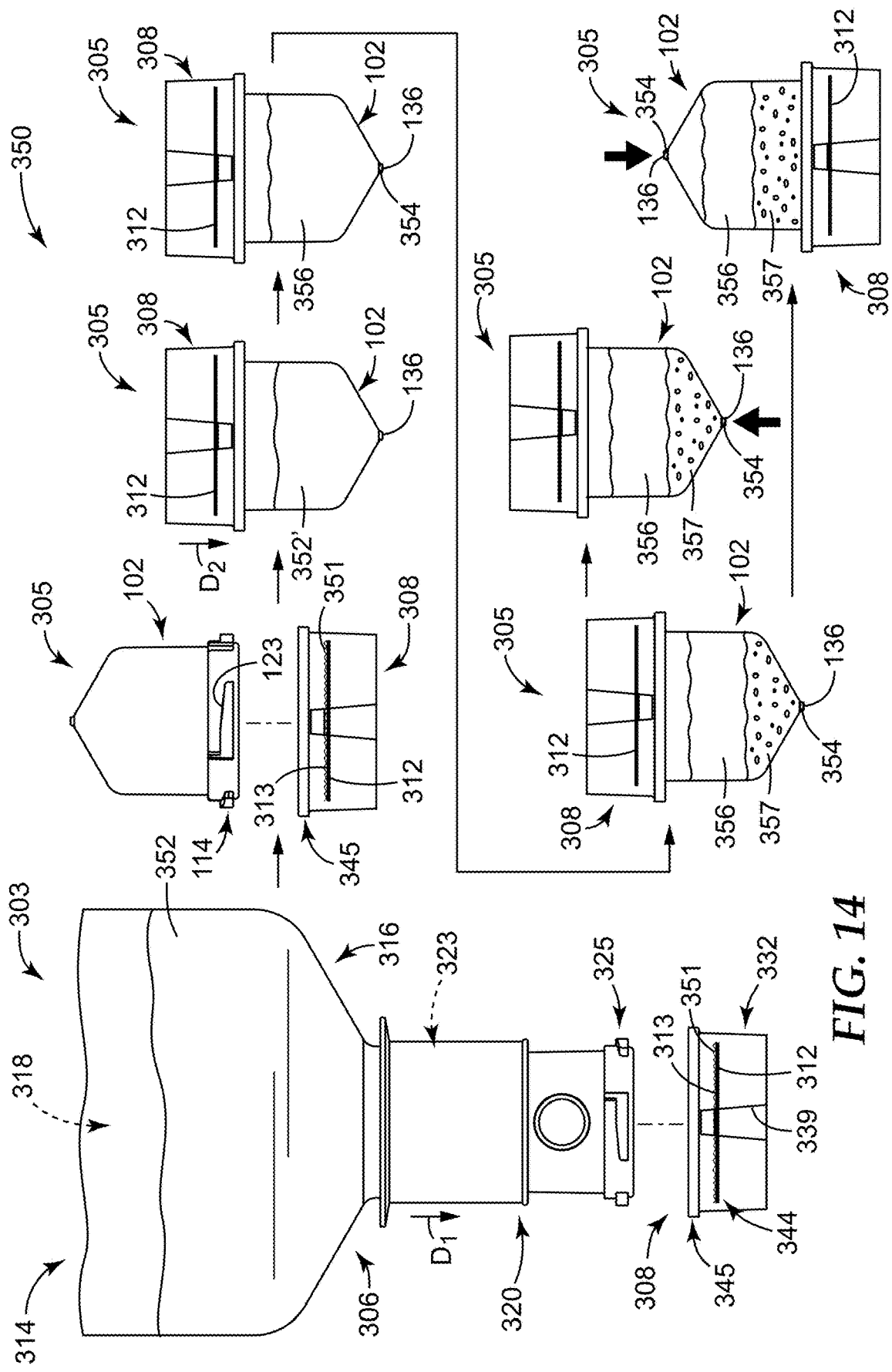
FIG. 14 illustrates a sample detection method according to another embodiment of the present disclosure, showing side elevational views of the first container assembly of FIGS. 10-11 and the second container assembly of FIGS. 12-13.

As shown in FIGS. 10, 11 and 14, the first container 303 can include a receptacle portion (or "first portion") 306 that is adapted to contain a sample (e.g., a large volume aqueous sample) and a filter portion (or "second portion") 308 that includes a filter 312 that can be configured to retain an analyte of interest from the sample, if present. The filter portion 308 and the receptacle portion 306 can be configured to be removably coupled together to form the first container 303.

Figure 12:
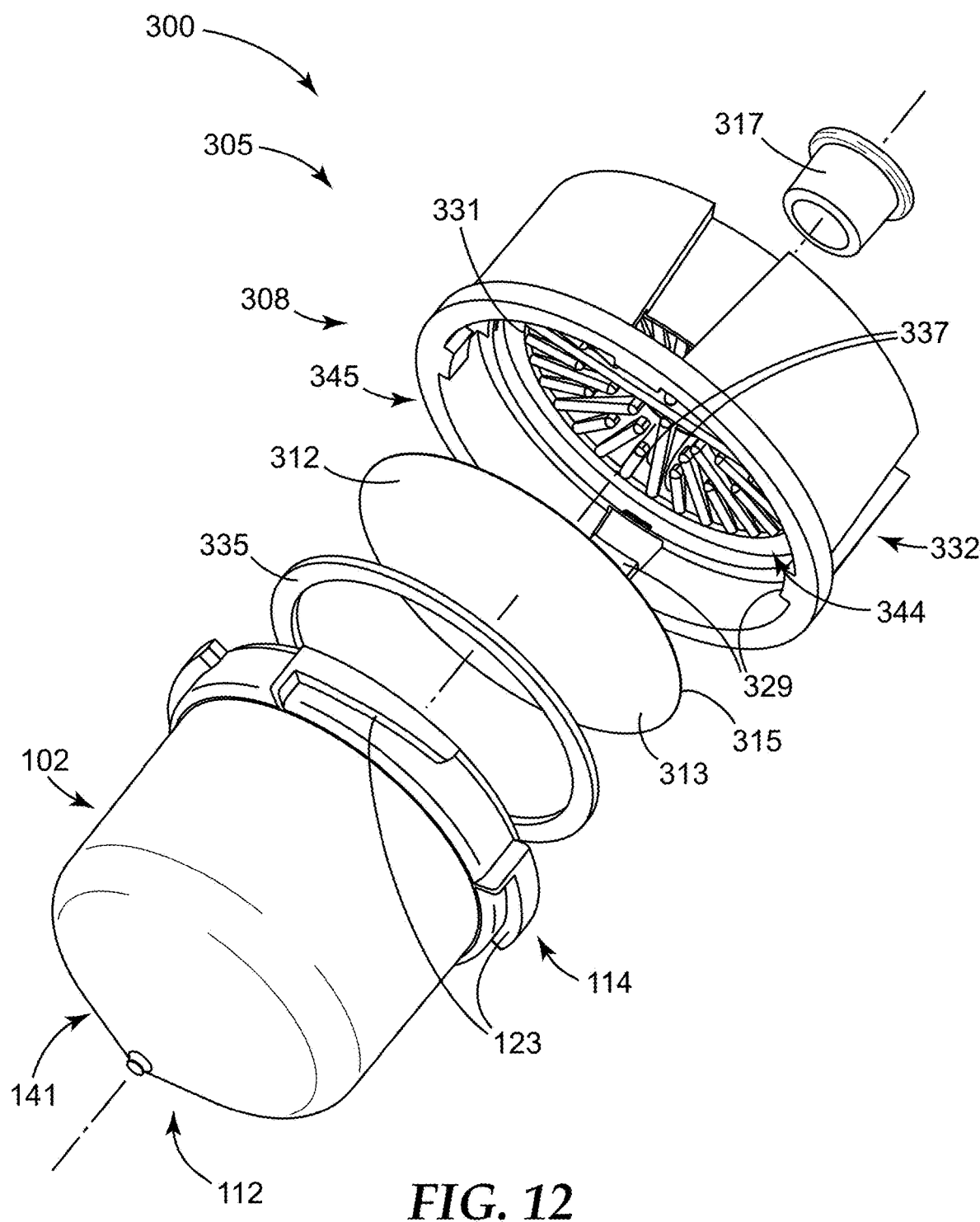
FIG. 12 is an exploded perspective view of a second container assembly according to one embodiment of the present disclosure, the second container assembly comprising the filter portion of FIGS. 10-11 and the sample detection container of FIGS. 1-3, 4 and 5.
Figure 13:
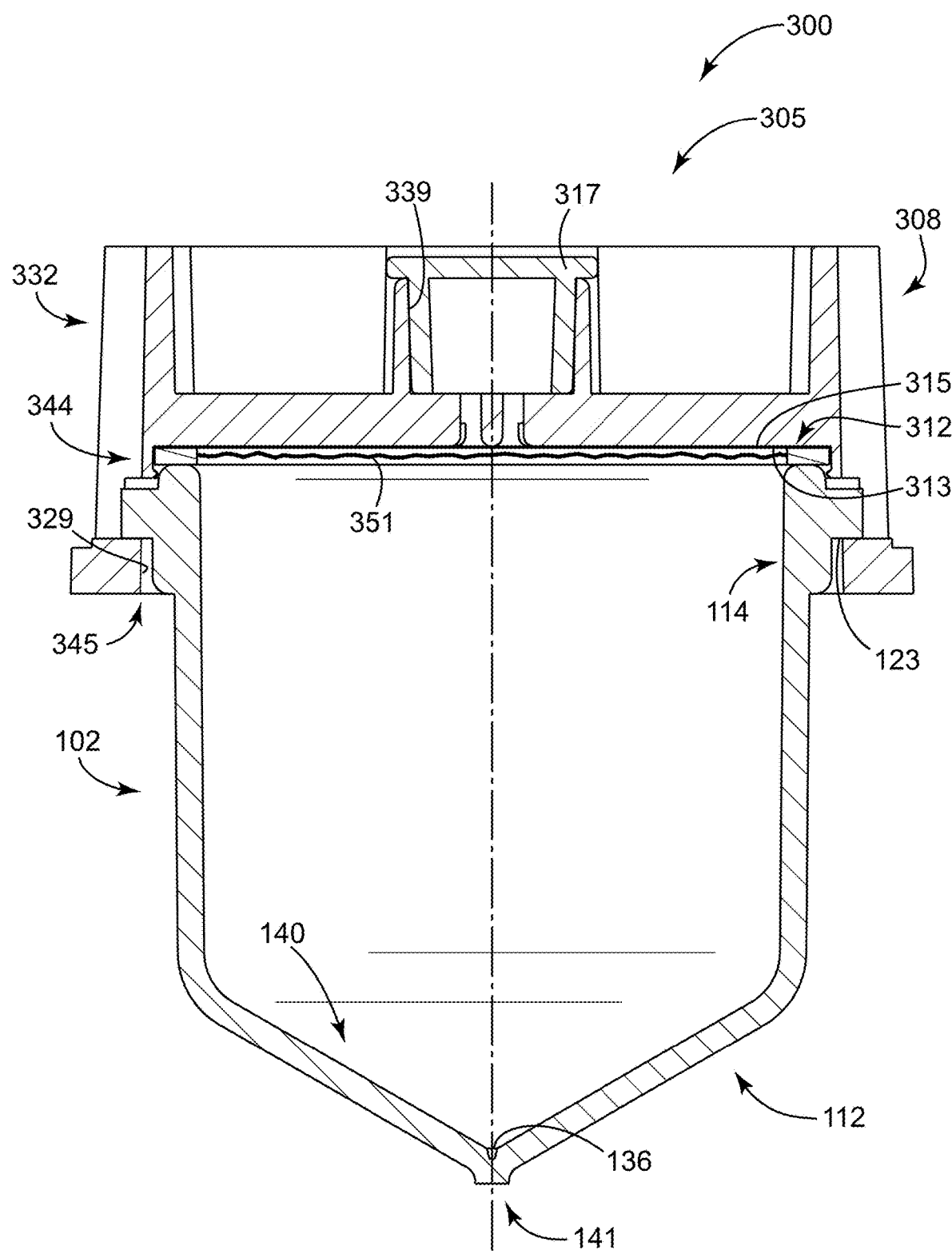
FIG. 13 is an assembled side cross-sectional view of the second container assembly of FIG. 12.

As shown in FIGS. 12-14, the second container 305 can include the filter portion 308 (i.e., the sample filter portion 308) and the sample detection container 102, which can also be referred to as "a detection portion" or "third portion." The filter portion 308 can therefore be used in both the first container 303 and the second container 305. As described above, the sample detection container 102 can include the microcavity 136 that is adapted to receive a concentrate of the sample when the second container 305 is exposed to a centrifugal force, and is further adapted to retain at least a portion of the concentrate of the sample under normal gravitational forces (e.g., under standard gravity, i.e., the standard value of Earth's gravitational acceleration at sea level, 9.8 m/s$^2$).

In general, the first container 303 can be used to filter the sample by passing the sample through the filter portion 308, and particularly, through the filter 312 to form a filtrate and a filtrand of the sample. The filter portion 308 can then be removed from the receptacle portion 306 of the first container 303 and coupled to the sample detection container 102 to form the second container 305. The second container 305 can then be centrifuged toward the microcavity 136 to move at least a portion of the filtrand from the filter 312 to the microcavity 136. In doing so, a sediment and a supernatant of the sample can be formed. The supernatant can be separated from the microcavity 136, for example, with a separation liquid, and a concentrate can be retained in the microcavity 136. The concentrate can comprise the sediment, which can include one or more analytes of interest, if present in the sample.

An exemplary sample detection method of the present disclosure will be described in greater detail below with reference to FIG. 14. The sample detection system 300 will now be described in greater detail.

The first container 303, and particularly, the receptacle portion 306, can be adapted to contain a sample that is to be analyzed, for example, for one or more analytes of interest. The first container 303 (or the receptacle portion 306) can be sized and shaped, as desired, to accommodate the sample to be analyzed, and the shape and configuration of the receptacle portion 306 and the filter portion 308 is shown by way of example only.

The receptacle portion 306 and the filter portion 308 can be formed of a variety of materials, including, but not limited to, the materials described above with respect to the sample detection container 102 and the cap 104 of FIGS. 1-3, 4 and 5. The receptacle portion 306, the filter portion 308, and the sample detection container 102 can be formed of the same or different materials.

The receptacle portion 306 can include a first end 314 that at least partially defines a reservoir 318, and a second end 316 configured to be coupled to the filter portion 308 (i.e., either directly or indirectly). The first end 314 can either be an open end or a closed end. By way of example only, in FIGS. 10 and 11, the first end 314 is closed and the second end 316 is open, such that a sample can be added to the reservoir 318 via the second end 316, e.g., prior to coupling the receptacle portion 306 to the filter portion 308. However, in some embodiments, the first end 314 can be open to allow a sample to be added to the reservoir 318 via the first end 314, and the first end 314 can remain open, or it can be closed by a cover or lid.

As shown in FIG. 10, the first container 303 can further include a filter connection assembly 320 for coupling the filter portion 308 and the receptacle portion 306 together. In some embodiments, the filter connection assembly 320 can be coupled (e.g., removably or permanently) to the receptacle portion 306, and in some embodiments, the filter connection assembly 320 can be integrally formed with the receptacle portion 306. By way of example only, the filter connection assembly 320 is illustrated in FIGS. 10 and 11 as being adapted to be coupled between the receptacle portion 306 and the filter portion 308.

As shown in FIG. 10, in some embodiments, the filter connection assembly 320 can include a connector 322 and a gasket 324. The gasket 324 can be configured to be coupled between the connector 322 and the receptacle portion 306. In some embodiments, as shown, the gasket 324 can be dimensioned to be received within the second end 316 of the receptacle portion 306 and can further include a bore or an aperture 326 dimensioned to receive a first end 323 of the connector 322. For example, bore 326 can be shaped and dimensioned to receive a connection tube 321 of the connector 322. Such a configuration can aid in creating a seal (e.g., a liquid-tight seal, a hermetic seal, or a combination thereof) between the receptacle portion 306 and the filter portion 308 to seal the interior of the first container 303 from ambience, while maintaining fluid communication between the receptacle portion 306 and the filter portion 308 via the aperture 326 formed therein. The shape and configuration of the gasket 324, the connector 322, and the second end 316 of the receptacle portion 306 are shown by way of example only; however, it should be understood that any shapes and configurations and relative structures of these elements can be employed to achieve the same function.

As mentioned above, the connector 322 can include a first end 323 configured to be coupled to the receptacle portion 306 and a second end 325 configured to be coupled to the filter portion 308. By way of example only, the second end 325 is shown as including threads 327 that are substantially the same as the threads or tracks 123 on the sample detection container 102 described above and shown in FIGS. 1 and 2. The threads 327 on the connector 322 cooperate and engage with protrusions 329 (see FIG. 12) of the filter portion 308 to allow the filter portion 308 to be screwed onto the filter connection assembly 320 for coupling to the filter connection assembly 320 and the receptacle portion 306. By way of example only (as shown in FIG. 12), the filter portion 308 (and particularly, a filter housing 332) can include protrusions 329 that are substantially the same as the protrusions 121 on the cap 104 of the sample detection system 100. In some embodiments, the receptacle portion 306 or the filter portion 308 can itself include all of the features of the filter connection assembly 320. Alternatively, in some embodiments, the receptacle portion 306 and the filter portion 308 can be configured to be coupled directly to one another.

The threaded connection between the filter portion 308 and the receptacle portion 306 (or between the filter portion 308 and the sample detection container 102) is shown by way of example only; however, in some embodiments, manufacturability may be enhanced by employing a friction-fit (e.g., press-fit) or snap-fit-type coupling means between these components.

As shown in FIGS. 10 and 11, the filter connection assembly 320 (e.g., the connector 322) can further include a vent port 328 and a filter plug 330 that can serve as an air inlet during the filtration process, particularly, in embodiments in which the first end 314 of the receptacle portion 306 is closed. The filter plug 330 can be used to filter inlet air as it enters the first container 303 during a filtration process. In some embodiments, the filter plug 330 can be formed of a hydrophobic material (e.g., polypropylene, polyethylene, polytetrafluoroethylene (PTFE), or a combination thereof) to inhibit sample leakage out of the vent port 328 and contamination into the vent port 328.

The filter portion 308 can include a filter housing 332 configured to house and retain the filter 312. By way of example only, as shown in FIG. 12, the filter 312 can be positioned against a first or upper surface 331 of the filter housing 332. As further shown in FIG. 12, the upper surface 331 of the filter housing 332 can include or at least partially define a plurality of apertures 337 that are in fluid communication with an outlet 339 (see FIGS. 10 and 11). Such an outlet 339 can function as the outlet of the first container 303 and/or of the filter portion 308, and can be coupled to a suction source (not shown) to perform the filtration step to move the sample through the receptacle portion 306, the filter connection assembly 320 (if employed), and the filter portion 308.

In some embodiments, the filter 312 (e.g., a periphery thereof) can be ultrasonically welded to the filter housing 332 (e.g., a ledge or flange within the housing 332 on which the periphery of the filter 312 will sit). Such an ultrasonic weld can provide a hermetic seal, in addition to providing means for coupling the filter 312 to the filter housing 332. Still, in some embodiments, the filter 312 can be integrally formed with the filter housing 332 or sandwiched between two mating parts.

The filter portion 308 (or the filter housing 332) can include a first end 344 that comprises the filter 312 and the outlet 339, and a second end 345 configured to be coupled (e.g., removably) to the receptacle portion 306 (i.e., directly, or indirectly, e.g., via the filter connection assembly 320) and the sample detection container 102, as described below. For example, as shown in FIG. 12, in some embodiments, the second end 345 can include the threads 329 for coupling with the threads 327 of the filter connection assembly 320 (or of the receptacle portion 306 if the filter connection assembly 320 is not employed) and the threads 123 of the sample detection container 102. In addition, by way of example only, in some embodiments, the second end 345 can be dimensioned to receive the second end 325 of the filter connection assembly 320 (or vice versa). Alternatively, if the filter connection assembly 320 is not employed, the second end 345 can be configured to be coupled directly to the receptacle portion 306.

In addition, as shown in FIGS. 10 and 12, in some embodiments, a gasket (e.g., an o-ring) 335 can be employed between the filter housing 332 (i.e., between the filter 312) and the filter connection assembly 320 (or the receptacle portion 306 if the filter connection assembly 320 is not employed) and/or between the filter housing 332 (i.e., between the filter 312) and the sample detection container 102. Such a gasket 335 can enhance the seal between the receptacle portion 306 (e.g., or the filter connection assembly 320) and the filter portion 308. By way of example only, the same gasket 335 is shown as being employed in the first container 303 (FIG. 10) and the second container 305 (FIG. 12); however, this need not be the case.

As mentioned above, the filter 312 can be configured to retain an analyte of interest from the sample, if present. The filter 312 can be configured either by size, charge, affinity, or other suitable means for retaining the analyte of interest.

Any of the above-described filters or membranes can be employed in the present disclosure.

Particularly, exemplary filters 312 can be made by, for example, TIPS (thermally induced phase separation) process, SIPS (solvent induced phase separation) process, VIPS (vapor induced phase separation) process, stretching process, track-etching, or electrospinning (e.g., PAN fiber membranes). Suitable membrane materials include, for example, polyolefins (e.g., polyethylene and/or polypropylene), ethylene-chlorotrifluoroethylene copolymer, polyacrylonitrile, polycarbonate, polyester, polyamide, polysulfone, polyethersulfone, polyvinylidene fluoride (PVDF), cellulose ester, and/or combinations thereof.

Suitable membranes may be characterized as porous membranes or as nanofiber membranes. Nanofiber filter membranes can have the fiber diameter less than 5 μm such as, for example, less than 1 μm. Nanofiber membranes may be prepared from, for example, polyacrylonitrile, polyvinylidene fluoride, a cellulose ester, polyvinyl acetate, polyvinyl alcohol, polyvinyl butyral, and/or combinations thereof.

Certain TIPS polyolefin membranes can be prepared so that they possess a single, homogeneous zone of membrane structure, each zone having a different pore microstructure. In other cases, a TIPS membrane may be prepared as a multi-zone membrane that includes two or more zones, each zone having a different pore microstructure. A multi-zone TIPS membrane may contain distinct zones or, alternatively, may possess a transition zone between two otherwise distinct zones. Such multi-zone filters can be particularly useful in the systems and methods of the present disclosure due to the efficient elution. In embodiments employing such multi-zone filters, the side of the filter comprising the smallest pore zone can be employed as a first side 313.

Exemplary filter membranes include membranes that are described in, for example, in U.S. Pat. Nos. 4,539,256, 4,726,989, 4,867,881, 5,120,594, 5,260,360, International Patent Publication No. WO2010/078234, International Patent Publication No. WO2010/071764, PCT Publication WO2011/152967, and PCT Publication WO2011/153085.

The filter 312 can include a first side 313 that faces the receptacle portion 306 during the filtration step and which faces the sample detection container 102 (and particularly, the microcavity 136) during the centrifugation step, and a second side 315 that faces the outlet 339. During filtration, the sample is separated into a filtrand 351 (see FIGS. 13 and 14) that is retained on the first side 313 of the filter 312 and a filtrate. As described above, the filtrate can either be discarded or can be re-run through the sample processing to try to obtain further analyte(s) of interest, or otherwise processed.

While the filtrand 351 may be described as being retained on the first side 313 of the filter 312, this does not necessarily mean that the filtrand 351 is not present in any of the depth of the filter 312 (as might be the case for a porous polymer film with a wide distribution of pore sizes). Rather, this means that the sample was filtered through the filter 312 from the first side 313 to a second (opposite) side, and that the first side 313 is the side of the filter 312 that faces both the receptacle portion 306 during filtration and the sample detection container 102 during centrifugation. It is possible that at least some of the filtrand may be present below the surface of the first side 313 of the filter 312, that is, at least partially into the depth of the filter 312. However, particular filters or types of filters (e.g., multi-zone filters, isoporous filters) can be employed to inhibit the sample from moving too far into the depth of the filter 312 that significant time and elution efforts are required to retrieve the filtrand 351 from the filter 312.

As shown in FIG. 14, the second end 345 of the filter portion 308 (e.g., the filter housing 332) and the second end 325 of the filter connection assembly 320 (or the second end 316 of the receptacle portion 306) can be coupled together, and oriented in a first orientation, e.g., upright. A sample 352 can be added to the reservoir 318 of the receptacle portion 306, the outlet 339 of the filter portion 308 can be coupled to a suction source, and the sample 352 can be filtered in a first direction $D_1$ toward the filter 312, a filtrate of the sample 352 moving out of the filter portion 308, and a filtrand 351 of the sample 352 being retained on the first side 313 of the filter 312.

In some embodiments, the receptacle portion 306 and the filter portion 308, or a portion thereof, can be substantially transparent, opaque (i.e., substantially non-transparent), or somewhere in between (e.g., translucent), and can be any suitable size, depending on the type, amount and/or size of sample to be analyzed, and the type, amount and/or size of concentrate to be collected and interrogated.

With reference to FIGS. 12-14, the second container 305 will now be described. As mentioned above, the second container 305 can include the filter portion 308 and the sample detection container 102. The sample detection container 102 can include the microcavity 136.

The first end 112 of the sample detection container 102 comprises the microcavity 136 and the second end 114 is configured to be coupled to the second end 345 of the filter portion 308. As shown in FIG. 12, in some embodiments, the second end 114 of the sample detection container 102 can be dimensioned to be received in the filter portion 308 (i.e., the filter housing 332), and the threads 123 can be configured to cooperate and engage with the protrusions 329 of the filter portion 308 in the same way that the threads 123 cooperated and engaged with the protrusions 121 of the cap 104 of the sample detection system 100 of FIGS. 1-3, 4 and 5. Such engagement can allow the sample detection container 102 and the filter portion 308 to be screwed together, and particularly, to be removably coupled together. In some embodiments, however, the filter portion 308 and the sample detection container 102 can be removably coupled together by other means (e.g., any of those described above). In some embodiments, the entire second container 305 can be disposable, and can be discarded following the detection process. It should be understood, however, that in some embodiments, the sample detection container 102 can instead be dimensioned to receive at least a portion of the filter housing 308.

By way of example only, the sample detection container 102 is illustrated as being the larger portion of the second container 305, such that the sample detection container 102 acts as the tube or reservoir of the second container 305, and the filter portion 308 acts as the cap or cover of the second container 305. However, it should be understood that the sizes, shapes, and relative sizes of the components of the second container 305 can be adjusted to suit a particular sample or situation.

The first side 140 (see FIGS. 2, 3 and 13) of the sample detection container 102 generally faces an interior of the second container 305, and the second side 141 of the sample detection container 102 generally faces an exterior of the second container 305. The second side 141 therefore also generally faces away from the filter portion 308. As a result, the concentrate retained in the sample detection container 102 can be interrogated from the second side 141, for example in embodiments in which at least a portion of the sample detection container 102 (e.g., the first (closed) end 112 and/or the second side 141) is substantially transparent. In some embodiments, at least a portion of the microcavity 136 (e.g., the base 146 thereof) can be substantially transparent to allow the contents of the microcavity 136 to be viewed, detected and/or interrogated from the second side 141.

As shown in FIGS. 12 and 13, in some embodiments, the outlet 339 of the filter portion 308 that is used in the filtration step to remove the filtrate and to perform a first sample concentration step can be sealed or closed, for example, by a cap 317. For example, the cap 317 can be coupled to the outlet 339 following the filtration step, and particularly when the filter portion 308 and the sample detection container 102 are coupled together to form the second container 305.

In some embodiments, the original sample volume (i.e., prior to any concentration steps, including filtration and/or centrifugation) to be tested for the analyte(s) of interest can be at least about 5 mL, in some embodiments, at least about 10 mL, in some embodiments, at least about 25 mL, in some embodiments, at least about 50 mL, in some embodiments, at least about 100 mL, in some embodiments, at least about 500 mL, in some embodiments, at least about 1 L, in some embodiments, at least about 2 L, in some embodiments, at least about 5 L, and in some embodiments, at least about 10 L.

In some embodiments, the volume of the sample detection container 102 or the second container 305 can range from about 1 mL to about 250 mL. As a result, in some embodiments, the volume of the sample (e.g., a sample formed from the filtrand 351 of the original sample 352 and one or more diluents that are added post-filtration) can be at least about 1 mL, in some embodiments, at least about 10 mL, and in some embodiments, at least about 100 mL. In some embodiments, the volume of the sample is no greater than about 200 mL, in some embodiments, no greater than about 100 mL, in some embodiments, no greater than about 75 mL, and in some embodiments, no greater than about 50 mL. In some embodiments, the volume of the sample ranges from about 1 mL to about 100 mL.

In some embodiments, the ratio of the volume of the sample detection container 102 or the second container 305 to the volume of the concentrate (or retentate) of the sample that is retained in the sample detection container 102 is at least 100:1 ($10^2$:1), in some embodiments, at least about 1000:1 ($10^3$:1), in some embodiments, at least about 10,000:1 ($10^4$:1), in some embodiments, at least about 100,000:1 ($10^5$:1); in some embodiments, at least about $10^8$:1; in some embodiments, at least about $10^9$:1; in some embodiments, at least about $10^{10}$:1, and in some embodiments, at least about $10^{11}$:1. In some embodiments, the ratio of the volume of the sample detection container 102 or the second container 305 to the volume of the concentrate that is retained in the sample detection container 102 ranges from about 100:1 to about $10^{11}$:1.

As with the sample detection system 100 of FIGS. 1-3, 4 and 5, in some embodiments, the concentration increase (i.e., the concentration (e.g., of the more dense matter, such as the analyte(s) of interest) of the resulting concentrate retained in the sample detection container 102, divided by the concentration of the initial sample (either before or after filtration), expressed as a ratio) can be at least about 100:1 ($10^2$:1), in some embodiments, at least about 1000:1 ($10^3$:1), in some embodiments, at least about 10,000:1 ($10^4$:1), and in some embodiments, at least about 100,000:1 ($10^5$:1). In some embodiments, the concentration efficiency ranges from about 10:1 to about $10^5$:1.

In some embodiments, the receptacle portion 306 of FIGS. 10 and 11 can have a capacity of at least about 1 mL, at least about 5 mL, at least about 10 mL, at least about 25 mL, at least about 50 mL, at least about 100 mL, or at least about 250 mL. That is, in some embodiments, the capacity, or volume, of the receptacle portion 306 can range from about 1 mL to about 250 mL, and in some embodiments, can range from about 1 mL to about 100 mL. In some embodiments, the filter portion 308, the sample detection container 102, and/or the second container 305 can have a capacity of no greater than about 1 mL, no greater than about 2 mL, no greater than about 5 mL, or no greater than about 10 mL.

The shapes, dimensions and coupling means for the receptacle portion 306, the filter portion 308, and the sample detection container 102 are described above and illustrated in FIGS. 10-14 by way of example only. It should be understood, however, that a variety of shapes and dimensions of the receptacle portion 306, the filter portion 308, and the sample detection container 102 can be used. In addition, a variety of coupling means can be employed to removably and/or permanently couple the receptacle portion 306 and the filter portion 308, as well as the filter portion 308 and the sample detection container 102, including, but not limited to, screw threads (as shown), a clamp (e.g., a spring-loaded clamp, a snap-type clamp, etc.); a clip (e.g., a spring-loaded clip, etc.); ties (e.g., wire ties); one or more magnets; tape; an adhesive; a cohesive; a hook-and-loop fastener; snap-fit engagement (e.g., wherein the filter housing 308 functions as a flip-top cap); press-fit engagement (also sometimes referred to as "friction-fit engagement" or "interference-fit engagement"); thermal bonding (e.g., heat and/or pressure applied to one or both of the components to be coupled); welding (e.g., sonic (e.g., ultrasonic) welding); other suitable coupling means; and combinations thereof.

With reference to FIG. 14, a sample detection method 350 will now be described, with continued reference to the sample detection system 300 of FIGS. 10-13, with the microcavity 136 shown schematically for illustration purposes.

The first step, i.e., the filtration step, of the sample detection method 350 was described above with respect to the first container 303. The filtration step can sometimes be referred to as a first concentration step of the sample detection method 350, and the following centrifugation step can sometimes be referred to as a second concentration step, such that the sample detection method 350 can be described as including two concentration steps to achieve a concentrate of the sample that can be interrogated for the analyte(s) of interest.

The filtrand 351 of the sample 352 that is retained on the first side 313 of the filter 312 can then be retrieved from the filter 312 using a variety of means, including, but not limited to, elution, agitation, washing, other suitable means for retrieving the filtrand 351 form the filter 312, or combinations thereof. For example, in some embodiments, retrieving the filtrand 351 can include adding one or more diluents (e.g., an elution solution and/or a wash solution) to the filter portion 308 (or the second container 305). An elution solution can be configured for eluting the filtrand 351 from the filter 312, for example, by disrupting any affinity between the filtrand 351 and the filter 312. In some embodiments, after one or more diluents are added to the filter portion 308, the sample detection container 102 can be coupled to the filter portion 308 to form the second container 305, and the second container 305 can be agitated to assist in removing the filtrand 351 from the filter 312. A new "sample" 352' can thus be formed comprising the filtrand 351 and any diluents that are added.

Particularly, in the embodiment illustrated in FIGS. 10-14, in forming the second container 305, the second (open) end 114 of the sample detection container 102 can be inserted into the second (open) end 345 of the filter portion 308, and the protrusions 329 (see FIG. 12) of the filter portion 308 and the threads 123 of the sample detection container 102 can be screwed together.

As shown in the third step of FIG. 14, the second container 305 can then be inverted to a second orientation and centrifuged in a second direction (or orientation) $D_2$ toward the sample detection container 102 (see the fourth step of FIG. 14). Such a centrifugation process can cause a concentrate 354 comprising the more dense matter of the original sample 352 (and the filtered sample 352') to be moved into the sample detection container 102, and particularly, into the microcavity 136 formed in the sample detection container 102. The "concentrate" 354 can generally include a sediment of the sample 352, 352' that is formed as a result of the centrifugation process, but can also include at least some of the supernatant, or diluent, of the sample 352, 352', as described above. The centrifugation step shown in the fourth step of FIG. 14 can generally follow the centrifugation step 150B of FIG. 4 described above.

As shown in the fifth step of FIG. 14, one or more separation liquids 357 can then be added to the sample detection container 102. For example, the filter portion 308 can be temporarily removed from the sample detection container 102 to add the separation liquid 357, and then the second container 305 can be reclosed by coupling the filter portion 308 to the sample detection container 102.

As shown in the fifth step of FIG. 14, the separation liquid 357 effectively displaces the supernatant 356 located outside of the microcavity 136 from the microcavity 136, such that the concentrate 354 of the sample 352, 352' is retained in the microcavity 136. That is, the separation liquid 357 moves between the concentrate 354 located in the microcavity 136 and a remainder of the sample in the sample detection container 102, such that the separation liquid 357 effectively isolates the concentrate 354 contained in the microcavity 136 from a bulk supernatant 356.

As further shown in FIG. 14 (i.e., by two alternative sixth steps in the method 350), the concentrate 354 in the microcavity 136 can then be interrogated (e.g., optically interrogated), or alternatively, inverted and then interrogated. Interrogation is represented in the last two alternative steps of FIG. 14 by large arrows. As shown in the first alternative interrogation step, the supernatant 356 and separation liquid 357 can remain above the microcavity 136 (i.e., covering the top opening thereof) during interrogation.

As shown in the second alternative interrogation step, the sample detection container 102 (i.e., the second container 305) can be inverted, e.g., prior to detection, such that the supernatant 356 resulting from the centrifugation step and the separation liquid 357 is decanted from the microcavity 136, while the concentrate 354 remains retained in the microcavity 136. The inverting step shown in the second alternative sixth step of FIG. 14 can generally follow the inverting step 150E of FIG. 4 described above.

As described above, the sample detection container 102, or at least a portion thereof, can be substantially transparent, and the separation liquid 357 can be colorless, in order to enable interrogating (e.g., optically) the concentrate 354 from any desired orientation. The two alternative interrogation (or detection) steps of FIG. 14 can generally follow the two alternative interrogation steps 150D and 150E of FIG. 4 described above.

As further shown in the second alternative interrogation step, because the separation liquid 357 is denser than the supernatant 356, the separation liquid 357 moves toward the filter portion 308 when the second container 305 is inverted.

In some embodiments, particularly when the second container 305 is inverted, the supernatant 356, can be removed from the second container 305 and discarded or used in subsequent processing steps (e.g., repeated centrifugation steps).

The sample detection method 350 illustrated in FIG. 14, respectively, and described above can provide efficient collection and isolation of the concentrate 354 of the sample 352, 352' (i.e., and any analyte(s) of interest that may be present in the sample 352, 352') with minimal loss of the sample 352, 352' and/or the concentrate 354. For example, efficient collection can be achieved by essentially "trapping" the concentrate 354 (comprising the analyte(s) of interest, if present) in the sample detection container 102 during the centrifugation step illustrated in fourth step of FIG. 14 and the subsequent addition of the separation liquid 357. The concentrate 354 can generally have a much higher concentration than the sample 352, 352' of any analyte(s) of interest that may have been present in the sample 352, 352'.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

The following embodiments are intended to be illustrative of the present disclosure and not limiting.

EMBODIMENTS

1. A sample detection container adapted to contain and concentrate a sample for detection of an analyte of interest, if present, the container comprising:
   an open end configured to receive a sample;
   a closed end that includes a microcavity, the microcavity including a top opening and a base and configured to provide capillary forces to retain a sample of interest, wherein the microcavity includes a concentrate of a sample resulting from centrifugation of the sample, and wherein the concentrate includes a sediment and at least a portion of a supernatant; and
   a separation liquid located in the container above the microcavity, wherein the separation liquid is positioned between the microcavity and the supernatant located outside of the microcavity;
   wherein the separation liquid has a density greater than that of the supernatant of the sample and an interfacial tension with the supernatant of at least 0.05 N/m, and
   wherein the separation liquid is non-toxic and inert.

2. A method for detecting an analyte of interest in a sample, if present, the method comprising:
   providing a sample detection container comprising:
      an open end configured to receive a sample, and
      a closed end that includes a microcavity, the microcavity including a top opening and a base and configured to provide capillary forces to retain a sample of interest;
   positioning a sample in the sample detection container;
   centrifuging the sample detection container toward the microcavity to form a sediment and a supernatant of the sample;
   adding a separation liquid to the sample detection container, after centrifuging the sample detection container, to displace the supernatant located outside of the microcavity from the microcavity, such that a concentrate of the sample is retained in the microcavity, the concentrate comprising the sediment, wherein the separation liquid moves between the microcavity and the supernatant located outside of the microcavity;
   wherein the separation liquid has a density greater than that of the supernatant of the sample and an interfacial tension with the supernatant of at least 0.05 N/m, and
   wherein the separation liquid is non-toxic and inert.

3. The sample detection container of embodiment 1 or the method of embodiment 2, wherein the separation liquid has a density of at least 1.2 g/ml.

4. The sample detection container of embodiment 1 or 3 or the method of embodiment 2 or 3, wherein the separation liquid has a density of at least 0.2 g/ml greater than water.

5. The sample detection container of any of embodiments 1 and 3-4 or the method of any of embodiments 2-4, wherein the separation liquid has a surface tension of no greater than 0.02 N/m.

6. The sample detection container of any of embodiments 1 and 3-5 or the method of any of embodiments 2-5, wherein the separation liquid has an interfacial tension with the supernatant of at least 0.055 N/m.

7. The sample detection container of any of embodiments 1 and 3-6 or the method of any of embodiments 2-6, wherein the sample is aqueous, and wherein the separation liquid has an interfacial tension with water of at least 0.05 N/m.

8. The sample detection container of any of embodiments 1 and 3-7 or the method of any of embodiments 2-7, wherein the sample is aqueous, and wherein the separation liquid has an interfacial tension with water of at least 0.055 N/m.

9. The sample detection container of any of embodiments 1 and 3-8 or the method of any of embodiments 2-8, wherein the separation liquid has a solubility in water of less than 1%.

10. The sample detection container of any of embodiments 1 and 3-9 or the method of any of embodiments 2-9, wherein the separation liquid is colorless.

11. The sample detection container of any of embodiments 1 and 3-10 or the method of any of embodiments 2-10, wherein the separation liquid includes a fluorocarbon-based liquid.

12. The sample detection container of any of embodiments 1 and 3-11 or the method of any of embodiments 2-11, wherein the microcavity is a single microcavity.

13. The sample detection container of any of embodiments 1 and 3-11 or the method of any of embodiments 2-11, wherein the microcavity is one of a plurality of microcavities.

14. The sample detection container of any of embodiments 1 and 3-13 or the method of any of embodiments 2-13, wherein the microcavity is adapted to receive a concentrate of the sample when the container is subjected to a centrifugal force, and wherein the microcavity is further adapted to retain at least a portion of the concentrate of the sample under normal gravitational forces.

15. The sample detection container of any of embodiments 1 and 3-14 or the method of any of embodiments 2-14, wherein the sample detection container is formed of at least one of a polyolefins, cyclic olefin copolymers, polycarbonate, acrylic, polystyrene, other suitable polymeric materials or a combination thereof.

16. The sample detection container of any of embodiments 1 and 3-15 or the method of any of embodiments 2-15, wherein the microcavity contains a volume of no greater than 1 microliter.

17. The sample detection container of any of embodiments 1 and 3-16 or the method of any of embodiments 2-16, wherein the microcavity has a frustoconical shape or a frustopyramidal shape.

18. The sample detection container of any of embodiments 1 and 3-17 or the method of any of embodiments 2-17, and wherein the microcavity includes a sidewall, and wherein the sidewall includes a draft angle of at least 10 degrees.

19. The sample detection container of any of embodiments 1 and 3-18 or the method of any of embodiments 2-18, wherein an inner surface of the container has a static water surface contact angle of at least 65 degrees.

20. The sample detection container of any of embodiments 1 and 3-19 or the method of any of embodiments 2-19, wherein an inner surface of the container has a dynamic receding water surface contact angle of at least 25 degrees.

21. The sample detection container of any of embodiments 1 and 3-20 or the method of any of embodiments 2-20, wherein an inner surface of the container has a surface roughness characterized by a roughness average (Ra) value of less than 500 nm.

22. The sample detection container of any of embodiments 1 and 3-21 or the method of any of embodiments 2-21, wherein the base of the microcavity is substantially transparent, such that the contents of the microcavity are visible from outside the sample detection container.

23. The sample detection container or method of embodiment 22, wherein a sidewall of the microcavity is substantially non-transparent.

24. The sample detection container of any of embodiments 1 and 3-23 or the method of any of embodiments 2-23, wherein the microcavity comprises a reagent.

25. The sample detection container or method of embodiment 24, wherein the reagent includes at least one of a substrate, an enzyme, a growth reagent, a lysis reagent, or a combination thereof.

26. The sample detection container of any of embodiments 1 and 3-25 or the method of any of embodiments 2-25, wherein the analyte of interest includes at least one of *E. coli* and coliforms.

27. The sample detection container of any of embodiments 1 and 3-26 or the method of any of embodiments 2-26, wherein the sample is water.

28. A system for detecting an analyte of interest in a sample, if present, the system comprising:
  a first container assembly comprising a filter portion, the filter portion comprising a filter, the filter having a first side and comprising a filtrand of the sample on the first side; and
  a second container assembly comprising the filter portion coupled to the sample detection container of any of embodiments 1-27, the filter portion and the sample detection container being coupled together such that the first side of the filter faces the microcavity of the sample detection container.

29. The method of embodiment 2, wherein positioning a sample in the sample detection container includes:
  providing a first container assembly comprising a filter portion, the filter portion comprising a filter configured to retain the analyte of interest from the sample, the filter having a first side and comprising a filtrand of the sample on the first side; and
  coupling the filter portion to the sample detection container to form a second container assembly, the filter portion and the sample detection container being coupled together such that the first side of the filter faces the microcavity of the sample detection container.

30. The method of embodiment 2, wherein positioning a sample in the sample detection container includes:
  providing a first container assembly comprising a receptacle portion adapted to contain the sample and a filter portion adapted to be removably coupled to the receptacle portion, the filter portion comprising a filter configured to retain the analyte of interest from the sample, the filter having a first side;
  filtering the sample by moving the sample in a first direction from the receptacle portion toward the first side of the filter to form a filtrand of the sample on the first side of the filter, while removing a filtrate of the sample; and
  decoupling the receptacle portion and the filter portion of the first container assembly;
  coupling the filter portion to the sample detection container to form a second container assembly, the filter portion and the sample detection container being coupled together such that the first side of the filter faces the microcavity of the sample detection container.

31. The method of embodiment 2, 29 or 30, further comprising interrogating the concentrate in the microcavity for the analyte of interest.

32. The method of embodiment 31, further comprising incubating the sample detection container prior to interrogating.

33. The method of embodiment 31 or 32, wherein the analyte of interest, if present, is detected in the microcavity in less than 3 hours.

34. The method of any of embodiments 31-33, wherein interrogating the concentrate in the microcavity includes interrogating for at least one of absorbance, transmittance, fluorescence, chemiluminescence, and a combination thereof.

35. The method of any of embodiments 2 and 29-34, wherein interrogating the concentrate in the microcavity includes optically interrogating the concentrate in the microcavity.

36. The method of embodiment 35, wherein optically interrogating includes interrogating the concentrate in the microcavity for fluorescence.

37. The method of embodiment 35 or 36, wherein optically interrogating includes
  directing electromagnetic energy toward the concentrate in the microcavity at a first frequency, and
  detecting electromagnetic energy emitted from the concentrate in the microcavity at a second frequency.

38. The method of embodiment 35, wherein optically interrogating includes interrogating the concentrate colorimetrically.

39. The method of embodiment 35 or 38, wherein optically interrogating includes emitting electromagnetic energy at the concentrate in the microcavity at a broad range of frequencies, and detecting at least one of the transmittance and the absorbance of at least a portion of the concentrate in the microcavity.

40. The method of any of embodiments 35-39, wherein optically interrogating the concentrate in the microcavity includes optically scanning the microcavity.

41. The method of any of embodiments 35-40, wherein optically interrogating the concentrate in the microcavity includes imaging the microcavity.

42. The method of any of embodiments 31-41, wherein interrogating the concentrate in the microcavity includes detecting light that is indicative of the analyte of interest.

43. The method of any of embodiments 31-42, wherein interrogating the concentrate in the microcavity includes detecting light by absorbance, reflectance, or fluorescence.

44. The method of any of embodiments 31-43, wherein interrogating the concentrate in the microcavity includes detecting the analyte of interest immunologically.

45. The method of any of embodiments 31-44, wherein interrogating the concentrate in the microcavity includes detecting the analyte of interest genetically.

46. The method of any of embodiments 31-45, wherein interrogating the concentrate in the microcavity includes detecting an enzyme released from a live cell in the sample.

47. The method of any of embodiments 31-46, wherein interrogating the concentrate in the microcavity includes detecting the analyte of interest colorimetrically, fluorimetrically, luminetrically, or a combination thereof.

48. The method of any of embodiments 31-47, wherein the microcavity is formed in a first side of the sample detection container and the first side is positioned to face the filter portion during centrifugation, wherein the sample detection container further comprises a second side opposite the first side, and wherein interrogating the concentrate in the microcavity includes interrogating the concentrate in the microcavity from the second side of the sample detection container.

49. The method of embodiment 48, wherein the second side of the detection portion includes an optical window that is substantially transparent.

50. The method of embodiment 48 or 49, wherein the optical window is coextensive with at least a portion of the microcavity.

51. The method of any of embodiments 31-50, wherein the filter portion and the sample detection container of the second container assembly remain coupled together during the interrogating step.

52. The method of any of embodiments 31-51, wherein the supernatant and the separation liquid reside above the microcavity in the second container assembly during the interrogating step.

53. The method of any of embodiments 2 and 29-52, wherein the method does not include inverting the sample detection container to decant at least a portion of the supernatant from the microcavity.

54. The method of any of embodiments 2 and 29-52, further comprising inverting the sample detection container to decant the separation liquid and the supernatant located outside of the microcavity from the microcavity.

55. The method of any of embodiments 29-54, further comprising adding an elution solution to the filter portion, the elution solution adapted to elute the filtrand from the filter.

56. The method of embodiment 55, wherein adding an elution solution to the filter portion occurs prior to coupling the filter portion to the sample detection container to form a second container assembly.

57. The method of any of embodiments 29-55, further comprising agitating at least the filter portion of the second container assembly prior to centrifuging, wherein agitating aids in removing the filtrand from the filter.

58. The method of any of embodiments 29-57, further comprising adding a diluent to the filter portion prior to centrifuging the second container assembly.

59. The method of any of embodiments 29-58, further comprising agitating the second container assembly prior to centrifuging the second container assembly.

60. The method of embodiment 59, wherein agitating occurs when the second container assembly is in a first orientation, and wherein centrifuging occurs in a second orientation, wherein the second orientation is different from the first orientation.

61. The method of any of embodiments 29-60, further comprising incubating the second container assembly prior to centrifuging to grow microorganisms in the sample, if present.

62. The system of embodiment 28 or the method of any of embodiments 29-61, wherein the filter includes at least one of a polyolefin porous membrane, an ethylene-chlorotrifluoroethylene copolymer porous membrane, a polyacrylonitrile porous membrane, a polycarbonate porous membrane, a polyester porous membrane, a cellulose ester porous membrane, a polyamide porous membrane, a polyethersulfone porous membrane, a polysulfone porous membrane, a polyvinylidene fluoride (PVDF) porous membrane, a polyacrylonitrile nanofiber membrane, a PVDF nanofiber membrane, a cellulose ester nanofiber membrane, a polyvinyl acetate or alcohol nanofiber membrane, or a polyvinyl butyral nanofiber membrane, or a combination thereof.

63. The system of embodiment 28 or 62 or the method of any of embodiments 29-62, wherein the filter includes at least one of
    a membrane formed by a thermally induced phase separation (TIPS) process, and
    a nanofiber membrane.

64. The system of any of embodiments 28 and 62-63 or the method of any of embodiments 29-63, wherein the filter includes multiple zones of porosity, and wherein the first side of the filter comprises the smallest pore zone.

The following working and prophetic examples are intended to be illustrative of the present disclosure and not limiting.

EXAMPLES

Definitions

SMD: Single microcavity device

MS: Microcavity Surface, a surface comprising a plurality of microcavities

Microcavity: A microcavity is a well formed in a thermoplastic or thermoset material. Each microcavity is characterized by a two-dimensional (e.g., cross-sectional) shape (e.g., square, hexagon, circle) having a top opening, one or more sidewalls and a base (or bottom). The approximate volume of the microcavity is calculated by:

$$V = \tfrac{1}{3} h (A_1 + A_2 + \sqrt{A_1 \cdot A_2})$$

where, h is the depth/height, $A_1$ the area of the base, and $A_2$ the area of the top opening.

The volume of is calculated by summing (i) the area of the base, (ii) the area of the top opening, and (iii) the square root of the product of (i) and (ii); and then multiplying the sum by the depth (height), and dividing by 3.

Onset: the time at which fluorescence is first observed on an image. Images of the microcavities are taken at fixed intervals, e.g., after 1 hour, 2 hours, 3 hours, etc. The times recorded in the examples represent the time at which the fluorescence was first observed in an image. The actual onset is a time between the image exhibiting fluorescence and the previous image.

Materials and Instruments

COC-S-04—transparent cyclic olefin copolymer, high moisture barrier; TOPAS®8007S-04; Topas Advanced Polymers Gmbh; Florence Ky.

PMMA—WF100 poly(methyl methacrylate); Mitsubishi Rayon Co Ltd, Tokyo, Japan

COLILERT® media—COLILERT® coliform/*E. coli* test media; IDEXX Laboratories, Inc.; Westbrook, Me. The media was prepared for the examples by mixing the media from a Snap Pack for a 100 mL sample in 100 mL of sterile water.

Filter A—30 mm diameter to fit device used, 0.34 μm multi-zone TIPS membrane coated with polyethylene glycol (R1933-7/PEG) prepared according the examples and description of WO2011/156251). The membranes were coated with polyethylene glycol (PEG) using the materials and procedures described in WO2011/153085.

Filter B—30 mm diameter to fit device used, Isopore Membrane, polycarbonate—0.40 μm; Millipore, Billerica, Mass.

Filter C—30 mm diameter to fit device used, MF-Millipore Membrane, Type HAWP—mixed cellulose ester—0.45 μm; Millipore; Billerica Mass.

Multipurpose Centrifuge—multipurpose centrifuge (Model 5810R) with a swinging bucket rotor (A-4-81), both manufactured by Eppendorf; Hauppauge N.Y.

Multipurpose Centrifuge—multipurpose centrifuge (Model 5804) with a swinging bucket rotor (A-4-44), both manufactured by Eppendorf; Hauppauge N.Y.

Imaging system 1—illuminated/fluorescent stereo microscope model SteREO Lumar.V12 using either illuminated light (Illuminated Imager) or fluorescent light (Fluorescent Imager); images were captured with an AxioCam MRc 5 camera and the AxioVision Release 4.6.3 program, all obtained from Carl Zeiss Microimaging, Inc., Thornwood N.J.

Imaging system 2—illuminated/fluorescent inverted microscope model DMI6000B using either illuminated light (Illuminated Imager) or fluorescent light (Fluorescent Imager); images were captured with a DFC365FX camera and the LAS AF 3.1.0 software, all obtained from Leica Microsystems, Inc., Buffalo Grove, Ill.

Vacuum assembly—AIR CADET Vacuum/Pressure Station, model No. 420-3901; Thermo Fisher Scientific Inc., Waltham, Mass.

Preparation of Sample Detection Containers

1—Injection Molded 1.5 ml Sample Detection Containers with a Single Microcavity (SMD1-SMD2)

Precision machining was used to make insert tools comprising a single microcavity for injection molding 1.5 ml containers having a single microcavity. Initially a CAD design was made to make a single microcavity device core (SMD Core 1) to mold an optically clear 1.5 ml container with a single microcavity (FIGS. 15A and 15B). The design was to mold a frustum of a cone microcavity at the bottom of the container, the container having an effective angle α of 45°. The lip of the container was designed in such a way that it can be closed with a cap from a standard 1.5 ml microfuge tube. Using the CAD file, a steel core was made by precision machining to form the inverse of the desired feature in the core. The mold was designed such that the insert tool for molding the single microcavity was interchangeable with other insert tools to mold containers having various microcavities, e.g., size, shapes of microcavities, effective angle, etc.

A second CAD design was made to make SMD core 2 to mold a container such as that shown in FIGS. 6 and 7 and particularly, FIGS. 16A and 16B, with a frustum of a cone microcavity at the bottom of the container with an effective angle α of 60°. The features of the single microcavity in the molded containers SMD1 and SMD2 are shown in Table 1.

The 1.5 ml containers with a single microcavity, SMD1 or SMD2, were injection molded in a KraussMaffei injection molding machine (Model K65-CX; KraussMaffei technologies; Munich, Germany) with resins, COC-S-04 or PMMA. The resin pellets for each container were melted (COC-S-04 at 232 to 238° C., PMMA at 215 to 227° C.) and then injected at 16,000 psi. The mold temperature was held at 66° C. and the injection time was 0.78 sec for both resins. Each container was molded individually.

TABLE 1

Features of the microcavity in 1.5 ml molded container

| Container | Effective angle (degrees) | Configuration | Top Dimensions (μm) | Bottom dimensions (μm) | Depth (μm) | Volume (nL) |
|---|---|---|---|---|---|---|
| SMD1 | 45 | frustoconical | 500 (diameter) | 250 (diameter) | 500 | 57 |
| SMD2 | 60 | frustoconical | 500 (diameter) | 250 (diameter) | 500 | 57 |

2—Injection Molded 10 mL Containers with a Single Microcavity (SMD3-SMD4)

Figure 17A:
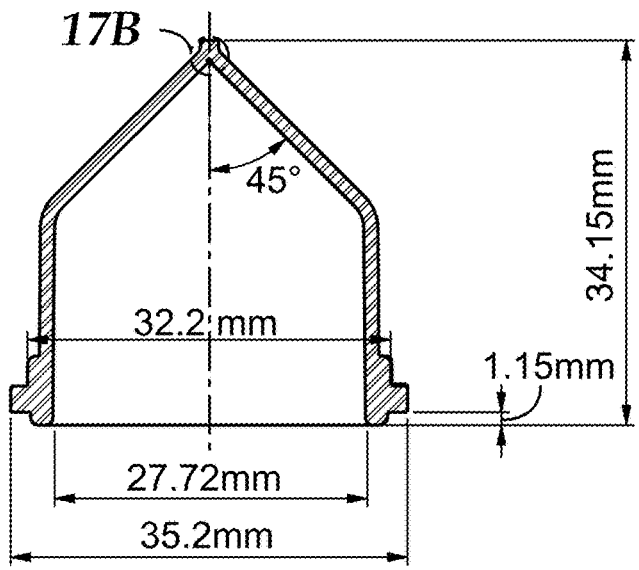
FIG. 17A a side cross-sectional view of SMD3, a sample detection container used in the Examples, SMD3 including a single microcavity and a wall having an effective angle α of 45 degrees.
Figure 17B:
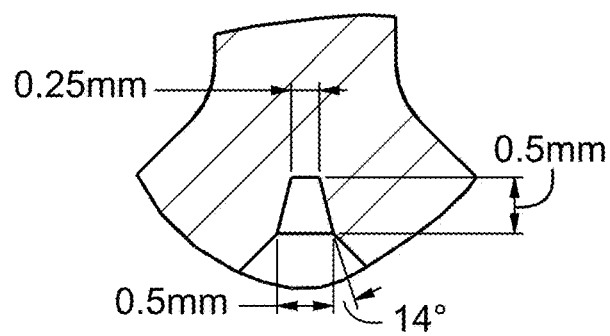
FIG. 17B is a close-up side cross-sectional view of the microcavity of SMD3 of FIG. 17A.
Figure 18A:
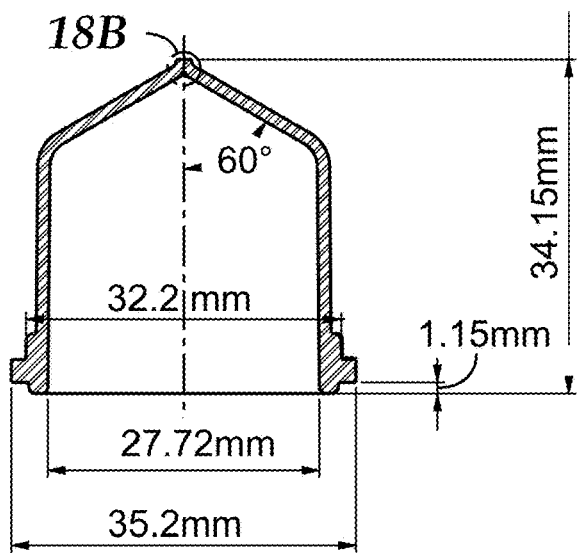
FIG. 18A is a side cross-sectional view of SMD4, a sample detection container used in the Examples, SMD4 including a single microcavity and a wall having an effective angle α of 60 degrees.
Figure 18B:
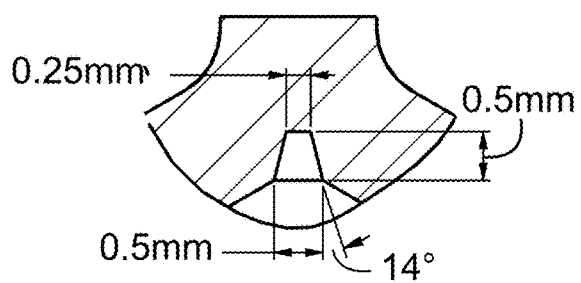
FIG. 18B is a close-up side cross-sectional view of the microcavity of SMD4 of FIG. 18A.

CAD designs were made to make SMD core 3 (FIGS. 17A and 17B) and SMD core 4 (FIGS. 18A and 18B) to mold a 10 mL container with a frustum of a cone microcavity at the bottom of the container with effective angle of 45 degrees and 60 degrees, respectively. The lip of the container was designed to have a twist and lock mechanism so that it can be closed with a cap (see, e.g., cap 104 of FIGS. 1-2 and 4) or coupled to a filter holder (see, e.g., the filter housing 332 of FIGS. 10-14), as described above with respect to FIGS. 1-2, 4 and 12-14. SMD core 4 (SMD4) was substantially the same as the sample detection container 102 of FIGS. 1-3, 4, 5 and 12-14. The features of the single microcavity in the molded containers SMD3 and SMD4 are shown in Table 2.

TABLE 2

Features of the microcavity in 10 mL molded container

| Container | Effective angle (degrees) | Configuration | Top Dimensions (μm) | Bottom dimensions (μm) | Depth (μm) | Volume (nl) |
|---|---|---|---|---|---|---|
| SMD3 | 45 | frustoconical | 500 (diameter) | 250 (diameter) | 500 | 57 |
| SMD4 | 60 | frustoconical | 500 (diameter) | 250 (diameter) | 500 | 57 |

The 10 mL containers with a single microcavity, SMD3 or SMD4, were injection molded in a KraussMaffei injection molding machine (Model K65-CX; KraussMaffei technologies; Munich, Germany) with resin, COC-S-04. The resin pellets for each cap/filter holder were melted at 232 to 238° C., and then injected at 16,000 psi. The mold temperature was held at 66° C. and the injection time was 0.78 sec. Each container was molded individually.

3—Injection Molded 20 ml and 100 ml Sample Detection Containers with Microcavity Surfaces (MS1-MS2)

Figure 19:
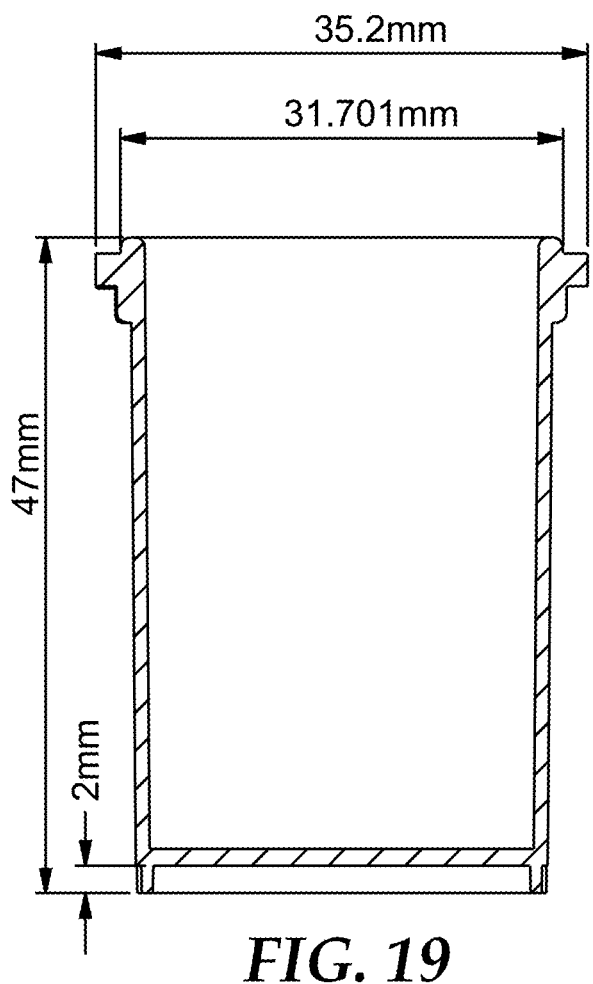
FIG. 19 is a side cross-sectional view of MS1, a sample detection container used in the Examples, MS1 including a microcavity surface comprising a plurality of microcavities.
Figure 20A:
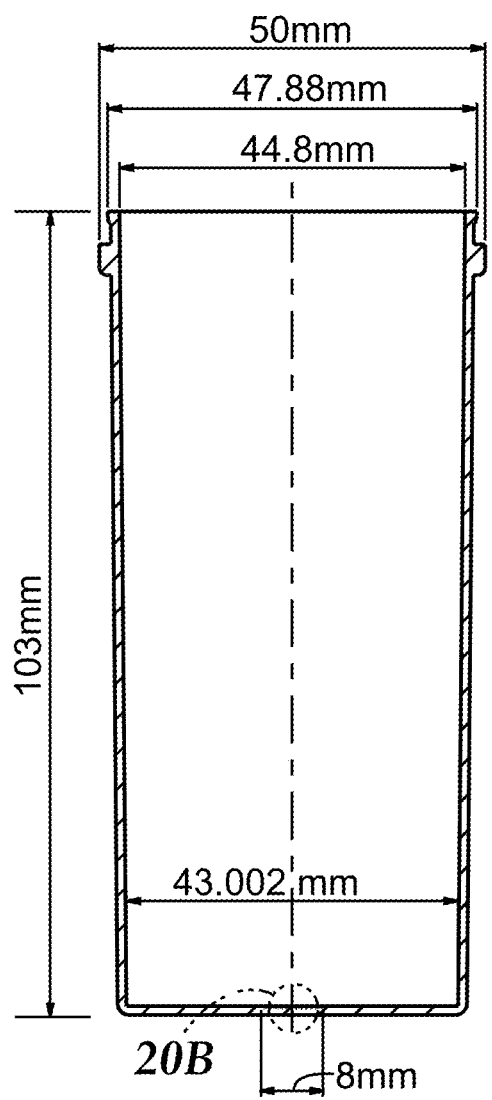
FIG. 20A is a side cross-sectional view of MS2, a sample detection container used in the Examples, MS2 including a microcavity surface comprising a plurality of microcavities.
Figure 20B:
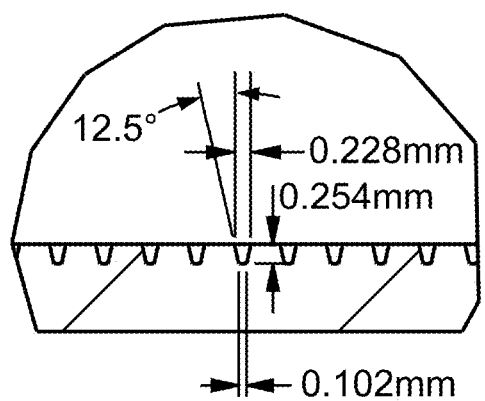
FIG. 20B is a close-up side cross-sectional view of the microcavity surface of MS2 of FIG. 20A.
Figure 21A:
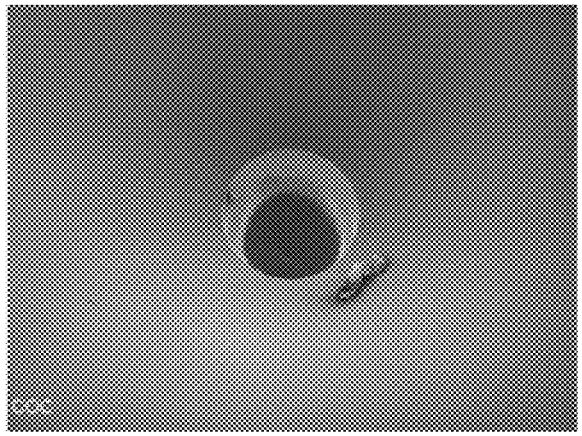
FIGS. 21A-21D are optical micrographs of the microcavity of SMD1 of FIGS. 15A and 15B.
Figure 21B:
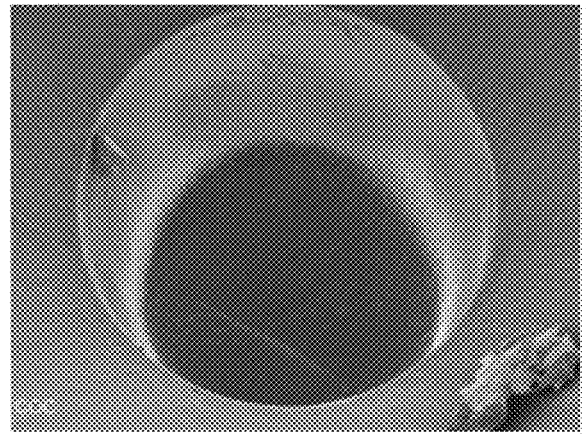
Figure 21C:
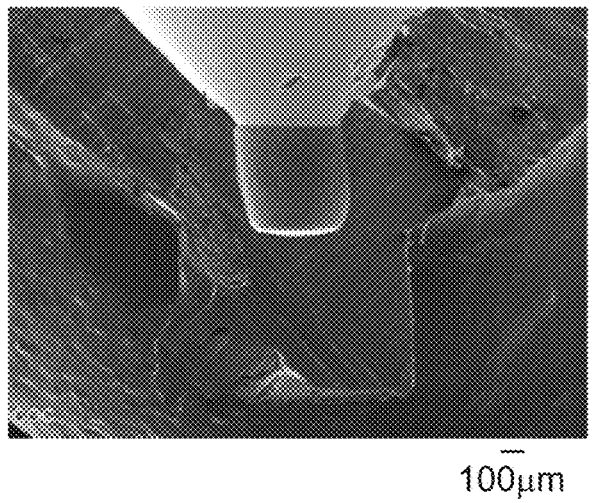
Figure 21D:
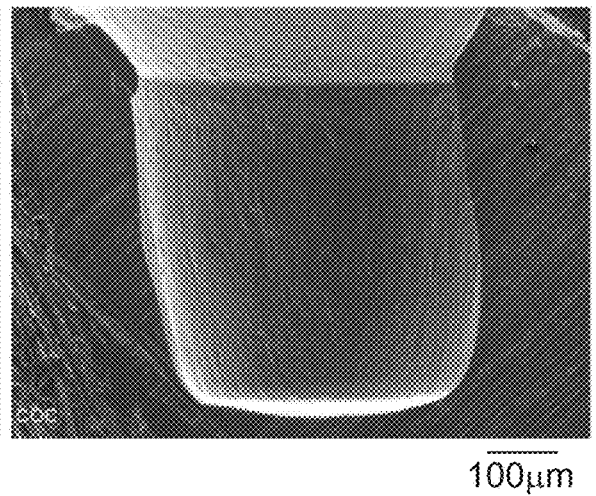
Figure 23A:
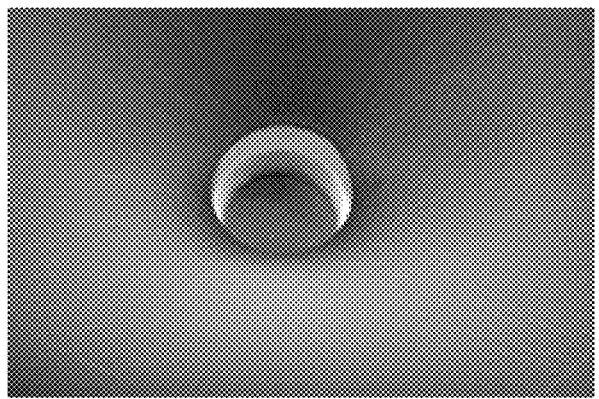
FIGS. 23A-23D are optical micrographs of the microcavity of SMD3 of FIGS. 17A and 17B.
Figure 23B:
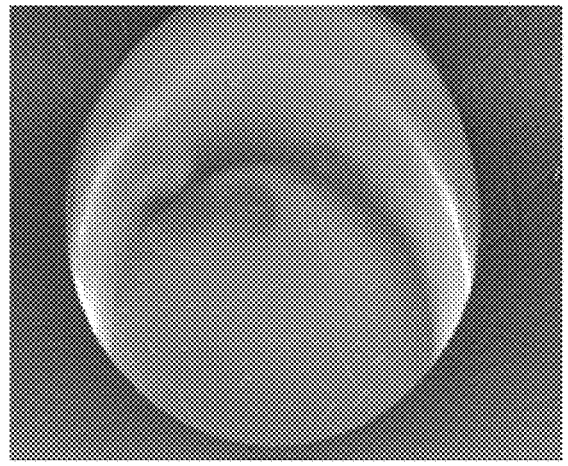
Figure 23C:
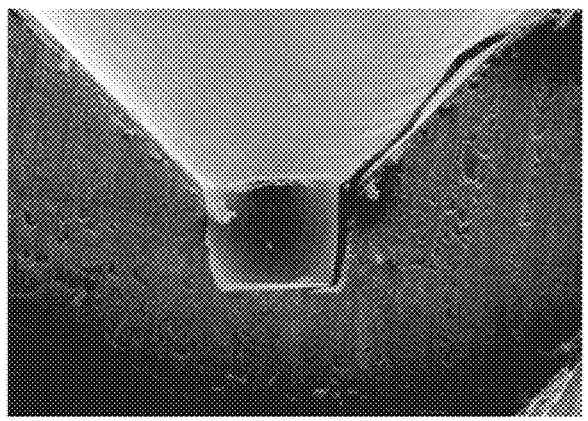
Figure 23D:
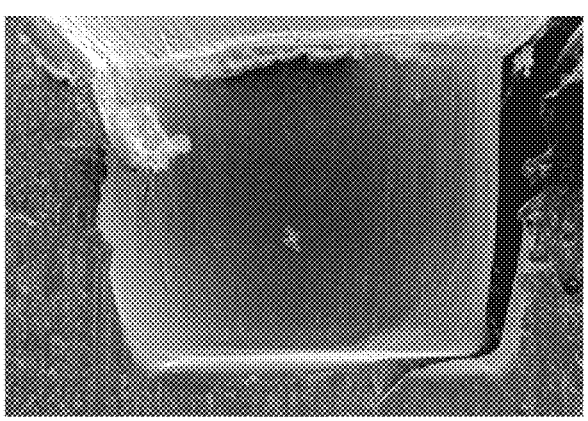
Figure 24A:
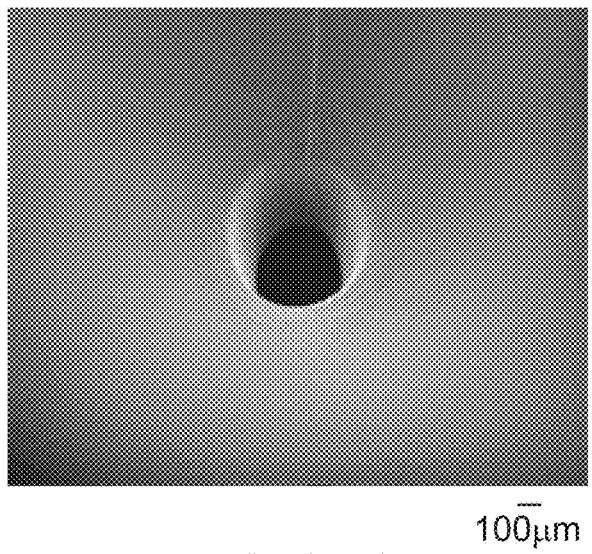
FIGS. 24A-24D are optical micrographs of the microcavity of SMD4 of FIGS. 18A and 18B.
Figure 24B:
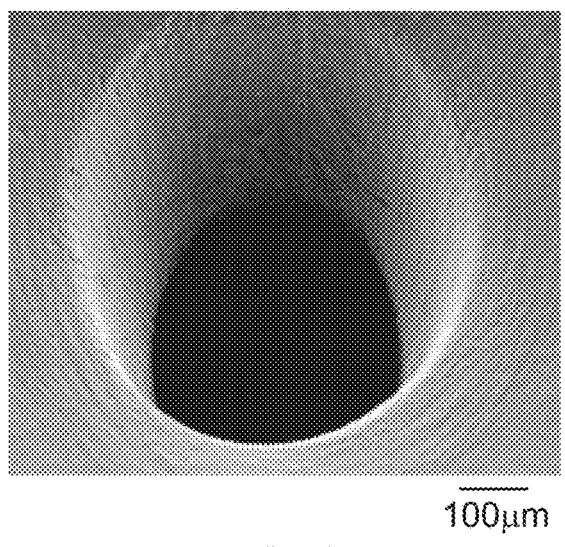
Figure 24C:
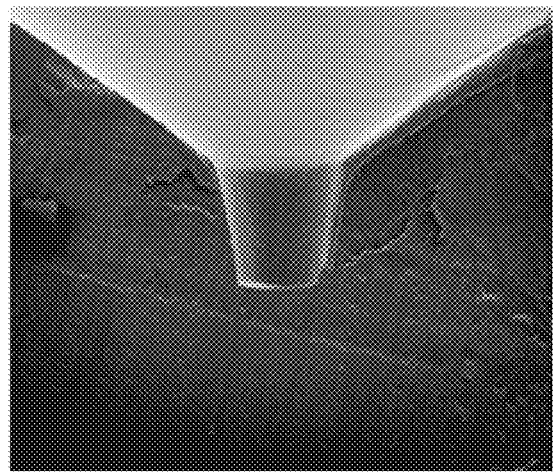
Figure 24D:
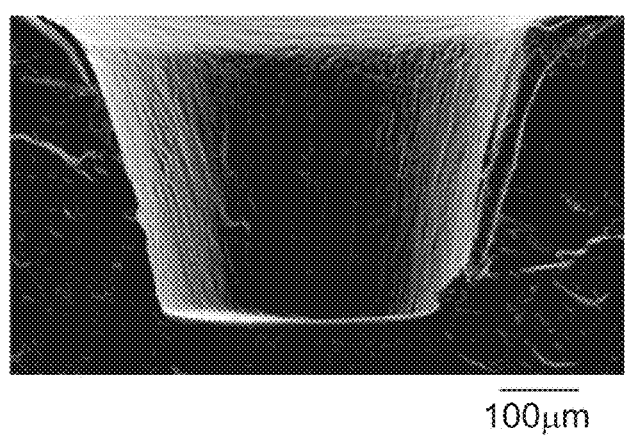
Figure 25A:
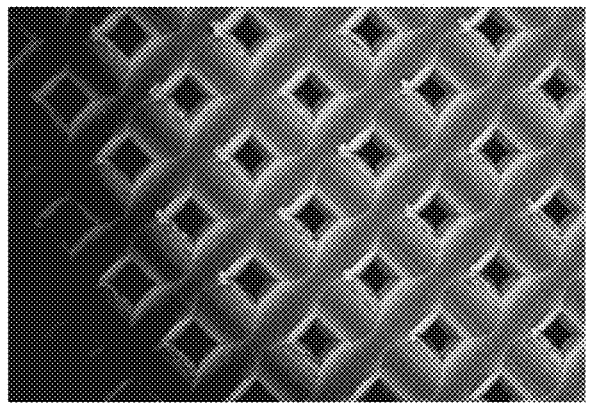
FIGS. 25A-25D are optical micrographs of the microcavity surface of MS1 of FIG. 19.
Figure 25B:
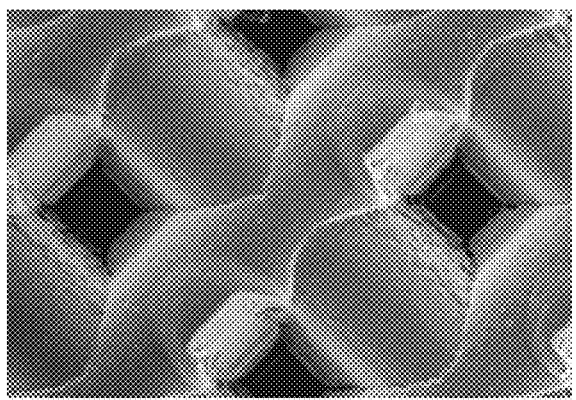
Figure 25C:
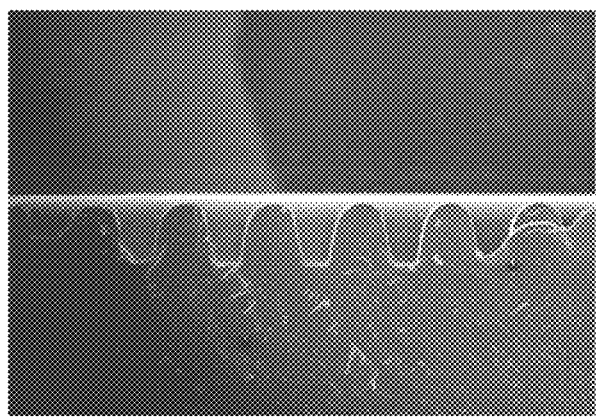
Figure 25D:
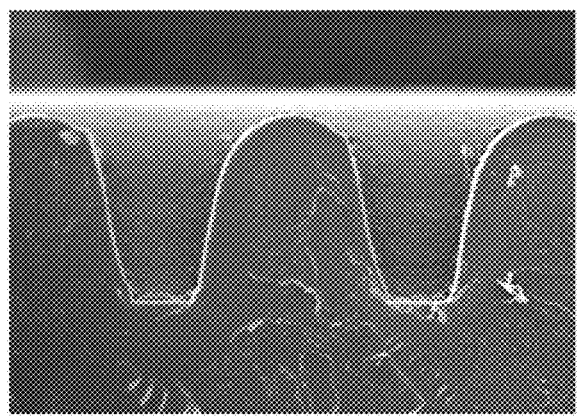
Figure 26A:
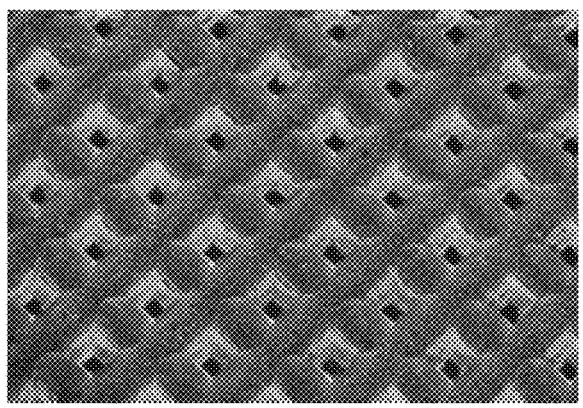
FIGS. 26A-26D are optical micrographs of the microcavity surface of MS2 of FIGS. 20A and 20B.
Figure 26B:
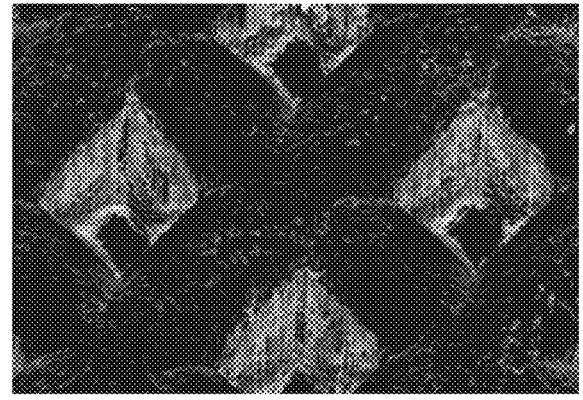
Figure 26C:
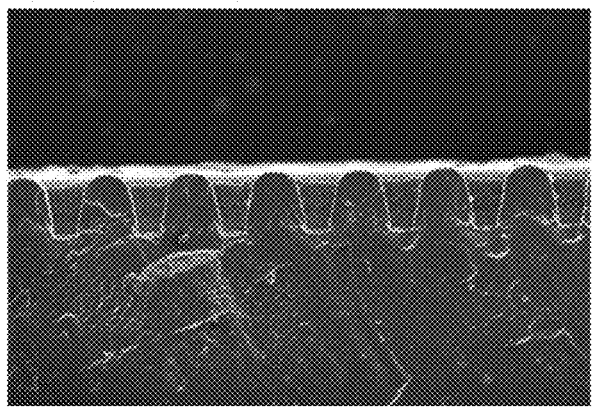
Figure 26D:
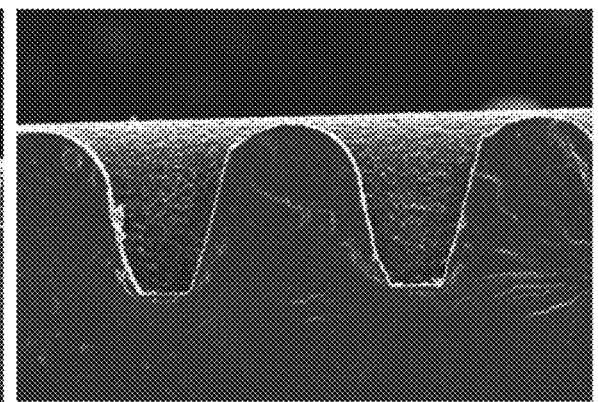

CAD designs were made to make MS1 core (FIG. 19) and MS2 core (FIGS. 20A and 20B) to mold a 20 ml container and a 100 ml container, respectively, each having a plurality of microcavities at the flat bottom of the container, each microcavity having the shape of a frustum of a pyramid. While a close-up view of the microcavity surface for MS1 is not shown in the figures, the same microcavity surface as shown for MS2 (see FIGS. 20A and 20B) was employed in MS1. The steel core was made by precision machining to form the inverse of the desired feature in the core. The lip of MS1 was designed to have a twist and lock mechanism so that it can be closed with a cap (see, e.g., cap 104 of FIGS. 1-2 and 4) or coupled to a filter holder (see, e.g., the filter housing 332 of FIGS. 10-14), as described above with respect to FIGS. 1-2, 4 and 12-14. The lip for MS2 was designed to be closed with a standard flip cap. The features of the microcavities in the molded containers MS1 and MS2 are shown in Table 3.

TABLE 3

Physical Dimensions of Microcavity Surfaces (MS)

| MS | Density/ sq cm | Shape | Pitch (μm) | Top (μm) | Bottom (μm) | Depth (μm) | Calculated draft Angle (degrees) | Volume (nL) | Aspect Ratio** |
|---|---|---|---|---|---|---|---|---|---|
| MS1 | 826 | Square | 348 | 228 | 100 | 254 | 14 | 7 | 1.11 |
| MS2 | 826 | Square | 348 | 228 | 100 | 254 | 14 | 7 | 1.11 |

**Aspect ratio (depth divided by top dimensions)

The 20 ml and 100 ml containers with a microcavity surface, MS1 or MS2, were injection molded in a Krauss-Maffei injection molding machine (Model K65-CX; Krauss-Maffei technologies; Munich, Germany) with resin, COC-S-04. The resin pellets for each container were melted at 232 to 238° C., and then injected at 16,000 psi. The mold temperature was held at 66° C. and the injection time was 0.78 sec. Each container was molded individually.

Scanning Electron Microscopy of Single Microcavity (from Molded Containers SMD1-SMD4) and Microcavity Surface (from Molded Containers MS1-MS2)

The molded containers were cut above the microcavity or microcavity surface and then mounted on an aluminum stub and sputter coated with gold/palladium. These were then examined using a JSM-7001F Scanning Electron Microscope (JEOL Ltd, Tokyo, Japan). After the initial examination, the samples were cross sectioned by submerging in liquid nitrogen and striking with a hammer. The cross sections were mounted on an additional stub, sputter coated, and examined as mentioned previously. Surface images were taken at a viewing angle of 70° off the surface of the stub; the cross section images were taken at viewing angle normal to the surface of the sectioned face. Images were captured at magnifications of 50× and 150×.

Optical images of SMD1 container are shown in FIGS. 21A, 21B, 21C, and 21D; SMD2 in 22A, 22B, 22C, and 22D; SMD3 in FIGS. 23A, 23B, 23C, and 23D; SMD4 in FIGS. 24A, 24B, 24C, and 24D; MS1 in FIGS. 25A, 25B, 25C, and 25D; and MS2 in FIGS. 26A, 26B, 26C, and 26D.

Preparation of Molded Filtration Devices

CAD designs were made to make a filter holder (such as the filter portion 308 comprising the filter holder 332 of FIGS. 10-14) to hold a 30 mm membrane filter (see, e.g., the filter 312 of FIGS. 10 and 12-14); a filter connection assembly (such as the filter connection assembly 320 of FIGS. 10, 11 and 14) comprising a connector (such as the connector 322 of FIGS. 10, 11 and 14) and a gasket (such as the gasket 324 of FIG. 10) to be coupled to the filter holder; and a gasket (such as the gasket 335 of FIGS. 10 and 12) to provide a seal between the membrane filter and the filter connection assembly. The gasket of the filter connection assembly (i.e., the gasket 324 of FIG. 10) can be used to couple the remainder of the filter connection assembly and the filter holder to a sample bottle (e.g., the receptacle portion 306 of FIGS. 10-11 and 14). The filter holder and the connector were made by injection molding using polypropylene, while the gaskets were made using medical grade SANTOPRENE® 181-55MED Thermoplastic Elastomer (ExxonMobil Chemical Company, Houston, Tex.). The connector has vent port (such as the vent port 328 of FIGS. 10-11) to fit a plug (such as the plug 330 of FIGS. 10-11) formed of sintered polypropylene to allow air movement during vacuum filtration. The connector locks into the filter holder (e.g., by the threaded connection described above with respect to FIGS. 10 and 11). The gasket of the filter connection assembly (i.e., the gasket 324 of FIG. 10) fits over a neck of the connector and is used to connect the sample bottle to the filter connection assembly (which in turn is connected to the filter holder/housing).

Preparation of Bacterial Cultures for Testing

Bacterial cultures used in the examples are shown in Table 4 and were obtained from American Type Culture Collection (ATCC); Manassas, Va.

TABLE 4

Bacteria strains used in examples

| Bacteria | ATCC ® No. |
|---|---|
| Escherichia coli | 51813 ™ |
| Citrobacter freundii | 14135 ™ |
| Enterobacter aerogenes | 29007 ™ |
| Klebsiella pneumoniae | 4352 ™ |

A culture for testing was prepared by inoculating a pure culture of a target bacteria strain from Table 4 into TSB (BD Tryptic Soy Broth; Becton, Dickinson and Co., Franklin Lakes, N.J.) and grown overnight at 37° C. The culture was diluted serially in Butterfield's phosphate buffer (Whatman Inc.; Piscataway, N.J.) to obtain the desired colony forming units (cfu) per milliliter desired for inoculating into water samples. The final two serial dilutions containing about $10^1$-$10^2$ cfu/mL were used to prepare a sample for testing or plating. E. coli and other coliform bacteria concentrations were quantified for the bacterial dilutions using 3M™ PETRIFILM™ E. coli/Coliform Count Plates (3M Co., St. Paul, Minn.). The plates were prepared and used according to manufacturer's instruction and incubated overnight at 37° C. The plates were read using a 3M™ PETRIFILM™ Plate Reader (3M Co.) to determine the cfu/mL.

Preparation of Sugar Dye Substrate Culture Media

A culture medium was prepared by mixing 5 grams (g) of tryptose (Difco laboratories, Detroit, Mich.), 5 g of sodium chloride, 1 g of sorbitol, 1 g of tryptophan, 2.7 g of di-potassium hydrogen phosphate, 2 g of potassium di-hydrogen phosphate, and 0.1 g laurylsulfate sodium salt (all obtained from Sigma Aldrich, St. Louis, Mo.) with 1000 mL of double distilled water. The culture media was autoclaved at 121° C. for 15 min.

Dye substrates shown in Table 5 were dissolved in DMSO (Dimethyl sulfoxide, DMSO, Sigma Aldrich, St. Louis, Mo.) to form a solution containing 100 milligrams sugar substrate per milliliter of DMSO. The substrate solution was added to the culture media to provide a final concentration of 40 micrograms of sugar substrate/milliliter of culture medium (µg/mL).

TABLE 5

Sugar-dye substrates

| Name | Abbreviation | Excitation Wavelength (nm) | Emission Wavelength (nm) |
|---|---|---|---|
| Sugar-dye substrates obtained from Marker Gene Technologies, Eugene OR | | | |
| 4-Methylumbelliferyl β-D-galactopyranoside | Mu-Gal | 350 | 450 |
| 4-Methylumbelliferyl β-D-glucuronide | Mu-GlcU | 350 | 450 |
| Fluorescein di-β-D-galactopyranoside | Flu-di-Gal | 485 | 520 |

TABLE 5-continued

Sugar-dye substrates

| Name | Abbreviation | Excitation Wavelength (nm) | Emission Wavelength (nm) |
|---|---|---|---|
| Resorufin β-D-galactopyranoside | Res-Gal | 530 | 590 |
| Sugar-dye substrates obtained from MP Biomedical, Solon OH | | | |
| Resorufin β-D-glucuronide | Res-GlcU | 530 | 590 |

Note:
Three samples were prepared and tested for the Reference Example and for each example. While the example is described in singular, three replicates were prepared and tested. Counts are reported as the average of the results. Onset of fluorescence records the first instance that fluorescence was observed in an image.

Reference Example

Selection of Sugar Dye Substrates for E. coli/Coliform Detection a) Detection of E. coli Using Galactosidase Substrates Culture media with sugar enzyme substrates were prepared according to the procedure above and dispensed into a black 96-well optical bottom microtiter plate (Nalgene Nunc International, Rochester, N.Y.). An E. coli culture was prepared as described above and serially diluted to obtain desired amount of cfu per mL. The media in the 96-well plates were inoculated with 10 µl of serially diluted cells to obtain wells containing approximately 1 cfu, 10 cfu or 100 cfu in each wells and a minimum of three wells were used for each of the inoculations. A control well was prepared with 10 microliters of Butterfield's buffer. The plates were incubated at 37° C. and read in a kinetic mode using a Tecan Infinite 200 PRO multimode reader (Tecan US, Inc. Durham, N.C.). The fluorescence intensity was recorded as a function of time. Time to detection was established as the time point where the signal was 50 times greater than the initial reading (background). Results are shown in Table 6. All the substrates tested showed fluorescence upon growth of E. coli and it took about 15 to 17 hr to detect 1 cfu of E. coli in 100 microliters.

TABLE 6

Detection of E. coli using galactosidase substrates

| | Time to detect E. coli (S/B ratio of 50:1) | | |
|---|---|---|---|
| Sugar Substrate | 1 cfu | 10 cfu | 100 cfu |
| Mu-gal | 17 hr | 12 hr | 8 hr |
| Flu-di-gal | 17 hr | 12 hr | 8 hr |
| Res-gal | 16 hr | 11 hr | 8 hr | b) Detection of E. coli Using Combination of Glucuronidase and Galactosidase Substrates Culture medium was prepared, tested, and the resulting data was analyzed according to the procedure for detection of E. coli, except that a combination of glucuronidase substrates (Mu-GlcU or Res-GlcU) and galactosidase substrates (Flu-di-Gal or Res-Gal) was used as the sugar dye substrate as shown in Table 6. The culture medium was dispensed into 96-well microtiter plates and the wells were inoculated with serially diluted culture to obtain approximately 1 cfu, 10 cfu or 100 cfu. A minimum of three wells were used for each of the inoculations. The data in Table 7 show that when a combination of two different substrates are used in a single well, the enzyme activities of the glucuronidase and galactosidase can each be detected by fluorescence at different times (hr). The reaction is detected sooner for higher bacteria concentrations.

TABLE 7

Detection of E. coli using glucuronidase and galactosidase substrates

| | Time to detect E. coli (S/B ratio of 50:1) | | | | | |
|---|---|---|---|---|---|---|
| | Glucuronidase | | | Galactosidase | | |
| Sugar Dye Substrate | 1 cfu | 10 cfu | 100 cfu | 1 cfu | 10 cfu | 100 cfu |
| Mu-Glcu + Res-gal | 17 hr | 10 hr | 8.5 hr | 16 hr | 9 hr | 7.5 hr |
| Mu-Glcu + Flu-di-gal | 17 hr | 11 hr | 8.5 hr | 16 hr | 12 hr | 11 hr |
| Res-Glcu + Flu-di-gal | 17 hr | 9 hr | 8 hr | 16 hr | 12 hr | 11 hr |
| Res-Glcu + Mu-gal | 17 hr | 9 hr | 8 hr | 16 hr | 11 hr | 8 hr | c) Detection of Coliforms Using Flu-di-gal

The procedure for the detection of E. coli outlined in example a) was repeated using the bacteria listed in Table 7. The culture medium prepared with Flu-di-gal was dispensed into 96-well microtiter plates and inoculated with serially diluted cultures to obtain approximately 1 cfu, 10 cfu or 100 cfu in each of the wells. A minimum of three wells were used for each of the inoculations. The data in Table 8 indicates that Flu-di-gal is a suitable substrate for galactosidase for detecting of coliforms.

TABLE 8

Detection of coliforms using Flu-di-gal

| | Time to detect coliforms (S/B ratio of 50:1) | | |
|---|---|---|---|
| Bacteria | 1 cfu | 10 cfu | 100 cfu |
| E. coli | 13 hr | 12 hr | 10 hr |
| E. aerogenes | 15 hr | 13 hr | 10 hr |

TABLE 8-continued

Detection of coliforms using Flu-di-gal

| | Time to detect coliforms (S/B ratio of 50:1) | | |
|---|---|---|---|
| Bacteria | 1 cfu | 10 cfu | 100 cfu |
| C. freundii | 13 hr | 12 hr | 8 hr |
| K. pneumoniae | 17 hr | 13 hr | 10 hr |

Example 1—Use of Fluorocarbon-Based Liquids as a Separation Liquid to Separate Liquid Contained in Microcavities from Bulk Liquid (i.e., Above the Microcavities)

The fluorocarbon-based liquids/fluids such as 3M™ Fluorinert™ Electronic Liquids and 3M™ Novec™ Engineered fluids (Table 9; 3M Company) are hydrophobic, heavier than water and when mixed with water, they phase-separate and move to the bottom. These compounds were tested to see if they could be used as a separation liquid of the present disclosure to separate the liquid in closed capillaries and microcavities from bulk liquid (e.g., the supernatant above the capillaries and microcavities after centrifugation) and maintain the separation to enable rapid detection. Interfacial tension between the Fluorinert™ Electronic Liquids and distilled water was measured by the Wilhelmy plate technique using Kruss K100 instrument (Kruss, Matthews, N.C.) following manufacturer's instructions (Table 9). For the liquids where measurement was not possible, interfacial tension was calculated by subtracting the separation liquid surface tension from that of water, 72 dynes/cm (0.072 N/m) (Table 9). The measured and calculated value for FC-40 and FC-43 were in close agreement (Table 9).

TABLE 9

Properties of separation liquids used adapted from 3M technical documents

| | 3M ™ Novec ™ Engineered Fluid | | 3M ™ Fluorinert ™ Electronic Liquids | | | | | |
|---|---|---|---|---|---|---|---|---|
| Properties | HFE-7200 | HFE-7100 | FC-72 | FC-84 | FC-77 | FC-40 | FC-43 | FC-70 |
| Avg Mol Wt | 264 | 250 | 338 | 388 | 415 | 650 | 670 | 820 |
| Density g/mL | 1.43 | 1.52 | 1.68 | 1.73 | 1.78 | 1.85 | 1.86 | 1.94 |
| Typical boiling point ° C. | 76 | 61 | 56 | 80 | 97 | 165 | 175 | 215 |
| Surface tension dynes/cm (N/m) | 13.6 (0.0136) | 13.6 (0.0136) | 10 (0.01) | 12 (0.012) | 15 (0.015) | 16 (0.016) | 16 (0.016) | 18 (0.018) |
| Measured interfacial tension[a] (water and separation liquid), dynes/cm (N/m) | ND | ND | ND | ND | ND | 56.389 (0.056389) | 56.013 (0.056013) | ND |
| Calculated interfacial tension[b] (water and separation liquid), dynes/cm (N/m) | 58.4 (0.0584) | 58.4 (0.0584) | 62 (0.062) | 60 (0.060) | 57 (0.057) | 56 (0.056) | 56 (0.056) | 54 (0.054) |
| Refractive index | N/A | N/A | 1.251 | 1.261 | 1.28 | 1.29 | 1.291 | 1.303 |
| Solubility of separation liquid in water ppm (wt.) | <20 | 12 | <5 | <5 | <5 | <5 | <5 | <5 |

TABLE 9-continued

Properties of separation liquids used adapted from 3M technical documents

| Properties | 3M ™ Novec ™ Engineered Fluid | | 3M ™ Fluorinert ™ Electronic Liquids | | | | | |
|---|---|---|---|---|---|---|---|---|
| | HFE-7200 | HFE-7100 | FC-72 | FC-84 | FC-77 | FC-40 | FC-43 | FC-70 |
| Solubility of water in separation liquid ppm (wt.) | 92 | 95 | <10 | 11 | 13 | <7 | 7 | 8 |

[a]Measured using a Wilhelmy plate with Kruss K100 instrument
[b]Calculated by subtracting fluorocarbon-based liquid surface tension from that of water (72 dynes/cm (0.072 N/m))
ND: Not determined
N/A: Not available a) Separation of Liquid in VoluPac Tube:

A solution of blue food color (McCormik & Company Inc., Hunt Valley, Md.) was diluted 1:100 in 100 mL of distilled water. One mL of the solution was dispensed into VoluPac (Sartorius Corporation, Bohemia, N.Y.) tubes and the tubes were then placed in a Hettich Mikro 22 microcentrifuge (Andreas Hettich GmbH & Co. KG, Tuttlingen, Germany) with a swing-out rotor (1154) and centrifuged for 10 min at 13000 RPM (18,890×g). After centrifugation, the tubes were removed and about 250 ul of separation liquid (Table 9) was added to each tube using a pipette tip. All of the separation liquids listed in Table 9 moved down to the bottom of the tube, but stayed above the capillary. This effectively separated the liquid in the capillary from the bulk liquid.

b) Single Microcavity Containers:

A solution of fluorescein sodium salt (Sigma Aldrich) was prepared by dissolving 10 mg of fluorescein in 100 mL of distilled water. One ml of the solution was dispensed into SMD1 and SMD2 containers and the containers were closed tightly using caps cut from 1.5 ml microfuge containers (Plastibrand microtubes, Brand GmbH & Co. KG, Wertheim, Germany) to form the cap shape as generally shown in FIGS. 6-7. Seven ml of the solution was dispensed into SMD3 and SMD4 containers. A circular disk (1 mm thick), 30 mm in diameter, was die cut using a hole punch from a polypropylelene sheet and was placed on the filter holder (i.e., to seal up the openings in the filter holder—see the apertures 337 of FIG. 12) and used to close the open first ends of containers SMD3 and SMD4. That is, the filter holder was modified to form a simple cap for the sample detection containers SMD3 and SMD4 (e.g., similar to the cap 104 of FIGS. 1, 2 and 4. The opening in the base of the filter holder was closed with a polyethylene cap (U.S. Plastic Corp, Lima, Ohio—see the cap 317 in FIG. 12). SMD1 and SMD2 containers were then placed in a Hettich Mikro 22 microcentrifuge (Andreas Hettich GmbH & Co. KG, Tuttlingen, Germany) with a swing-out rotor (1154) and centrifuged for 10 min at 13000 RPM (18,890×g). SMD3 and SMD4 containers were placed in a swinging bucket centrifuge rotor and centrifuged in the Multipurpose Centrifuge, Model 5810R, for 15 minutes at 4000 RPM (3220×g). After centrifugation, the containers were removed and about 250 ul of the separation liquids listed in Table 9 were added to SMD1 and SMD2 containers and 2 ml to SMD3 and SMD4 containers. All of the separation liquids listed in Table 9 moved down to the bottom of the container. The microcavity was imaged with imager system 2 (inverted fluorescence microscope). The images obtained showed presence of fluorescence in the microcavity and separation of bulk liquid from the liquid inside the microcavity (i.e., by the separation liquid).

c) Microcavity Surface Containers:

A solution of fluorescein sodium salt (Sigma Aldrich) was prepared by dissolving 10 mg of fluorescein in 100 mL of distilled water. Ten and 25 mL of the solution was dispensed into MS1 and MS2 containers, respectively. The filter holder was modified as described in Example 1b to form a cap for the sample detection container MS1. The opening in the base of the filter holder was closed with a polyethylene cap (U.S. Plastic Corp—see the cap 317 in FIG. 12). The MS2 container (100 ml) was closed with a polypropylene cap cut from 3M™ Flip-Top Dilution Bottle (3M Co.). A silicone gasket was used with the cap to provide a tight seal. The containers were placed in a swinging bucket centrifuge rotor and centrifuged in the Multipurpose Centrifuge, Model 5804, for 15 minutes at 5000 RPM (4400×g). After centrifugation, 4 ml for MS1 container and 8 ml for MS2 container of separation liquids, FC-43, FC-77 or HFE-7200 were added. The separation liquids moved down the liquid to the bottom of the container and covered the microcavity surface. The microcavities were imaged with imager system 2 (inverted fluorescence microscope). The images obtained showed presence of fluorescence in the microcavities and separation of bulk liquid from the liquid inside the microcavities.

Example 2—Concentration of Bacteria in the Microcavity of SMD1 (Effective Angle=45 Degrees) and SMD2 (Effective Angle=60 Degrees) by Centrifugation with and Without Use of Separation Liquids Bacterial suspensions of E. coli and E. aerogenes were each prepared in 1 mL of Butterfield's buffer (3M Co.) to provide approximately $10^2$ cfu/mL of buffer, and transferred into SMD1 and SMD2 containers. Twelve containers of each bacterial suspension were prepared and closed tightly with a cap cut from 1.5 ml microfuge tubes (Plastibrand microtubes). The containers were then placed in a Hettich Mikro 22 microcentrifuge (Andreas Hettich GmbH & Co. KG, Tuttlingen, Germany) with a swing-out rotor (1154) and centrifuged for 10 min at 13000 RPM (18,890×g). In addition, separate containers were also spun in an Eppendorf 5417R centrifuge (Eppendorf) with a fixed angle rotor (Rotor F-45-30-11) for 10 min at 13,375 RPM (19,000×g).

After centrifugation, one set of three containers were removed; the supernatant was removed using 1 mL pipette (PR-1000, Rainin Instruments, LLC, Oakland, Calif.) and plated on 3M™ PETRIFILM™ E. coli/Coliform Count Plates for E. coli and E. aerogenes, according to the manufacturer's instructions. To another set of three containers for each of the separation liquid, 250 μl of separation liquids, FC-43 or FC-77 or HFE-7200, were added, and the separation liquids separated the bulk liquid (i.e., supernatant) from the liquid (i.e., concentrate) in the microcavity. The liquid separated from the microcavity by the separation liquids (i.e., bulk supernatant) was removed using 1 mL pipette (PR-1000, Rainin Instruments, LLC) and plated on 3M™ PETRIFILM™ E. coli/Coliform Count Plates for E. coli and E. aerogenes. The plates were incubated overnight at 37° C. and read using 3M™ PETRIFILM™ Plate Reader to determine colony forming units (cfu). The percent recovery, i.e., the percentage of bacteria captured in the microcavity, was calculated by subtracting the cfu in the bulk supernatant from the cfu that were in the initial 1 ml sample, dividing by input cfu and multiplying by 100. The average percent recovery in the microcavity is shown in Table 10 and 11. The recovery of bacteria in the microcavity was similar in the containers with and without use of separation liquids to separate the bulk liquid.

through a 0.45 μm mixed cellulose ester filter (HAWP02500) using 25 mm microanalysis filter holder (Millipore, Billerica, Mass.). The filter holder was fitted with a 25 mm 0.45 μm mixed cellulose ester filter and assembled with a 15 ml funnel. The base of the filter holder was connected to a vacuum flask attached to a vacuum assembly; the supernatant from the containers after centrifugation was added to the funnel and filtered through the filter at a vacuum pressure of about 508 mm of mercury. To another set of three containers for each of the separation liquids, 2 ml of separation liquids FC-43 or FC-77 or HFE-7200 were added and the separation liquids separated the bulk liquid (i.e., bulk supernatant above microcavity) from the liquid (i.e., concentrate) in the microcavity. The supernatant in each container was removed using a Falcon® 10 mL serological disposable sterile pipet (Cat #357551, Corning Life Sciences, Tewksbury, Mass.) from the separation liquid and

TABLE 10

Percent recovery of E. coli in SMD1 (45 degrees) and SMD2 (60 degrees)

| | % Recovery in microcavity | | | | | | | |
|---|---|---|---|---|---|---|---|---|
| | Swing-Out Rotor | | | | Fixed Angle Rotor | | | |
| Input: 100 cfu Container | No separation liquid | FC-43 | FC-77 | HFE-7200 | No separation liquid | FC-43 | FC-77 | HFE-7200 |
| SMD1 | 90 | 90 | 91 | 88 | 87 | 85 | 88 | 84 |
| SMD2 | 91 | 89 | 90 | 85 | 88 | 84 | 82 | 80 |

TABLE 11

Percent recovery of E. aerogenes in SMD1 (45 degrees) and SMD2 (60 degrees)

| | % Recovery in microcavity | | | | | | | |
|---|---|---|---|---|---|---|---|---|
| | Swing-Out Rotor | | | | Fixed Angle Rotor | | | |
| Input: 100 cfu Container | No separation liquid | FC-43 | FC-77 | HFE-7200 | No separation liquid | FC-43 | FC-77 | HFE-7200 |
| SMD1 | 84 | 85 | 83 | 82 | 84 | 85 | 84 | 82 |
| SMD2 | 82 | 82 | 80 | 80 | 80 | 80 | 82 | 80 |

Example 3—Concentration of Bacteria in the Microcavity of SMD3 (Effective Angle=45 Degrees) and SMD4 (Effective Angle=60 Degrees) by Centrifugation with and Without Use of Separation Liquids Bacterial suspensions of E. coli and E. aerogenes were each prepared in 1 mL of Butterfield's buffer (3M Co.) to provide approximately $10^2$ cfu/mL of buffer, and transferred into SMD3 and SMD4 containers containing 6 ml of Butterfield's buffer. Twelve containers of each bacterial suspension were prepared. The filter holder was modified as described above in Example 1b to form a cap for the containers. The containers were placed in a swinging bucket centrifuge rotor and centrifuged in the Multipurpose Centrifuge, Model 5810R, for 15 minutes at 4000 RPM (3220× g).

After centrifuging, one set of three containers was removed and the supernatant in each container was filtered through a 0.45 μm mixed cellulose ester filter (HAWP02500, Millipore) as described above.

3M™ PETRIFILM™ E. coli/Coliform Count Plates were hydrated according to the manufacturer's instructions. The filters were carefully removed from the filter holder with sterile forceps and placed on the hydrated plate, and the plates were incubated overnight at 37° C. The plates were read on a 3M™ PETRIFILM™ Plate Reader and/or manually to determine colony forming units (cfu). The percent recovery in the microcavity, i.e., the percentage of bacteria captured in the microcavity, was calculated by subtracting the cfu on the filter from the cfu that were in the initial sample prior to centrifuging, dividing by input cfu and multiplying by 100. The average percent recovery in microcavity is shown in Table 12. The recovery of bacteria in the microcavity was similar in the containers with and without use of separation liquids to separate the bulk liquid.

TABLE 12

Percent recovery of E. coli and E. aerogenes in SMD3 (45 degrees) and SMD4 (60 degrees)

| | % Recovery in microcavity | | | | | | | |
|---|---|---|---|---|---|---|---|---|
| | E. Coli | | | | E. aerogenes | | | |
| Input: 100 cfu Container | No separation liquid | FC-43 | FC-77 | HFE-7200 | No separation liquid | FC-43 | FC-77 | HFE-7200 |
| SMD3 | 84 | 85 | 84 | 82 | 85 | 84 | 82 | 80 |
| SMD4 | 85 | 84 | 84 | 82 | 80 | 80 | 82 | 80 |

Example 4—Scanning Electron Microscopy of Bacteria Concentrated in the Microcavity of SMD3 (45 Degrees) and SMD4 (60 Degrees) by Centrifugation Bacterial suspensions of E. coli was prepared in 10 mL of sterile water to provide approximately $10^6$ cfu/mL, and transferred into SMD3 and SMD4 containers. The filter holder was modified as described above in Example 1b to form a cap for the containers. The containers were placed in a swinging bucket centrifuge rotor and centrifuged in the Multipurpose Centrifuge for 10 minutes at 4000 RPM (3220×g). After centrifuging, the containers were removed and the supernatant was removed. Any liquid left behind in the container was removed using a sterile cotton swab and the samples were processed immediately.

The molded containers were cut above the microcavity and then mounted on an aluminum stub and sputter coated with gold/palladium. These were then examined using the JSM-7001F Scanning Electron Microscope (JEOL Ltd). Surface images were taken at a viewing angle of 70° off the surface of the stub. Images were captured at magnifications of 3000×.

Figure 27A:
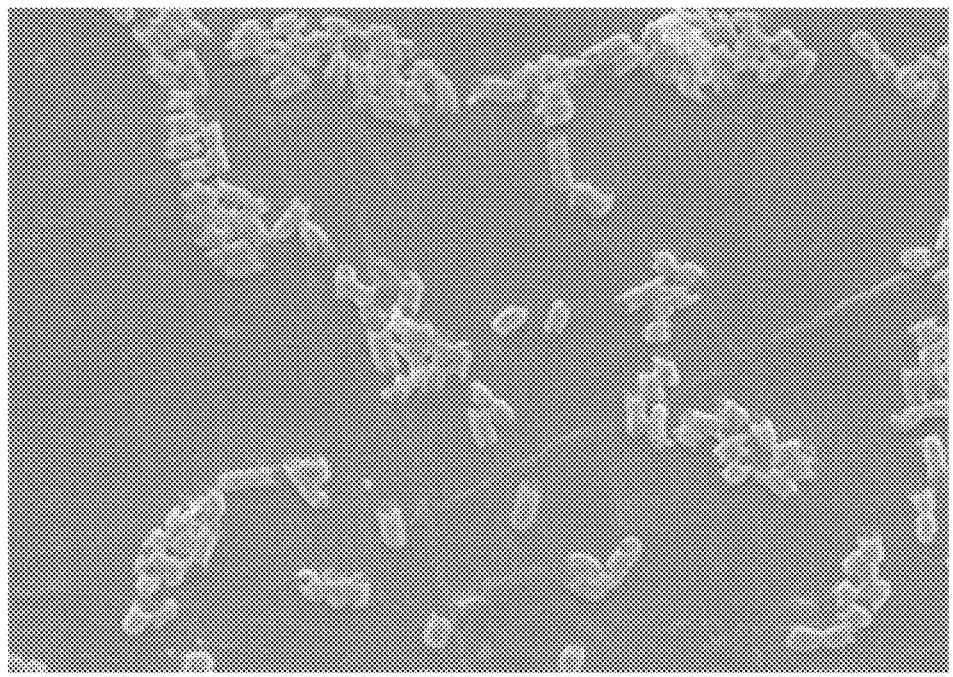
FIGS. 27A-27B are optical micrographs of bacteria inside the microcavity of the SMD3 and SMD4 containers of the Examples, respectively.
Figure 27B:
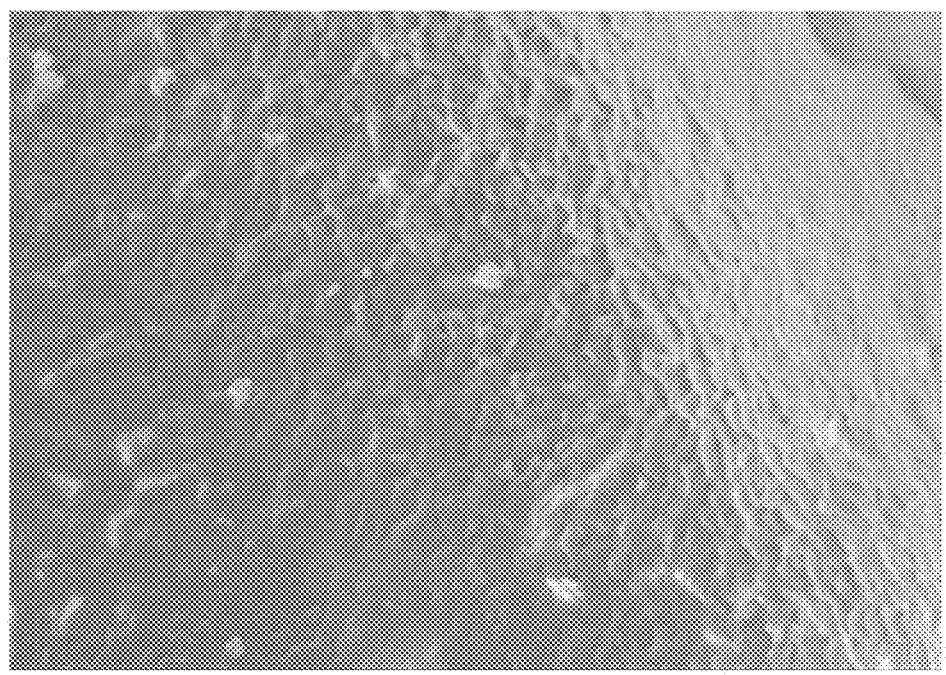

Optical images of bacteria inside the microcavity of each of the SMD3 and SMD4 containers are shown in FIGS. 27A and 27B, respectively.

Example 5—Concentration of Bacteria in the Microcavities of MS1 and MS2 Containers by Centrifugation with and without Use of Separation Liquids Bacterial suspensions of E. coli and E. aerogenes were each prepared in 10 and 100 mL of Butterfield's buffer (3M Co.) to provide approximately total of $10^2$ cfu, and transferred into MS1 and MS2 containers. Twelve containers of each bacterial suspension were prepared for each of MS1 and MS2 containers. The filter holder was modified as described above in Example 1b to form a cap for the MS1 containers. The MS2 containers (100 ml) was closed with a polypropylene cap cut from 3M™ Flip-Top Dilution Bottle (3M Co.). The containers were placed in a swinging bucket centrifuge rotor and centrifuged in the Multipurpose Centrifuge, Model 5804, for 15 minutes at 5000 RPM (4400×g). After centrifuging, one set of three containers were removed and the supernatant in each container was filtered through a 0.45 µm mixed cellulose ester filter (HAWP02500, Millipore) as described in Example 3. To another set of three containers for each of the separation liquids, 4 ml for MS1 container and 8 ml for MS2 container of separation liquids FC-43, FC-77 or HFE-7200 were added, and the separation liquids separated the bulk liquid (i.e., the supernatant) from the liquid (i.e., the concentrate) in the microcavities. The supernatant in each container was removed using a Falcon® 10 mL serological disposable sterile pipet (Cat #357551, Corning Life Sciences) from the separation liquids and filtered through a 0.45 µm mixed cellulose ester filter (HAWP02500, Millipore), as described in Example 3.

3M™ PETRIFILM™ E. coli/Coliform Count Plates were hydrated according to the manufacturer's instructions. The filters were carefully removed from the filter holder with sterile forceps and placed on the hydrated plate, and the plates were incubated overnight at 37° C. The plates were read on a 3M™ PETRIFILM™ Plate Reader and/or manually to determine colony forming units (cfu). The percent recovery in the microcavities, i.e., the percentage of bacteria captured in the microcavities, was calculated by subtracting the cfu on the filter from the cfu that were in the initial sample prior to centrifuging, dividing by input cfu and multiplying by 100. The average percent recovery in microcavities is shown in Table 13 and the recovery of bacteria in microcavities was similar in the containers with and without use of separation liquids to separate the bulk liquid.

TABLE 13

Percent recovery of E. coli and E. aerogenes in MS1 and MS2 microcavities

| | % Recovery in microcavity | | | | | | | |
|---|---|---|---|---|---|---|---|---|
| | E. Coli | | | | E. aerogenes | | | |
| Input: 100 cfu Container | No separation liquid | FC-43 | FC-77 | HFE-7200 | No separation liquid | FC-43 | FC-77 | HFE-7200 |
| MS1 | 88 | 85 | 86 | 82 | 86 | 82 | 84 | 82 |
| MS2 | 86 | 84 | 83 | 80 | 82 | 84 | 82 | 80 |

Example 6—Detection of Bacteria in SMD1 (45 Degrees) and SMD2 (60 Degrees) Containers with and without Separation Liquids An *E. coli* suspension containing $10^1$-$10^2$ cfu was prepared in 1 mL of COLILERT™ media and dispensed into SMD1 and SMD2 containers, and the containers were closed tightly using caps cut from 1.5 ml microfuge tubes (Plastibrand microtubes). Control samples were prepared similarly, but received 10 µL of Butterfield's buffer. The containers were then placed either in a Hettich Mikro 22 microcentrifuge (Andreas Hettich GmbH & Co. KG) with a swing-out rotor (1154) or a Eppendorf 5417R centrifuge (Eppendorf) with a fixed angle rotor (Rotor F-45-30-11). The containers were centrifuged for 10 min at 13000 RPM (19,000×g). After centrifugation, one set of three containers were removed, inverted slowly to drain the media back into the container, away from the microcavity, and the containers were incubated at 37° C. in the inverted position. To the other set of three containers for each of the separation liquid, 250 µl of separation liquids, FC-43, FC-77 or HFE-7200 were added, and the containers were incubated at 37° C. in the upright position. The separation liquids moved to the bottom of the container as they are heavier (i.e., denser) than the aqueous sample medium (water), and separated the liquid in the microcavity (i.e., the concentrate) from the bulk liquid (i.e., the supernatant). This essentially served the same purpose as, and served as an effective alternative to, inverting the container to separate the bulk liquid from the microcavity.

The microcavity of the inverted containers was imaged using imager system 1 (stereo microscope), and the microcavity of the containers with separation liquid was imaged with imager system 2 (inverted fluorescence microscope) every hour.

The same initial *E. coli* suspension was tested in COLI-LERT™ media in a 96-well microtiter plate as described in the Reference Example.

SMD1 container (effective angle=45 degrees) unlike SMD2 container (effective angle=60 degrees) contained excess liquid above the top opening of the microcavity upon inversion of the container, such that the retained volume was greater than the volume of the microcavity. The top surface of the liquid in SMD2 was observed to be at the same level as the top opening of the microcavity, such that the retained volume was substantially equal to the volume of the microcavity. To measure the amount of excess liquid above the top opening, the containers were drained and liquid around the rim was wiped and the amount of excess liquid was measured using a 10 ul pipette (Cat. No. PR-10, Rainin Instrument LLC). On the average, the retained volume was about 2.3 ul for the SMD1 container (as compared to 57 nL volume of the microcavity, Table 14). No liquid above the microcavity could be pipetted with the SMD2 container. The use of separation liquids avoided the issue of excess liquid above the top opening of the microcavity, as the separation liquids moved to the bottom of the container and covered over the top opening of the microcavity irrespective of the effective angle of the container.

As shown in Table 15, the onset of fluorescence was observed at approximately 3 hours in the inverted SMD2 container and at 5 hrs in the inverted SMD1 container and at 15 hrs in the microtiter plate. However, onset of fluorescence was observed at approximately 3 hours in both containers, SMD1 and SMD2, containing separation liquids, FC-43, FC-77 or HFE-7200. No increased fluorescence over background was seen in control samples at 3 hrs or later times (up to 24 hrs of incubation). The use of either fixed angle or swing-out rotor had no effect on onset of fluorescence in the SMD1 or SMD2 container with or without separation liquids.

TABLE 14

Ratio of total retained volume to volume of microcavity in containers with and without separation liquids and time to detection

| Container | Volume of microcavity (nL) | Retained excess liquid µl/std. dev* | Ratio of total liquid to volume of the microcavity | Time to detect 10 cfu of *E. coli* |
|---|---|---|---|---|
| SMD1 (no separation liquid) | 57 | 2.3/0.3 | 41.4 | 5 hr |
| SMD2 (no separation liquid) | 57 | 0 | 1 | 3 hr |
| SMD1 (with separation liquid) | 57 | 0[a] | 1 | 3 hr |
| SMD2 (with separation liquid) | 57 | 0[a] | 1 | 3 hr |

*0 indicates liquid could not be measured
[a] No water phase could be seen above the top opening of the microcavity as it was covered by the separation liquid and the retained excess liquid was assumed to be zero.

TABLE 15

Comparison of time to detect 10 cfu of *E. coli* in SMD1 (45 degrees) and SMD2 (60 degrees) with and without separation liquids

| | Mu-glcU fluorescence* | | | | | | | | |
|---|---|---|---|---|---|---|---|---|---|
| | Inverted | | | | Inverted | Upright | | | |
| | SMD1 | | Upright | | SMD2 | SMD2 | | | |
| Time | (no separation liquid) | SMD1 with HFE-7200 | SMD1 with FC-77 | SMD1 with FC-43 | (no separation liquid) | with HFE-7200 | SMD2 with FC-77 | SMD2 with FC-43 | 96-well microtiter plate (100 microliters) |
| 1 hr | No | No | No | No | No | No | No | No | No |
| 2 hr | No | No | No | No | No | No | No | No | No |
| 3 hr | No | Yes | Yes | Yes | Yes | Yes | Yes | Yes | No |

TABLE 15-continued

Comparison of time to detect 10 cfu of E. coli in SMD1 (45 degrees) and SMD2 (60 degrees) with and without separation liquids

| | Mu-glcU fluorescence* | | | | | | | | |
|---|---|---|---|---|---|---|---|---|---|
| | Inverted | | | | Inverted | Upright | | | |
| | SMD1 | | Upright | | SMD2 | | | | |
| Time | SMD1 (no separation liquid) | SMD1 with HFE-7200 | SMD1 with FC-77 | SMD1 with FC-43 | SMD2 (no separation liquid) | SMD2 with HFE-7200 | SMD2 with FC-77 | SMD2 with FC-43 | 96-well microtiter plate (100 microliters) |
| 4 hr | No | Yes | Yes | Yes | Yes | Yes | Yes | Yes | No |
| 5 hr | Yes | Yes | Yes | Yes | Yes | Yes | Yes | Yes | No |
| 7 hr | Yes | Yes | Yes | Yes | Yes | Yes | Yes | Yes | No |
| 8 hr | Yes | Yes | Yes | Yes | Yes | Yes | Yes | Yes | No |
| 15 h | Yes | Yes | Yes | Yes | Yes | Yes | Yes | Yes | Yes |

*"Yes" refers to fluorescence observed; "No" refers to no fluorescence observed.

Example 7—Detection of Bacteria in SMD 3 (45 Degrees) and SMD4 (60 Degrees) Containers with and without Separation Liquids An E. coli suspension containing 10 cfu was prepared in 1 mL of COLILERT™ media and dispensed into SMD3 and SMD4 containers containing 6 ml of COLILERT™ media. The filter holder was modified as described above in Example 1b to form a cap for the SMD3 and SMD4 containers. The containers were placed in a swinging bucket centrifuge rotor and centrifuged in the Multipurpose Centrifuge 5810R for 15 minutes at 4000 RPM (3220×g). After centrifugation, one set of three containers were removed, inverted slowly to drain the media back into the container, away from the microcavity, and the containers were incubated at 37° C. in the inverted position. To the other set of three containers for each of the separation liquids, 2 ml of separation liquids, FC-43, FC-77 or HFE-7200 were added, and the containers were incubated at 37° C. in the upright position. The separation liquids moved to the bottom of the container, as they are heavier (denser) than the aqueous sample medium (water), and separated the liquid in the microcavity (i.e., the concentrate) from the bulk liquid (i.e., the supernatant). This essentially served the same purpose as, and served as an effective alternative to, inverting the container to separate the bulk liquid from the microcavity.

The microcavity of inverted containers was imaged using imager system 1 (stereo microscope), and the microcavity of the containers with separation liquids was imaged with imager system 2 (inverted fluorescence microscope) every hour. The containers with separation liquids were also occasionally observed in the inverted position using imager system 1 as depicted in 150E of FIG. 4. The same initial E. coli suspension was tested in COLILERT™ media in a 96-well microtiter plate as described in the Reference Example. SMD3 container (effective angle=45 degrees) unlike SMD4 container (effective angle=60 degrees) showed excess liquid above the top opening of the microcavity upon inversion of the container. This behavior was similar irrespective of the volume used (1 or 10 ml). To measure the amount of excess liquid above the top opening of the microcavity, the containers were drained and liquid around the rim was wiped and the amount of excess liquid was measured using a 10 ul pipette (Cat. No. PR-10, Rainin Instrument LLC), and on the average, it was about 4.4 ul for SMD3 container (as compared to the 57 nL volume of the microcavity, Table 16). No liquid could be pipetted with the SMD4 container. The use of separation liquids avoided the issue of excess liquid above the top opening of the microcavity, as the separation liquids moved to the bottom of the container and covered over the top opening of the microcavity irrespective of the effective angle of the container.

As shown in Table 17, the onset of fluorescence was observed at approximately 3 hours in the inverted SMD4 container, at 7 hrs in the inverted SMD3 container, and at 15 hrs in the microtiter plate. However, onset of fluorescence was observed at approximately 3 hours in both containers, SMD3 and SMD4, containing separation liquids, FC-43, FC-77 or HFE-7200. Fluorescence in the microcavity could also be observed in the containers with a separation liquid upon inversion of the container. No increased fluorescence over background was seen in control samples at 3 hrs or later (up to 24 hrs of incubation).

TABLE 16

Ratio of total retained volume to volume of microcavity in containers with and without separation liquids and time to detection

| Container | Volume of microcavity (nL) | Retained excess liquid μl/std. dev* | Ratio of total liquid to volume of the microcavity | Time to detect 10 cfu of E. coli |
|---|---|---|---|---|
| SMD3 (no separation liquid) | 57 | 4.4/0.2 | 78.2 | 7 hr |
| SMD4 (no separation liquid) | 57 | 0 | 1 | 3 hr |
| SMD3 (with separation liquid) | 57 | 0[a] | 1 | 3 hr |
| SMD4 (with separation liquid) | 57 | 0[a] | 1 | 3 hr |

*0 indicates liquid could not be measured

[a]No water phase could be seen above the top opening of the microcavity as it was covered by the separation liquid and the retained excess liquid was assumed to be zero.

TABLE 17

Comparison of time to detect 10 cfu of E. coli in SMD3 (45 degrees) and SMD4 (60 degrees) containers with and without separation liquids

| | Mu-glcU fluorescence* | | | | | | | | |
|---|---|---|---|---|---|---|---|---|---|
| | Inverted | | | | Inverted | Upright | | | |
| | SMD3 | | Upright | | SMD4 | SMD4 | | | |
| Time | (no separation liquid) | SMD3 with HFE-7200 | SMD3 with FC-77 | SMD3 with FC-43 | (no separation liquid) | with HFE-7200 | SMD4 with FC-77 | SMD4 with FC-43 | 96-well microtiter plate (100 microliters) |
| 1 hr | No | No | No | No | No | No | No | No | No |
| 2 hr | No | No | No | No | No | No | No | No | No |
| 3 hr | No | Yes | Yes | Yes | Yes | Yes | Yes | Yes | No |
| 4 hr | No | Yes | Yes | Yes | Yes | Yes | Yes | Yes | No |
| 5 hr | No | Yes | Yes | Yes | Yes | Yes | Yes | Yes | No |
| 7 hr | Yes | Yes | Yes | Yes | Yes | Yes | Yes | Yes | No |
| 8 hr | Yes | Yes | Yes | Yes | Yes | Yes | Yes | Yes | No |
| 15 h | Yes | Yes | Yes | Yes | Yes | Yes | Yes | Yes | Yes |

*"Yes" refers to fluorescence observed; "No" refers to no fluorescence observed.

Example 8—Detection of Bacteria in Containers with a Microcavity Surface with and Without Separation Liquids An *E. coli* suspension containing 10 cfu was prepared in COLILERT™ media and dispensed into MS1 (10 ml) and MS2 (100 ml) containers. The filter holder was modified as described above in Example 1b to form a cap for the MS1 containers. The MS2 container (100 ml) was closed with a polypropylene cap cut from 3M™ Flip-Top Dilution Bottle (3M Co.). A silicone gasket was used with the cap to provide a tight seal. The containers were centrifuged in the Multipurpose Centrifuge 5804 for 15 minutes at 5000 RPM (4400×g). After centrifugation, one set of three containers were removed, inverted slowly to drain the media back into the container, away from the microcavity, and the containers were incubated at 37° C. in the inverted position. To the other set of three containers for each of the separation liquids, 4 ml for MS1 container and 8 ml for MS2 container of separation liquids FC-43, FC-77 or HFE-7200 were added, and the containers were incubated at 37° C. in the upright position. The separation liquids moved to the bottom of the container as they are heavier (i.e., denser) than the aqueous sample medium (water), and separated the liquid in the microcavity (i.e., the concentrate) from the bulk liquid (i.e., the supernatant). This essentially served the same purpose as, and served as an effective alternative to, inverting the container to separate the bulk liquid from the microcavity.

The microcavities of the inverted containers were imaged using imager system 1 (stereo microscope) and the microcavities of the containers with separation liquids were imaged with imager system 2 (inverted fluorescence microscope) every hour. The containers with separation liquids were also occasionally observed in the inverted position using imager system 1.

The same initial *E. coli* suspension was tested in COLILERT™ media in a 96-well microtiter plate as described in the Reference Example.

As shown in Table 18, the onset of fluorescence was observed at approximately 5 hours in both the inverted containers and containers with separation liquids FC-43, FC-77 or HFE-7200. Fluorescence in the microcavities could also be observed in the containers with separation liquids upon inversion of the containers. No increased fluorescence over background was seen in control samples at 5 hrs or later times (up to 24 hrs of incubation).

TABLE 18

Comparison of time to detect 10 cfu of E. coli

| | Mu-glcU fluorescence* | | | | | | | | |
|---|---|---|---|---|---|---|---|---|---|
| | | Upright | | | | Upright | | | |
| Time | Inverted MS1 (No separation liquid) | MS1 with HFE-7200 | MS1 with FC-77 | MS1 with FC-43 | Inverted MS2 (No separation liquid) | MS2 with HFE-7200 | MS2 with FC-77 | MS2 with FC-43 | 96-well microtiter plate (100 microliters) |
| 1 hr | No | No | No | No | No | No | No | No | No |
| 2 hr | No | No | No | No | No | No | No | No | No |
| 3 hr | No | No | No | No | No | No | No | No | No |
| 4 hr | No | No | No | No | No | No | No | No | No |
| 5 hr | Yes | Yes | Yes | Yes | Yes | Yes | Yes | Yes | No |
| 7 hr | Yes | Yes | Yes | Yes | Yes | Yes | Yes | Yes | No |
| 8 hr | Yes | Yes | Yes | Yes | Yes | Yes | Yes | Yes | No |
| 15 h | Yes | Yes | Yes | Yes | Yes | Yes | Yes | Yes | Yes |

*"Yes" refers to fluorescence observed; "No" refers to no fluorescence observed.

Example 9—Liquid Behavior in Sample Detection Containers of Various Angles with and Without Use of Separation Liquids Small containers (1.5 ml) with angles of 30, 40, 45, 50, 55, 60, 65, 70, 75 and 80 (FIGS. 28A-28J) degrees were made by rapid prototyping. The containers were made from CAD drawings using a UV curable epoxy composition (Accura® 60 plastic) in a sterolithography machine (Viper SI2 SLA® System) according to the manufacturer's instructions. The epoxy composition and the machine were manufactured by 3D Systems Corporation, Rock Hill S.C. As the microcavity could not be made by rapid prototyping, the area where microcavity is supposed to be was designed to be a cone shaped to a sharp point. As the angle gets larger, the cone gets flatter and still comes to a point, but the point is not as sharp.

a) Visualization Using Color:

A solution of blue food color (McCormik & Company Inc.) was diluted 1:100 in 100 mL of distilled water. One mL of the solution was dispensed into various angle containers and the containers were closed tightly using caps cut from 1.5 ml microfuge tubes (Plastibrand microtubes). One set of three containers for each effective angle, were slowly inverted and placed in an upside down position on a table. The presence of liquid at the tip of the containers (no separation liquids) was observed visually and using the imager 1 (stereo microscope) under a white light. The presence of excess liquid was noticed in containers with an effective angle of 30, 40, and 45 degrees and not in containers with effective angles of 50, 55, 60, 65, 70, 75 and 80 degrees.

To another set of three containers for each effective angle, with 1 mL of food color solution, 250 µl of separation liquids FC-43, FC-77 or HFE-7200 were added. The containers with separation liquids were observed visually and using the imager 2 (inverted microscope) under a white light. The separation liquids moved to the bottom of the container (greater density), irrespective of the effective angle of the container, and separated the bulk liquid from the tip of the container.

b) Visualization Using Fluorescence:

A solution of fluorescein sodium salt (Sigma Aldrich) was prepared by dissolving 10 mg of fluorescein in 100 mL of distilled water. One ml of the solution was dispensed into various angle containers (three containers for each effective angle) and the containers were closed tightly using caps cut from 1.5 ml microfuge tubes (Plastibrand microtubes). The containers were slowly inverted and placed in an upside down position on a table. The presence of liquid at the tip of the containers (no separation liquids) was observed visually and using the fluorescent imager 1 (stereo microscope). The presence of excess liquid was again noticed in containers with an effective angle of 30, 40, and 45 degrees and not in containers with effective angles of 50, 55, 60, 65, 70, 75 and 80 degrees.

To another set of three containers for each effective angle, with 1 mL of fluorescein solution, 250 ml of separation liquids FC-43, FC-77 or HFE-7200 were added. The presence of liquid at the tip of the containers with separation liquids was observed visually and using the imager 2 (inverted microscope). The separation liquids moved to the bottom of the container (greater density) irrespective of the effective angle of the container, and separated the bulk liquid from the tip of the container.

c) Measurement of Excess Liquid

1) One ml of the distilled water was dispensed into various angle containers and the containers were slowly inverted to empty the water. The containers were then placed upside down on a Kimtech Science Kimwipes™ (Kimberly-Clark Professional, Roswell, Ga.) to remove any liquid on the rim of the containers. The containers were held in the inverted position and the amount of excess liquid present at the tip of the container was measured using a 20 µl (PR-20) or 10 µl (PR-10) or 2 µl (PR-2) pipette (Rainin Instruments LLC). The measurements were done for 5 different containers for each effective angle, and each measurement was repeated at least five times. The average results are reported in Table 19. The liquid could not be measured in containers with effective angles of 50 degrees and above and is represented as zero in Table 19.

To another set of three containers for each effective angle, with 1 mL of distilled water, 250 µl of separation liquids FC-43, FC-77 or HFE-7200 were added. The presence of liquid at the tip of the containers with separation liquids was observed visually to look for separation of water phase above the tip and the retained excess liquid was assumed to be zero if separation could be observed (Table 19).

2) The measured angle of the container wall above the 5 µl capillary of comparative VoluPac tubes (Sartorius Corporation, Bohemia, N.Y.) is about 40 degrees. The angle was measured using a protractor. One mL of the distilled water was dispensed into five VoluPac tubes, and the tubes were slowly inverted to empty the water. The tubes were then placed upside down on a Kimtech Science Kimwipes™ (Kimberly-Clark Professional) to remove any liquid on the rim of the tubes. The tubes were held in the inverted position and the amount of excess liquid present at the tip of the tube was measured as described above. The average amount of excess liquid present above the capillary tip in the VoluPac tubes was 12 µl (Table 19).

The excess liquid was also measured similarly with containers SMD1, SMD2, SMD3 and SMD4, and the results are shown in Table 19. To another set of three containers with 1 mL of distilled water, 250 ml of separation liquids FC-43, FC-77 or HFE-7200 were added. The presence of liquid at the tip of the containers with separation liquids was observed visually to look for separation of water phase above the tip and the retained excess liquid was assumed to be zero if separation could be observed (Table 19).

The ratio of total retained liquid volume (excess liquid plus the volume of the capillary/microcavity) to the volume of capillary/microcavity was also calculated (Table 20).

TABLE 19

Amount of excess liquid at the tip of the container with various effective angles

| Effective Angle | Excess liquid at the tip after inverting the container (µL)/std. dev* | Excess liquid at the tip after adding separation liquid (no inversion) |
| --- | --- | --- |
| 30 | 15/0.9 | 0[a] |
| 40 | 9/0.8 | 0[a] |
| 45 | 5/0.5 | 0[a] |
| 50 | 0 | 0[a] |
| 55 | 0 | 0[a] |
| 60 | 0 | 0[a] |
| 65 | 0 | 0[a] |
| 70 | 0 | 0[a] |
| 75 | 0 | 0[a] |
| 80 | 0 | 0[a] |
| 40 (VoluPac) | 12/1.1 | 0[a] |
| 45 (SMD1) | 2.3/0.3 | 0[a] |

TABLE 19-continued

Amount of excess liquid at the tip of the container with various effective angles

| Effective Angle | Excess liquid at the tip after inverting the container (µL)/std. dev* | Excess liquid at the tip after adding separation liquid (no inversion) |
|---|---|---|
| 45 (SMD3) | 4.4/0.2 | 0[a] |
| 60 (SMD2) | 0 | 0[a] |
| 60 (SMD4) | 0 | 0[a] |

*0 indicates liquid could not be measured
[a]No water phase could be seen above the tip of the container as it was covered by the separation liquid and the retained excess liquid was assumed to be zero.

TABLE 20

Ratio of total retained volume to volume of capillary/microcavity

| Container | Volume of capillary/microcavity (nL) | Excess liquid µL/std. dev | Ratio of total retained volume to volume of the capillary/microcavity |
|---|---|---|---|
| VoluPac | 5000 | 12/1.1 | 3.4 |
| SMD1 | 57 | 2.3/0.3 | 41.4 |
| SMD3 | 57 | 4.4/0.2 | 78.2 |
| SMD2 | 57 | 0* | 1 |
| SMD4 | 57 | 0* | 1 |
| Volupac (with separation liquid) | 5000 | 0[a] | 1 |
| SMD1 (with separation liquid) | 57 | 0[a] | 1 |
| SMD2 (with separation liquid) | 57 | 0[a] | 1 |
| SMD3 (with separation liquid) | 57 | 0[a] | 1 |
| SMD4 (with separation liquid) | 57 | 0[a] | 1 |

*0 indicates liquid could not be measured
[a]No water phase could be seen above the tip of the container as it was covered by the separation liquid and the retained excess liquid was assumed to be zero.

Example 10—Contact Angle Measurements of Molded Discs

Molded discs of PMMA (WF100 poly(methyl methacrylate), Mitsubishi Rayon Co Ltd, Tokyo, Japan), COC-X-10 (transparent cyclic olefin copolymer, TOPAS™8007X10, Topas Advanced Polymers Gmbh, Florence Ky.), COC-S-04 (transparent cyclic olefin copolymer, high moisture barrier; TOPAS™8007S-04, Topas Advanced Polymers Gmbh), PC (Lexan polycarbonate; HPS1R; SABIC Americas Corp., Houston Tex.), COP (transparent cyclo olefin polymer; Zeonor™ 1430R, Zeon Chemicals L.P., Louisville Ky.) were made as described in preparatory example "Preparation of Microstructures, 3—Injection Molded Lids" of PCT Patent Publication No. WO2013/003308. The static and dynamic contact angles of flat side of molded polymers were determined using the sessile drop method on a VCA 2500 XE Video Contact Angle System. The data was analyzed using VCA-2500XE image analysis software. The instrument and software were obtained from AST Products, Inc., Billerica Mass.

For the static contact angle, 1-µl droplets of water were delivered to the surfaces at room temperature. The right and left contact angles were measured immediately after the drop formed on the surface with the syringe tip retracted.

For the dynamic contact angle, 1-µl droplets were delivered to the surfaces and water was added or withdrawn from the droplet with the syringe set at medium speed. Frames of video images were obtained showing when the drop expanded or contracted most symmetrically to determine the Advancing and Receding dynamic contact angles. The hysteresis was calculated as the difference between the advancing and receding contact angles. Results are shown in Table 21.

TABLE 21

Static and Dynamic Contact Angle Measurements

| | Static contact Angle/ Std Dev | | Dynamic Contact Angle/ Std Dev. | | |
|---|---|---|---|---|---|
| Polymer | Left Angle | Right Angle | Advancing | Receding | Hysteresis |
| PMMA | 86.9/5.4 | 86.7/5.6 | 84.8/1.0 | 44.6/1.4 | 40.2 |
| PC | 89.9/1.4 | 89.8/1.7 | 93.6/2.0 | 37.8/1.6 | 55.8 |
| COC-X-10 | 96.4/2.1 | 96.1/1.7 | 91.2/2.2 | 41.1/3.5 | 50.1 |
| COC-S-04 | 95.7/1.5 | 95.5/1.4 | 97.7/1.5 | 41.5/0.8 | 56.2 |
| COP | 85.4/5.0 | 85.2/4.9 | 95.1/1.1 | 25.4/1.2 | 69.7 |

Example 11—Contact Angle Measurement of Molded Containers

The static contact angles of molded containers, SMD3 and SMD4 were determined using the sessile drop method as explained in Example 10. The molded containers were cut and a flat surface close to the cone angle was tested. In addition, a surface on the outside of the container was also tested. Four samples were tested and average results are reported in Table 22.

TABLE 22

Static Contact Angle Measurements

| Container | Static contact Angle/Std Dev | |
|---|---|---|
| | Left Angle | Right Angle |
| SMD3 (cone surface) | 76.9/9.0 | 75.7/5.7 |
| SMD4 (cone surface) | 83.6/5.9 | 83.3/5.5 |
| SMD3 (outside surface) | 79.4/3.6 | 79.8/3.2 |
| SMD4 (outside surface) | 79.8/2.1 | 81.4/1.8 |

Example 12—Roughness Measurements

The molded containers, SMD3 and SMD4 were cut above the microcavity and the surface topography of each sample was measured in three locations—(1) near the microcavity, (2) center of the cone-shaped surface (i.e., between the microcavity and the rim), and (3) and near the rim of the cone. Measurements were performed with the Wyko NT9800 interferometer (Bruker Corporation, Tucson, Ariz.), using the 10× objective and 1.0× field lens. Adjacent frames were stitched together to digitally increase the field-of-view and to yield a larger, continuous measurement region. The instrument was used in VSI mode with full resolution, 1x scan speed, single-scan mode, and modulation threshold set at 2%. The data was processed to remove tilt and cylindrical curvature and the roughness calculation was performed for each area of interest. The Vision® analysis software was used to calculate the roughness parameters, Ra and Rq. The calculated roughness values are listed in Table 23 for the two samples. The roughness values for SMD4 are lower than those for SMD3. The material makeup for SMD4 and SMD3 was the same, so the roughness variation was likely due to a molding artifact.

TABLE 23

Roughness values for the isolated regions of the sample images

| | Roughness average, Ra (nm) | | | Root mean square roughness, Rq (nm) | | |
|---|---|---|---|---|---|---|
| Container | Near microcavity | Center of the cone | Near rim of the cone | Near microcavity | Center of the cone | Near rim of the cone |
| SMD3 | 765.6 | 821.7 | 1515.0 | 2370 | 2645 | 4100 |
| SMD4 | 257.5 | 194.6 | 233.2 | 762 | 513 | 499 |

Ra: Arithmetic mean of the absolute values of the height of the surface profile
Rq: A function that takes the square of the measures. The RMS roughness of a surface is similar to the roughness average, with the only difference being the mean squared absolute values of surface roughness profile.

Example 13—Preparation of Filtration Apparatus

A filter portion (see the filter portion 308 of FIGS. 10 and 11) comprising a filter holder (see filter holder 332 of FIGS. 10-14) and a filter connection assembly (see the filter connection assembly 320 of FIGS. 10, 11 and 14) configured to be coupled together by a plurality (i.e., four, equally circumferentially-spaced) of cooperating twist lock threads and protrusions (as shown in FIGS. 10 and 12). A filter was positioned in the filter holder, and a gasket provided a seal between the filter and the connector of the filter connection assembly. The connector had a vent port with a filter plug. The filter plug was formed of POREX® hydrophobic polyethylene sheet POR-4902 (Porex Technologies, Fairburn, Ga.) and was cut to fit the vent port. A gasket (see gasket 324 of FIG. 10) was dimensioned to receive the top neck portion of the connector (see, e.g., the first end 321 of the connector 320 of FIG. 10), i.e., by being slid over the top portion in a friction fit, to form the filter connection assembly configured to be coupled to a neck of a sample bottle (i.e., the gasket was configured to be received in the opening of the sample bottle (or receptacle portion—see, e.g., the receptacle portion 306 of FIGS. 10, 11 and 14). The sample bottle (or receptacle portion) for this example was a 1 liter polypropylene sample bottle (Nalgene 2087 Narrow-Mouth Economy Bottle—Cat. No. 2087-0032; Nalgene Nunc, Thermo Fisher Scientific; Rochester N.Y.). The combination of the sample bottle (receptacle portion) and the filter portion formed a "first container" of a sample detection system according to the present disclosure (see first container 303 of FIGS. 10, 11 and 14).

A 30 mm non-woven support (Uniblend 135, wet laid polyester/cellulose blend filter media, Midwest Filtration, LLC, Cincinnati, Ohio) was die cut using a hole punch from a sheet of the material and inserted into the filter holder, followed by a filter (Filter A, Filter B, or Filter C). The filter connection assembly was connected between the filter portion and the sample bottle, and the other end of the filter holder was then connected to a vacuum assembly (i.e., suction source) and filtered to capture at least a portion of the bacteria on the filter. The vacuum assembly was connected to a vacuum flask or a vacuum manifold to which multiple units can be connected. Following vacuum filtration, the filter connection assembly was then disconnected from the sample bottle, and a polyethylene cap (U.S. Plastic Corp; see the cap 317 of FIG. 12) was used to close the base of the filter holder. The filter holder was decoupled from the filter connection assembly, and the filter holder was coupled to a sample detection container SMD3 or SMD4 or MS1 to form a second container of a sample detection system (an example of such a second container—employing SMD4—is shown by way of example as the second container 305 in FIGS. 12-14). A gasket may be used to help prevent leakage during processing and may be employed as shown in FIG. 12.

Example 14—Recovery of Bacteria Using Filtration Apparatus

A bacterial suspension of $E.$ $coli$ was prepared and serially diluted so that the dilution contained about 100 cfu/mL. Three 1000 mL sample bottles (Nalgene) were filled with 1000 mL of sterile water and 1 mL of the suspension was added to each bottle. Three 1000 mL samples were prepared for each of the filter. A filter connection assembly, constructed according to the procedure of Example 13, was assembled with Filter A, Filter B, or Filter C and connected to the filled sample bottle via the gasket. The base of the filter holder was placed over a vacuum flask attached to a vacuum assembly and the sample was filtered through the filter at a vacuum pressure of about 508 mm of mercury. After filtering, the filter holder was decoupled from the vacuum apparatus, the filter connection assembly was decoupled from the filter holder, and each of the filter membranes was removed aseptically from the filter holder and placed on a hydrated 3M™ PETRIFILM™ $E.$ $coli$/Coliform Count Plates (3M Co.), prepared according to the manufacturer's instructions, and incubated overnight at 37° C. The plates were read using a 3M™ PETRIFILM™ Plate Reader (3M Co.) and/or counted manually to determine colony forming units (cfu). Average results shown in Table 24 indicate that at least 87% of the bacteria were recovered.

TABLE 24

Recovery of $E.$ $coli$ by filtration

| Filter | Total cfu recovered Input - 150 cfu | % Recovery |
|---|---|---|
| Filter A | 135 | 90.0 |
| Filter B | 130 | 86.7 |
| Filter C | 131 | 87.3 |

Example 15—Recovery of Bacteria from Filtered Water Samples Followed by Elution

Three 1000 mL water samples containing $E.$ $coli$ were prepared for each of the filters and filtered according to the procedure of Example 14 using each of the Filters A-C. After filtering, the filter holder was decoupled from the vacuum apparatus, the base of the filter holder was capped and the filter connection assembly was decoupled from the filter holder. The filter holder comprising the filtrand was coupled to a SMD4 or MS1 sample detection container containing 5 mL of Butterfield's phosphate buffer (3M Co.). The resulting "second container" was vortexed (Fixed Speed Vortex Mixer, VWR Intl. LLC; Batavia Ill.) with filter portion down for 2 minutes at room temperature to elute the bacteria from the filter. The vortexed sample was plated on 3M™ PETRIFILM™ *E. coli*/Coliform Count Plates (3M Co.) according to manufacturer's instructions, and incubated overnight at 37° C. The plates were read using a 3M™ PETRIFILM™ Plate Reader (3M Co.) and colony forming units (cfu) were determined and average results are shown in Table 25 for each filter. Filter A showed the highest recovery of *E. coli* (about 72 to 73%; Table 25).

TABLE 25

Recovery of *E. coli* by filtration and elution

| | SMD4 | | MS1 | |
|---|---|---|---|---|
| Filter | Total cfu recovered* | % Recovery | Total cfu recovered* | % Recovery |
| Filter A | 93 | 72 | 95 | 73 |
| Filter B | 62 | 48 | 65 | 50 |
| Filter C | 46 | 35 | 50 | 38 |

*Input: 130 cfu

Example 16—Detection of Bacteria from Filtered Water Sample After Growth in the Single Microcavity Sample Detection Containers SMD3 and SMD4

Six 1000 mL water samples each containing 10 cfu of *E. coli* were prepared for each of the containers and filtered according to the procedure of Example 14 using Filter A. After filtering, the filter holder was decoupled from the vacuum apparatus, the base of the filter holder was capped and the filter connection assembly was decoupled from the filter holder. The filter holder comprising the filtrand was coupled to a sample detection container, SMD3 or SMD4 containing 7 mL of prepared COLILERT™ media. The combination of the filter holder and sample detection container SMD3 or SMD4 functioned as the "second container" in this example.

Control samples were prepared similarly, but received 1 mL of Butterfield's buffer to 1000 mL of water.

The second containers were vortexed (Fixed Speed Vortex Mixer, VWR) with filter portion down for 2 minutes at room temperature and then centrifuged (i.e. toward the microcavity) in a multipurpose centrifuge for 20 min at 4000 RPM (3220×g) according to procedure in Example 1b. After centrifuging, one set of three sample detection containers, SMD3 or SMD4 were removed from the centrifuge, inverted slowly to drain the media back into the container, away from the microcavity, and incubated at 37° C. in the inverted position. To the other set of three sample detection containers, 2 ml of separation liquid FC77 was added, and the container was incubated at 37° C. in the upright position. As described above, the separation liquid moved to the bottom of the container, essentially serving the same purpose as inverting the container to separate the bulk liquid from the microcavity.

The microcavity of the inverted container was imaged using imager system 1 (stereo microscope) and the microcavity of the container with separation liquid was imaged with imager system 2 (inverted fluorescence microscope) every hour.

SMD3 container (effective angle=45 degrees) unlike SMD4 container (effective angle=60 degrees) showed excess liquid above the top opening of the microcavity upon inversion of the container. The use of separation liquid avoided the issue of excess liquid above the top opening of the microcavity, as the separation liquid moved to the bottom of the container and covered over the top opening of the microcavity irrespective of the effective angle of the container, separating the concentrate of the sample in the microcavity from the bulk supernatant.

As shown in Table 26, the onset of fluorescence was observed at approximately 3 hours in the inverted SMD4 container and at 7 hrs in the inverted SMD3 container. However, onset of fluorescence was observed at approximately 3 hours in both sample detection containers, SMD3 and SMD4, containing separation liquid FC77. No increased fluorescence over background was seen in control samples at 3 hrs or later (up to 24 hrs of incubation).

Example 17—Detection of Bacteria from Filtered Water Sample After Growth in the Microcavity Surface Container MS1

Six 1000 mL water samples each containing 10 cfu of *E. coli* were prepared and filtered according to the procedure of Example 14 using Filter A. After filtering, the filter housing was decoupled from the vacuum apparatus, the base of the filter holder was capped and the filter connection assembly was decoupled from the filter holder. The filter holder comprising the filtrand was coupled to a MS1 sample detection container containing 10 mL of prepared COLILERT™ media. The combination of the filter holder and the sample detection container MS1 functioned as the "second container" in this example.

Control samples were prepared similarly, but received 1 mL of Butterfield's buffer to 1000 mL of water.

The second containers were vortexed (Fixed Speed Vortex Mixer, VWR) with filter portion down for 2 minutes at room temperature and then centrifuged (i.e., toward microcavities) in a multipurpose centrifuge for 20 min at 4000 RPM (3220×g) according to the procedure in Example 1c. After centrifuging, one set of three MS1 detection containers were removed, inverted slowly to drain the media back into the container, away from the microcavities, and incubated at 37° C. in the inverted position. To the other set of three MS1 detection containers, 4 ml of separation liquid FC77 was added and incubated at 37° C. in the upright position. As described above, the separation liquid moved to the bottom of the container, essentially serving the same purpose as inverting the container to separate the bulk liquid from the microcavity.

The microcavities of the inverted containers were imaged using imager system 1 (stereo microscope) and the microcavities of the containers with separation liquid were imaged with imager system 2 (inverted fluorescence microscope) every hour.

As shown in Table 26, the onset of fluorescence was observed at approximately 5 hours in both the inverted containers and containers containing separation liquid FC77. The use of separation liquid avoided inverting of the sample detection containers after centrifugation, as the separation liquid moved to the bottom of the container and covered over the top opening of the microcavities, separating the concentrate of the sample in the microcavities from the bulk supernatant. No increased fluorescence over background was seen in control samples at 5 hrs or later (up to 24 hrs of incubation).

TABLE 26

Comparison of time to detect 10 cfu of *E. coli* from filtered water samples

| | Mu-glcU fluorescence* | | | | | |
|---|---|---|---|---|---|---|
| Time | Inverted SMD3 (No separation liquid) | Upright SMD3 with FC-77 | Inverted SMD4 (No separation liquid) | Upright SMD4 with FC-77 | Inverted MS1 (No separation liquid) | Upright MS1 with FC-77 |
| 1 hr | No | No | No | No | No | No |
| 2 hr | No | No | No | No | No | No |
| 3 hr | No | Yes | Yes | Yes | No | No |
| 4 hr | No | Yes | Yes | Yes | No | No |
| 5 hr | No | Yes | Yes | Yes | Yes | Yes |
| 7 hr | Yes | Yes | Yes | Yes | Yes | Yes |
| 8 hr | Yes | Yes | Yes | Yes | Yes | Yes |
| 15 h | Yes | Yes | Yes | Yes | Yes | Yes |

Various features and aspects of the present disclosure are set forth in the following claims.

What is claimed is:

1. A method for detecting an analyte of interest in a sample, the method comprising:
providing a sample detection container comprising:
an open end configured to receive a sample, and
a closed end that includes a microcavity, the microcavity including a top opening and a base and configured to provide capillary forces to retain a sample of interest;
positioning a sample in the sample detection container;
centrifuging the sample detection container toward the microcavity to form a sediment and a supernatant of the sample;
adding a separation liquid to the sample detection container, after centrifuging the sample detection container, to displace the supernatant located outside of the microcavity from the microcavity, such that a concentrate of the sample is retained in the microcavity, the concentrate comprising the sediment, wherein the separation liquid moves between the microcavity and the supernatant located outside of the microcavity;
wherein the separation liquid has a density greater than that of the supernatant of the sample and an interfacial tension with the supernatant of at least 0.05 N/m, and wherein the separation liquid is non-toxic and inert.

2. The method of claim 1, wherein the separation liquid has a density of at least 1.2 g/ml.

3. The method of claim 1, wherein the separation liquid has a density of at least 0.2 g/ml greater than water.

4. The method of claim 1, wherein the separation liquid has a surface tension of no greater than 0.02 N/m.

5. The method of claim 1, wherein the separation liquid has an interfacial tension with the supernatant of at least 0.055 N/m.

6. The method of claim 1, wherein the sample is aqueous, and wherein the separation liquid has an interfacial tension with water of at least 0.05 N/m.

7. The method of claim 1, wherein the sample is aqueous, and wherein the separation liquid has an interfacial tension with water of at least 0.055 N/m.

8. The method of claim 1, wherein the separation liquid has a solubility in water of less than 1%.

9. The method of claim 1, wherein the separation liquid is colorless.

10. The method of claim 1, wherein the separation liquid includes a fluorocarbon-based liquid.

11. The method of claim 1, wherein the microcavity is a single microcavity.

12. The method of claim 1, wherein the microcavity is one of a plurality of microcavities.

13. The method of claim 1, wherein the microcavity contains a volume of no greater than 1 microliter.

14. The method of claim 1, wherein the microcavity has a frustoconical shape or a frustopyramidal shape.

15. The method of claim 1, wherein the microcavity includes a sidewall, and wherein the sidewall includes a draft angle of at least 10 degrees.

16. The method of claim 1, wherein an inner surface of the container has a static water surface contact angle of at least 65 degrees.

17. The method of claim 1, wherein an inner surface of the container has a dynamic receding water surface contact angle of at least 25 degrees.

18. The method of claim 1, wherein an inner surface of the container has a surface roughness characterized by a roughness average (Ra) value of less than 500 nm.

19. The method of claim 1, wherein positioning a sample in the sample detection container includes:
providing a first container assembly comprising a filter portion, the filter portion comprising a filter configured to retain the analyte of interest from the sample, the filter having a first side and comprising a filtrand of the sample on the first side; and
coupling the filter portion to the sample detection container to form a second container assembly, the filter portion and the sample detection container being coupled together such that the first side of the filter faces the microcavity of the sample detection container.

20. The method of claim 1, wherein positioning a sample in the sample detection container includes:
providing a first container assembly comprising a receptacle portion adapted to contain the sample and a filter portion adapted to be removably coupled to the receptacle portion, the filter portion comprising a filter configured to retain the analyte of interest from the sample, the filter having a first side;
filtering the sample by moving the sample in a first direction from the receptacle portion toward the first side of the filter to form a filtrand of the sample on the first side of the filter, while removing a filtrate of the sample; and
decoupling the receptacle portion and the filter portion of the first container assembly;
coupling the filter portion to the sample detection container to form a second container assembly, the filter portion and the sample detection container being coupled together such that the first side of the filter faces the microcavity of the sample detection container.

* * * * *